US007524517B2

(12) United States Patent
Schwiebert et al.

(10) Patent No.: US 7,524,517 B2
(45) Date of Patent: Apr. 28, 2009

(54) METHODS AND COMPOSITIONS FOR P2X RECEPTOR CALCIUM ENTRY CHANNELS AND OTHER CALCIUM ENTRY MECHANISMS

(75) Inventors: Erik Schwiebert, Birmingham, AL (US); Akos Zsembery, Budapest (HU)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 10/542,555

(22) PCT Filed: Jan. 20, 2004

(86) PCT No.: PCT/US2004/001298

§ 371 (c)(1),
(2), (4) Date: Aug. 29, 2005

(87) PCT Pub. No.: WO2004/064742

PCT Pub. Date: Aug. 5, 2004

(65) Prior Publication Data

US 2006/0121128 A1 Jun. 8, 2006

Related U.S. Application Data

(60) Provisional application No. 60/476,423, filed on Jun. 6, 2003, provisional application No. 60/441,045, filed on Jan. 17, 2003.

(51) Int. Cl.
*A61K 33/30* (2006.01)
*A61K 31/315* (2006.01)
*A61K 31/7076* (2006.01)
*A61P 11/00* (2006.01)
*A61P 11/06* (2006.01)

(52) U.S. Cl. ................... 424/641; 424/643; 424/682; 514/47; 514/255.06; 514/494; 514/669; 514/826; 514/851; 514/924

(58) Field of Classification Search ............... 424/9.2, 424/43, 641, 643; 514/494, 849, 851, 866; 435/7.21
See application file for complete search history.

(56) References Cited

U.S. PATENT DOCUMENTS

| 5,622,724 | A | * | 4/1997 | Bryce-Smith | ............ | 424/641 |
| 5,834,032 | A | | 11/1998 | Song | | |
| 5,840,278 | A | * | 11/1998 | Coleman | ............ | 424/45 |
| 6,514,709 | B1 | | 2/2003 | Grant | | |
| 6,926,911 | B1 | * | 8/2005 | Boucher, Jr. | ............ | 424/601 |
| 2002/0115619 | A1 | * | 8/2002 | Rubenstein et al. | ............ | 514/27 |

OTHER PUBLICATIONS

CAPLUS Abstract 2001: 30580 (2001).*
Senior, K., "pH has a role in cystic fibrosis infections," The Lancet, vol. 358, Issue 9295, p. 1786 (Nov. 24, 2001).*
Medline abstract 86146262 (1986).*
Ackerman and Clapham, Ion channels—basic science and clinical disease. *N. Engl. J. Med.* 336: 1575-1586 (1997).
Amuzescu et al. Zinc is a voltage-dependent blocker of native and heterologously expressed epithelial $Na^+$ channels. *Pflugers Arch.* 446:69-77 (2003).
Barg S. Mechanisms of exocytosis in insulin-secreting B-cells and glucagon-secreting A-cells. *Pharmacol. Toxicol.* 92: 3-13 (2003).
Berger et al. Identification and regulation of the cystic fibrosis transmembrane conductance regulator-generated chloride channel. *J Clin. Invest.* 88:1422-1431 (1991).
Braunstein et al. Cystic fibrosis transmembrane conductance regulator facilitates ATP release by stimulating a separate ATP release channel for autocrine control of cell volume regulation. *J. Biol. Chem.* 276(9):6621-6630 (2001).
Button and Brownstein Aequorin-expressing mammalian cell lines used to report calcium mobilization *Cell Calcium* 14:663-671 (1993).
Cho et al. Antibacterial effect of intraprostatic zinc injection in a rat model of chronic bacterial prostatitis. *Int. J. Antimicrob. Agents.* 19: 576-582 (2002).
Davis and Konstan Cystic fibrosis. *Am. J. Respir. Crit. Care Med.* 154(5):1229-1256 Review. No abstract available (1996).
Fuller and Benos, $Ca(2+)$-Activated $Cl(-)$ Channels: A Newly Emerging Anion Transport Family. *News Physiol. Sci.* 15:165-171 (2000).
Grantham JJ.. Polycystic Kidney disease: from the bedside to the gene and back. *Curr. Opin. Nephrol. Hypertens.* 10:533-542 (2001).
Gregory et al. Expression and characterization of the cystic fibrosis transmembrane conductance regulator. *Nature* 347:382-386 (1990).
Guay-Woodford and Desmond, Autosomal recessive polycystic kidney disease: the clinical experience in North America. *Pediatrics* 111:1072-1080 (2003).
Ito et al. Internal $Ca2+$ mobilization is altered in fibroblasts from patients with Alzheimer disease. *Proc. Natl. Acad. Sci. USA* 91: 534-538 (1994).

(Continued)

*Primary Examiner*—John Pak
(74) *Attorney, Agent, or Firm*—Ballard Spahr Andrews & Ingersoll LLP

(57) ABSTRACT

This invention relates generally to a method of increasing cytosolic $Ca^{2+}$ levels in mammalian cells comprising contacting P2X receptor $Ca^{2+}$ entry channels or any and all other $Ca^{2+}$ entry channels or mechanisms on the cell with an effective amount of a small molecule, and a composition comprising the small molecule in a delivery system. The invention has broad applicability in the pharmaceutical industry as a method of treating airway diseases (such as cystic fibrosis and asthma), ailments of the lung and airways (such as those caused by common cold pathogens or allergens in allergy), kidney diseases and renal hypertensive disorders (such as polycystic kidney disease and salt-sensitive hypertension syndromes), and endocrine disorders (such as diabetes).

13 Claims, 51 Drawing Sheets

OTHER PUBLICATIONS

Krebs et al. Abnormalities in zinc homeostasis in young infants with cystic fibrosis. *Pediatr. Res.* 48(2):256-261 (2000).

Leissring et al. Capacitative calcium entry deficits and elevated luminal calcium content in mutant presenilin-1 knockin mice. *J. Cell Biol.* 149(4):793-797 (2000).

Moran et al. A study to assess the plaque inhibitory action of a new zinc citrate toothpaste formulation. *J. Clin. Periodontal* 28(2):157-161 (2001).

North RA. Molecular physiology of P2X receptors. *Physiol. Rev.* 82(4):1013-1067 (2002).

Praetorius and Spring, Bending the MDCK cell primary cilium increases intracellular calcium. *J. Membr. Biol.* 184(1):71-79 (2001).

Riordan et al. Identification of the cystic fibrosis gene: cloning and characterization of complementary DNA. *Science* 245(4922):1066-1073 (1989).

Rohatgi et al. Na transport in autosomal recessive polycystic kidney disease (ARPKD) cyst lining epithelial cells. *J. Am. Soc. Neph.* 14(4):827-836 (2003).

Rugolo et al. ATP and $A_1$ adenosine receptor agonists mobilize intracellular calcium and activate $K^+$ and $Cl^-$ currents in normal and cystic fibrosis airway epithelial cells. *J. Biol. Chem.* 268:24779-24784 (1993).

Schafer, Abnormal regulation of ENaC: syndromes of salt retention and salt wasting by the collecting duct. *Am. J. Physiol.* 283(2):F221-F235 (2002).

Schreiber et al. Cystic fibrosis transmembrane conductance regulator activates water conductance in *Xenopus* oocytes. *Pflügers Arch.* 434(6):841-847 (1997).

Schwiebert et al. Autocrine extracellular purinergic signaling in epithelial cells derived from polycystic kidneys. *Amer. J. of Physiology* 282(4 Pt 2)):F763-F775 (Apr. 2002).

Schwiebert et al. Extracellular nucleotide signaling along the renal epithelium. *Amer. J. of Physiology* 280(6 Pt. 2):F945-F963 (Jun. 2001).

Sheng et al. External nickel inhibits epithelial sodium channel by binding to histidine residues within the extracellular domains of alpha and gamma subunits and reducing channel open probability. *J. Biol. Chem.* 277(51):50098-50111 (2002).

Smith and Welsh, cAMP stimulates bicarbonate secretion across normal, but not cystic fibrosis airway epithelia. *J. Clin. Invest.* 89(4):1148-1153. (1992).

Sohnle, P.G. et al. Effect of zinc-reversible growth-inhibitory activity in human empyema fluid on antibiotic microbicidal activity. abstract, *Antimicrobial Agents Chemotherapy*, 44:139-142, (2000).

Sperlagh, B. et al. Local regulation of [$^3$H]-noradrenaline release from the isolated guinea-pig right atrium by $P_{2x}$-receptors located on axon terminals. abstract, *British Journal of Pharmacology*, 131(8):1775-1783, (2000).

Sullivan et al. Measurement of [$Ca^{2+}$] using the fluorometric imaging plate reader (FLIPR). *Methods in Molecular Biology*, vol. 114: *Calcium Signaling Protocols* 114:125-133 (1999).

Sutters and Germino, Autosomal dominant polycystic kidney disease: molecular genetics and pathophysiology. *J. Lab. Clin. Med.* 141(2):91-101 (2003).

Tarran,R et al. Regulation of murine airway surface liquid volume by CFTR and $Ca^{2+}$-activated $Cl^-$ conductances. *J. Gen. Physiol.* 120:407-418 (2002).

Taylor et al. Epithelial P2X purinergic receptor channel expression and function. *J. Clin. Invest.* 104(7):875-884 (Oct. 1999).

Truong-Tran et al. New insights into the role of zinc in the respiratory epithelium. *Immunol. Cell Biol.* 79:170-177 (2001).

Wang et al. A Novel Member of a Zinc Transporter Family is Defective in Acrodermatitis Enterpathica. *Am. J. Human Genet.* 71:66-73 (2002).

Wilson PD. Epithelial cell polarity and disease. *Am. J. Physiol.* 272(4 Pt 2):F434-F442 (1997).

Zabner et al. Correction of cAMP-Stimulated Fluid Secretion in Cystic Fibrosis Airway Epithelia: Efficiency of Adenovirus-Mediated Gene Transfer in vitro. *Human Gene Therapy* 5(5)585-593 (1994).

Zsembery et al. Sustained calcium entry through P2X nucleotide receptor channels in human airway epithelial cells. J Biol Chem. Apr. 11, 2003;278(15):13398-408. Epub Feb. 3, 2003.

Zsembery et al. Extracellular zinc and ATP restore chloride secretion across cystic fibrosis airway epithelia by triggering calcium entry. J Biol Chem. Mar. 12, 2004;279(11):10720-9. Epub Dec. 29, 2003.

http://members.aol.com/henryhbk/endocrine.html.

http://www.upei.ca/~cidd/Diseases/endocrine%20diseases/endocrine%20disorders%20list.htm.

http://homepage.psy.utexas.edu/HomePage/Class/Psy308/Humm/lectures/05-7Neurotransmitters&Drugs.

\* cited by examiner

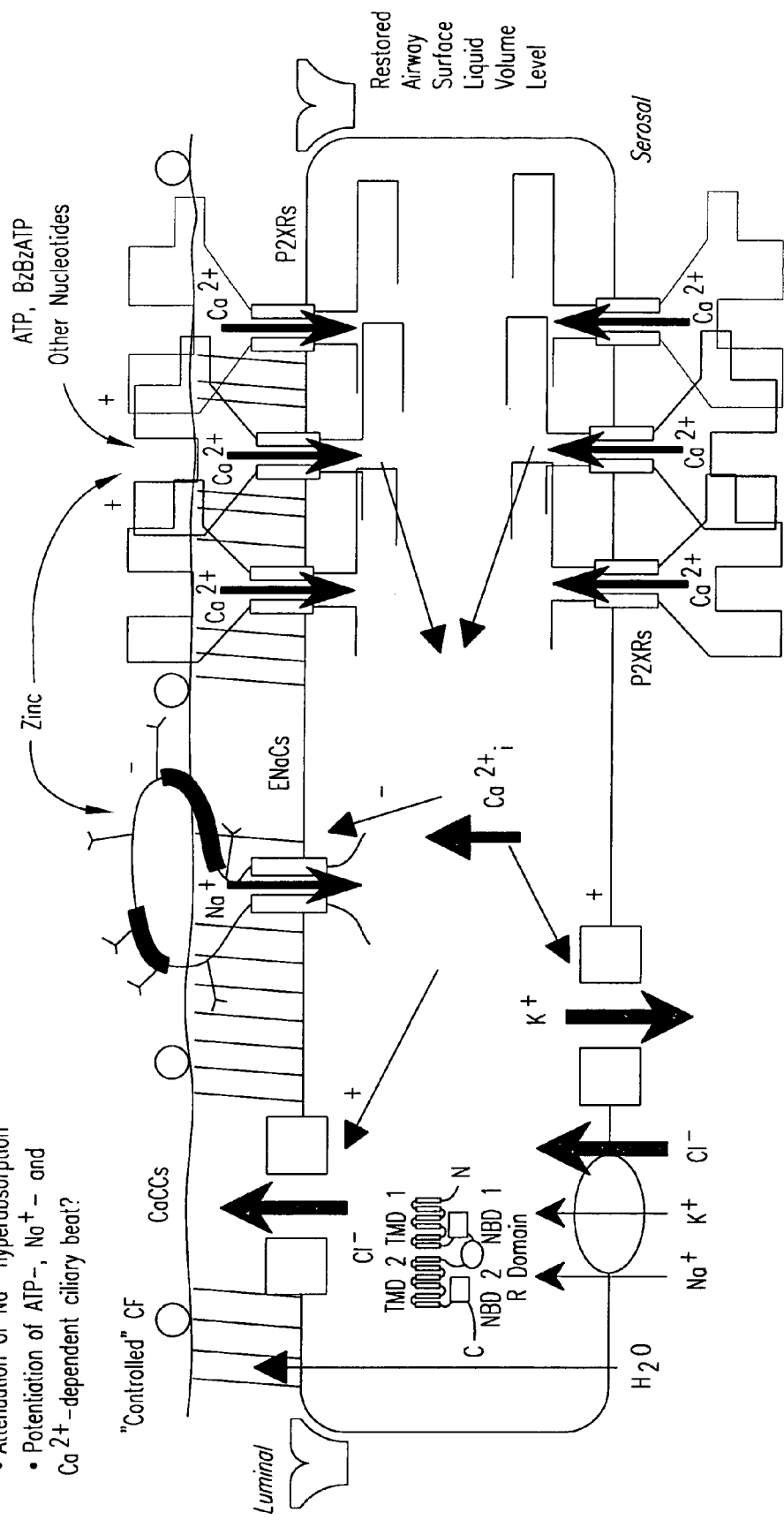

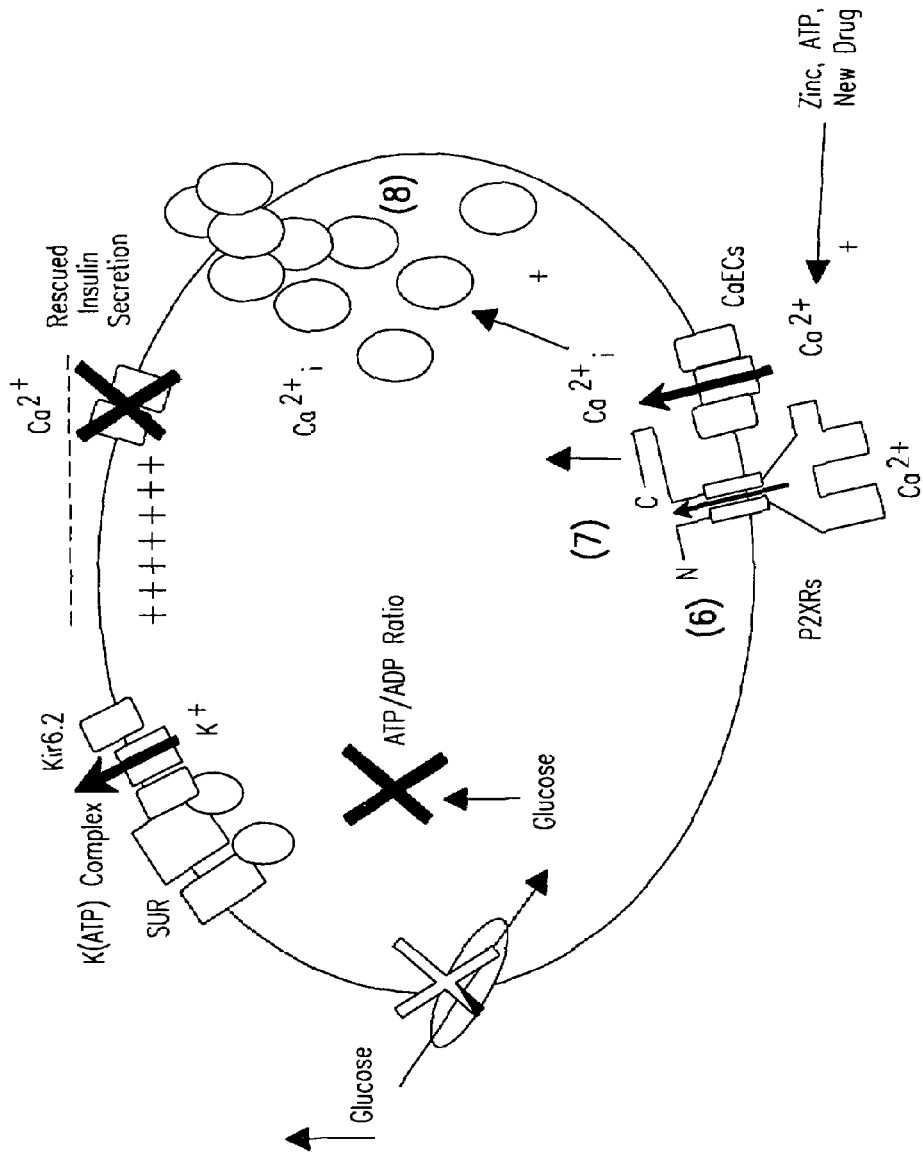

Transepithelial Nasal Potential Difference Values of Control, ΔF508 CF and Bitransgenic CF Mice

| | Control Cftr(+/-) | n | CF Cftr(ΔF508/ΔF508) | n | Bitransgenic Cftr(-/-) | n |
|---|---|---|---|---|---|---|
| Starting point | -18.7 ± 6.5 | 19 | -26.3 ± 7.2* | 11 | -26.1 ± 3.8* | 14 |
| Low [Cl⁻]$_e$ (Na⁺; pH:7.3) | -5.5 ± 1.5 | 8 | +3.7 ± 1.6* | 3 | +4.8 ± 2.5* | 7 |
| ATP + ZnCl$_2$ (Na⁺; pH:7.9) | -4.7 ± 1.8 | 6 | -4.0 ± 2.0 | 3 | -3.8 ± 2.0 | 12 |
| Low [Cl⁻]$_e$ (Na⁺; pH:7.9) | -4.8 ± 2.0 | 6 | +5.4 ± 2.8* | 7 | +6.7 ± 4.0* | 3 |
| ATP + ZnCl$_2$ (NMDG; pH:7.9) | -6.0 ± 1.4 | 2 | -9.4 ± 1.6*# | 8 | -9.7 ± 3.1*& | 3 |
| Low [Cl⁻]$_e$ (NMDG; pH:7.9) | -4.8 ± 3.3 | 5 | | | +5.8 ± 1.9* | 4 |
| ATP + ZnCl$_2$ (NMDG; pH:7.9) | -5.7 ± 1.2 | 3 | | | -10.2 ± 1.3*& | 6 |
| ATP alone (NMDG; pH:7.9) | -7.3 ± 0.6 | 3 | | | -2.3 ± 1.0§ | 4 |
| Low [Cl⁻]$_e$ (NMDG; no added Ca²⁺; pH:7.9) | | | | | +6.0 ± 0.8* | 4 |
| ATP + ZnCl$_2$ (NMDG; no added Ca²⁺; pH:7.9) | -1.3 ± 0.6$ | 3 | | | -2.0 ± 1.2$ | 4 |

FIG. 8F

| Modified Saline** (pH 7.3) | | | Modified Saline (pH 7.3) + 15 mM Glucose | | |
|---|---|---|---|---|---|
| Time | Absorbance | [Insulin] | Time | Absorbance | [Insulin] |
| 15" | 0.682 ± 0.03 | ~3.0 ng/ml | 15" | 1.070 ± 0.05 | ~5.0 ng/ml |
| 15' | 0.765 ± 0.04 | 3.25 | 15' | 0.957 ± 0.07 | 4.5 |
| 30' | 0.794 ± 0.06 | 3.5 | 30' | 1.204 ± 0.10 | 5.5 |
| 60' | 1.794 ± 0.09 | 9.0 | 60' | 2.065 ± 0.05 | 11.0 |
| 120' | 1.137 ± 0.05 | 5.0 | 120' | 1.105 ± 0.18 | 5.0 |

| Standard Curve | |
|---|---|
| Absorbance | [Insulin] |
| 0.248 | 0.0 |
| 0.226 | 0.2 ng/ml |
| 0.280 | 0.5 ng/ml |
| 0.377 | 1.0 ng/ml |
| 0.559 | 2.0 ng/ml |
| 1.10 | 5.0 ng/ml |
| 1.91 | 10.0 ng/ml |
| ~3.0 | ~20 ng.ml |

*Generous gift of Dr. Chris Newgard at Duke.

**Modified saline is 0 Na (substituted fully by NMDG), 0 Mg, and 3 mM Ca.

FIG.16A

| Designation | Mode of Stimulation | Epithelial Polarity |
|---|---|---|
| Store-operated $Ca^{2+}$ channels (SOCs) or $I_{CRAC}$ | ER store depletion | Unclear |
| TRP channels | ER store depletion (partial) Alkaline extracellular pH (partial) | Apical & Basolateral |
| P2X receptor $Ca^{2+}$ entry channels | Extracellular zinc and ATP | Apical & Basolateral |
| ECaC or CAT (Related to TRPs) | ER store depletion | Apical |
| $Ca^{2+}$-permeable non-selective cation channel (NSCC) | Stretch-activated | Apical |

FIG.19D

METHODS AND COMPOSITIONS FOR P2X RECEPTOR CALCIUM ENTRY CHANNELS AND OTHER CALCIUM ENTRY MECHANISMS

CROSS REFERENCE TO RELATED APPLICATIONS

This application is a 371 of PCT/US04/01298, filed on Jan. 20, 2004, which claims the benefit of priority of U.S. Provisional Application 60/441,045, filed Jan. 17, 2003 and Provisional Application 60/476,423, filed Jun. 3, 2003, which applications are incorporated herein by this reference in their entireties.

This invention was funded by the National Institutes of Health, NIH R01, grant HL-63934. Therefore, the United States Government has certain rights in this invention.

BACKGROUND OF THE INVENTION

1. Field of the Invention

This invention relates generally to increasing cytosolic $Ca^{2+}$ levels in mammalian cells by triggering $Ca^{2+}$ entry from extracellular "stores" (e.g., by $Ca^{2+}$ from the solution vehicle entering the cell).

The invention has broad applicability in the pharmaceutical industry in screening for agents that stimulate $Ca^{2+}$ entry in methods of treating bacterial infections, inflammatory conditions and diseases, airway diseases and infections (such as cystic fibrosis, asthma, common cold, lung and airways bacterial infections), gastrointestinal (GI) diseases and infections (cystic fibrosis, GI bacterial infections), kidney diseases (like polycystic kidney disease, salt-sensitive hypertension, and other renal hypertension syndromes), and endocrine and neuroendocrine disorders such as type I and type II diabetes, Alzheimer's disease, Addison's disease, pituitary dwarfism (pituitary GH secretion insufficiency), and amylotrophic lateral sclerosis (ALS or Lou Gehrig's disease).

2. Background Art

The epithelial lining of the respiratory tract contains both mucous-secreting goblet cells and ciliated cells. These cells are bathed in fluid and a layer of mucous rests on top of the cilia. In healthy lungs, the ciliated cells beat the mucous layer that contains inhaled foreign particles and microorganisms toward the larger bronchi and trachea, where it is either expectorated or swallowed. (Davies, Z. A. *NurseWeek.com*, May 7, 2002). In airway diseases, these functions are impaired.

In subjects with cystic fibrosis (CF), for example, the fluid and the mucous layer are dehydrated. The dehydrated mucous is thick and sticky, which inhibits the cilia from propelling mucous out of the airway. It accumulates and progressively obstructs the bronchioles and bronchi. The sticky mucous also creates an ideal environment for the proliferation of bacteria.

In CF, cyclic AMP- and protein kinase A-dependent transepithelial $Cl^-$ transport is impaired because of mutations in the CF gene that encodes for the protein, the cystic fibrosis transmembrane conductance regulator, or CFTR (Riordan et al, *Science* 245:1066-1073, 1989). Originally, CFTR was thought to function exclusively as a low conductance $Cl^-$ channel (Gregory et al, *Nature* 27:382-386, 1990; Berger et al, *J. Clin. Invest.* 88:1422-1431, 1991). More recently, it has become clear that CFTR also regulates a series of other transporters and ion channels, such as the $Cl^-/HCO_3$ exchanger, the $NaHCO_3$ cotransporter, epithelial $Na^+$ channels (ENaCs), $K^+$ channels, and aquaporin water channels (Schreiber et al., *Pflugers Arch.* 434:841-847, 1997). In particular, ENaCs, a protein separate from but regulated by CFTR, are upregulated or hyperactive in CF are another class of dysregulated ion channel that needs correction with a CF therapeutic. Impaired $Cl^-$ transport is shared as a key disease phenotype by CF epithelia from all affected tissues and that this pathway is lost in CF. Therefore, activation of a cAMP-independent $Cl^-$ secretory pathway through exploitation of a naturally expressed epithelial protein is of interest for therapy in CF and other airway diseases.

Increases in $Ca^{2+}$ activate epithelial chloride ($Cl^-$) and potassium ($K^+$) channels (Rugolo et al., *J. Biol. Chem.* 268: 24779-24784, 1993; Tarran et al., *J. Gen. Physiol.* 120:407-418, 2002); however, epithelial $Na^+$ channels (ENaCs) are inhibited by $Ca^{2+}$ increases in epithelia. Thus, needed in the art are methods and a composition for selectively stimulating $Ca^{2+}$-activated $Cl^-$ channels (CaCCs) as a possible substitute for cAMP-dependent cystic-fibrosis transmembrane conductance regulator (CFTR) $Cl^-$ channels impaired in cystic fibrosis (Fuller C M, Benos D J. *News Physiol. Sci.* 15: 165-171, 2000).

A subset of CF patients also have GI abnormalities, mostly related to pancreatic insufficiency, a loss of secretion of pancreatic enzymes and bicarbonate, and inadequate digestion and absorption of essential nutrients. Although malabsorption of elements like zinc has been reported in subjects with CF (Krebs et al. *Pediatr. Res.* 48: 256-261, 2000), such elements have not been used to treat airway diseases. Zinc is a trace element that is derived from diet and is enriched in certain tissues (Troung-Tran et al. *Immunol. Cell Biol.* 79: 170-177, 2001). Zinc oxide creams alleviate dermatitis, including acrodermatits enteropathica in CF patients caused by zinc malabsorption and deficiency. Defective activity of a zinc transporter is linked to this form of dermatitis (Wang et al. *Am. J. Human Genet.* 7: 66-73, 2002). Zinc also alleviates symptoms of or speeds recovery from rhinoviral infections. Homeopathic remedies such as Zicam™ and ColdEeze™, based on zincum gluconicum and administered either orally or as a nasal gel, are available over-the-counter to reduce symptoms and speed recovery from the common cold. Zinc has not been used previously to modulate $Ca^{2+}$ entry.

SUMMARY OF THE INVENTION

The invention offers distinct advantages over the prior art because it provides zinc, along with other ligands, as agonists for naturally occurring, expressed mucosal airway epithelial P2X receptor $Ca^{2+}$ entry channels and other families of $Ca^{2+}$ entry channel or other additional $Ca^{2+}$ entry mechanisms for airway, kidney, and endocrine diseases. The invention also provides the advantage of a screening method for identifying other potential agonists for mammalian calcium entry mechanisms and uses for the identified agonists. Additional advantages of the invention will be set forth in part in the description which follows or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention as claimed.

In accordance with the purpose(s) of this invention, as embodied and broadly described herein, this invention, in one aspect, relates to a method of increasing cytosolic $Ca^{2+}$ levels to create a sustained $Ca^{2+}$ signal in mammalian cells. More specifically, such a sustained $Ca^{2+}$ signal in a cell is accomplished by stimulation of $Ca^{2+}$ entry mechanisms, e.g., (by P2X receptor $Ca^{2+}$ entry channels, other classes of $Ca^{2+}$ entry channels, or additional types of $Ca^{2+}$ entry mechanisms) with zinc, nucleotides, or other small molecules or ligands.

In another aspect, the invention relates to a method of treating an airway disease in a subject, comprising contacting epithelial cells in the airways of the subject with an effective amount of a P2X receptor agonist, such as $Zn^{2+}$ or other small molecules or ligands. Other diseases treated by the methods of the invention include polycystic kidney disease.

In another aspect, the invention relates to methods of screening for an epithelial $Ca^{2+}$ channel agonist. For example, the method can comprise contacting an epithelial cell with a test compound, detecting calcium levels in the epithelial cell, and screening for an elevation in calcium compared to a control level. The method can also comprise contacting a test compound with a cell that expresses a heterologous nucleic acid that encodes a $Ca^{2+}$ entry channel agonist, detecting levels of calcium in the cell, an elevation in calcium as compared to a control indicating $Ca^{2+}$ entry channel agonist.

The invention also relates to methods of inhibiting inflammation, inhibiting bacterial growth and inhibiting viral growth in a subject comprising administering to the subject an effective amount of $Zn^{2+}$ in the composition of the invention.

In yet another aspect, the invention relates to a composition used in the methods described herein.

BRIEF DESCRIPTION OF THE DRAWINGS

The accompanying drawings, which are incorporated in and constitute a part of this specification, illustrate embodiments of the invention and together with the description, serve to explain the principles of the invention.

FIG. 1B shows cystic fibrosis airway epithelial cell model illustrating the P2X receptor $Ca^{2+}$ entry channel therapeutic targets and the therapeutic benefits of zinc. The multiple therapeutic benefits of targeting P2X receptor calcium entry channels and the application of zinc are highlighted. Zinc, by stimulating P2X receptor calcium entry channels with the co-agonist, ATP (or another nucleotide), rescues chloride and fluid secretion.

FIG. 3 shows kidney tissue models illustrating the change in architecture and environment in Polycystic Kidney Disease (PKD) and the two different forms of PKD.

FIG. 4 shows normal cellular mechanism of insulin secretion in a β cell, a defective β cell in diabetes, and a model illustrating the P2X Receptor $Ca^{2+}$ entry channel therapeutic targets and the therapeutic benefits of zinc. FIG. 4B shows that in a diabetic β cell, one or more of the steps in this cellular and molecular mechanism are impaired, leading to a loss of insulin secretion. In a hypothetically "controlled" β cell, an agonist to "alternative" $Ca^{2+}$ entry channels like the P2X receptor $Ca^{2+}$ entry channels such as zinc circumvents the glucose- and voltage-dependent steps in the pathway and rescues insulin secretion in a glucose- and voltage-independent manner. The same principles apply to any endocrine cell that harbors packaged agonist in a vesicle or granule where there is failure to secrete hormone or agonist.

FIG. 5 shows stimulation of calcium entry via P2X receptor $Ca^{2+}$ entry channels with zinc and/or ATP

FIG. 6 shows the involvement of specific epithelial P2XR subtypes in zinc and ATP-induced calcium entry. FIG. 6C shows definitive proof for $P2X_4$ involvement. siRNA "protein knockdown" experiments show a markedly reduced calcium entry signal after $P2X_4$ siRNA construct transient transfection (Right). At Left, a scrambled siRNA construct was transfected transiently into the cells and a typical response is shown similar to mock-transfected cells and parental controls. Similar data is shown versus scrambled control for $P2X_5$ siRNA and $P2X_6$ siRNA. Like the result for $P2X_4$ siRNA, $P2X_6$ siRNA reduced the overall magnitude of the sustained calcium plateau, while $P2X_5$ siRNA did not affect the magnitude of the response but it caused the calcium entry phenotype to be transient. These data, along with copper competitive inhibition of zinc stimulation and the chemical and pH dependency of the zinc and ATP-induced calcium entry, point to significant roles for $P2X_4$, $P2X_5$, and $P2X_6$ in zinc and/or ATP-induced calcium entry.

FIG. 7 shows biochemical analysis of P2X4 expression in human airway epithelial cells in vitro. Immunoblot analysis of IB3-1 cells grown as non-polarized monolayers in flasks using rabbit polyclonal antibodies against P2X4 receptors revealed two different blotted molecular weight proteins. A smaller band of the predicted molecular mass for P2X4 (46 kDa) was detected, as was a larger, broader, glycosylated band at 60-70 kDa. The positions of molecular mass markers are shown on the left (in kDa).

FIG. 9 shows zinc inhibition of ENaC-mediated Na+ absorption in NPD assays of CF and control mice. The NPD recordings were performed in standard NaCl-replete lactated Ringer of normal pH and reflect the early stages of the experiments not focused upon in the FIG. 8, examining rescue of Cl− secretion.

FIG. 10 shows multiple zinc formulations inhibit NFkappaB induction in human airway epithelial cells.

FIG. 11 shows multiple zinc formulations are bacteriastatic for non-mucoid and mucoid *Pseudomonas aeruginosa* as well as *E. coli* and *Bacillus anthracis*.

FIG. 12 shows sodium hyperabsorption in ARPKD. Upregulated transepithelial voltage and current in PKD mutant monolayers was confirmed by five different investigators that measured the monolayers (n=12 each set) and observed similar results, sometimes with blinding or with no prompting.

FIG. 13 shows expression of P2XR calcium entry channel targets in renal epithelia. Degenerate RT-PCR for P2XR gene family and specific RT-PCR for P2X6 showed shared and ubiquitous expression of P2X4 and P2X5 as well as significant expression of P2X6 mRNA. This result in mouse kidney epithelial cells in vitro is similar to P2XR expression results in human airway epithelia.

FIG. 14 shows sodium hyperabsorption in ARPKD and inhibition by zinc and nickel.

FIG. 15 shows expression of P2X4 receptor calcium entry channels in rat pancreatic β cells.

FIG. 16 shows enzyme-linked absorbance aAssay (ELISA) analysis of Insulin secretion from INS-1 cells showing stimulation with 15 mM glucose. INS-1 cells are normally grown in 11 mM glucose. Two days prior to the ELISA assay, confluent INS-1 cells are starved of glucose to a lower concentration less than 5 mM. Then, cells are washed with a saline Ringer and challenged with 15 mM glucose. Insulin secretion was biphasic in vitro and in vivo, with an immediate burst of insulin secretion in the first seconds and minutes that waned after 15 minutes, while there was a second, slower peak of insulin secretion that appeared 1-2 hours after the stimulus. FIG. 16A shows the absorbance numbers are shown for the control (without glucose), the experimental (with 15 mM glucose), and the standard curve for the ELISA to quantify amount of insulin secreted.

FIG. 17 shows the effects of changes in cation content and pH of the Ringers Solution during insulin secretion assays versus the 15 mM glucose stimulus. The colored or filled bars show significantly greater insulin detected versus control.

FIG. 19 shows the chemistry and structure of extracellular zinc- and ATP-gated P2X receptor calcium entry channels. FIG. 19D shows the classification of calcium entry channel targets for High Throughput Screening for Lung, Renal, and Endocrine Disorders. This figure shows all known calcium entry channels.

FIG. 20 shows high throughput screens for the screening of ligands.

DETAILED DESCRIPTION OF THE INVENTION

Figure 1A:
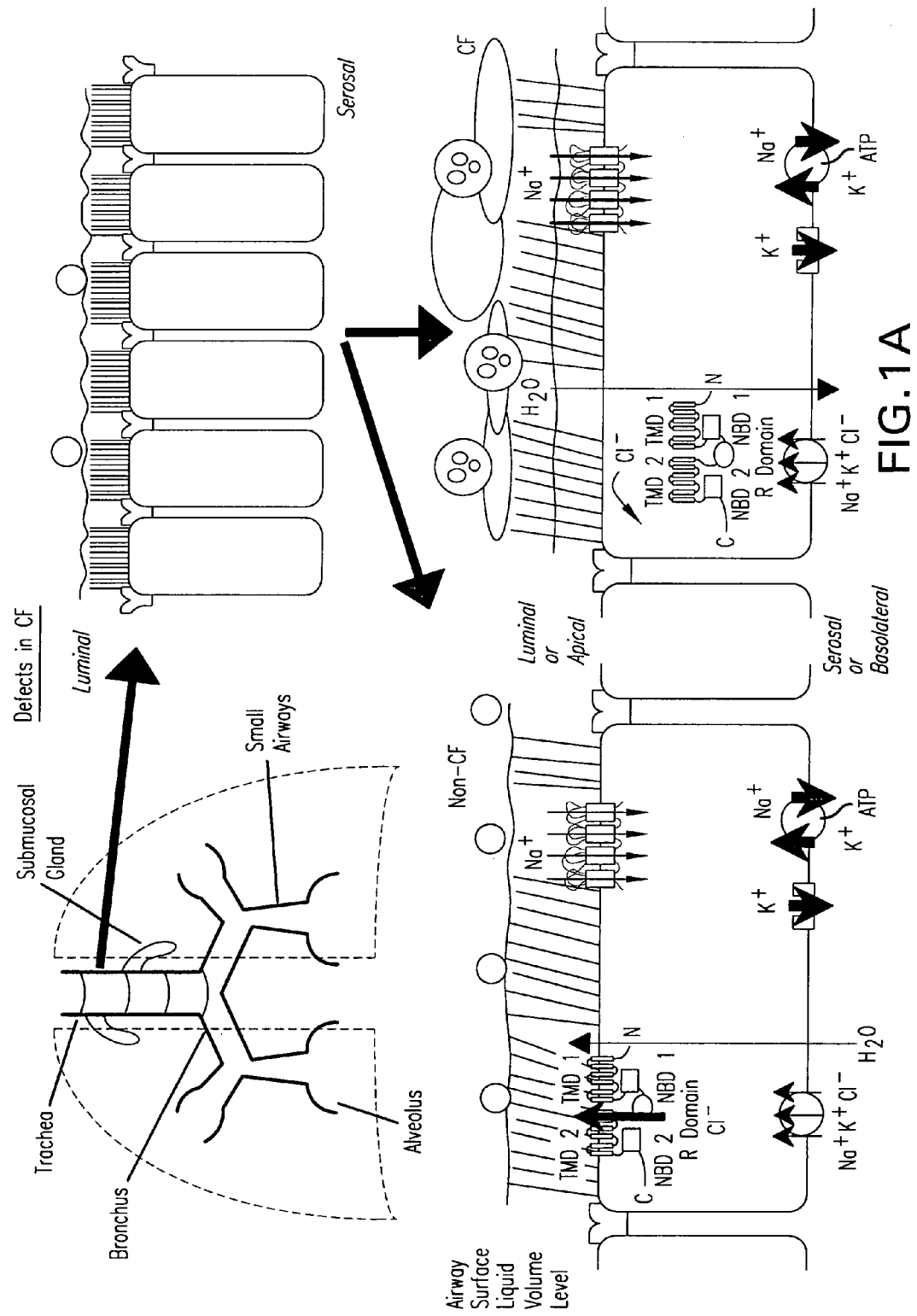
FIG. 1A shows a series of model figures depicting the lung, a ciliated airway, and a close-up model of a non-CF and a CF airway epithelial cell. In the non-CF cell, a balance of salt and water transport keep the airway surface fluid that lines the airways at a constant and closely regulated depth so that the cilia can beat freely and clear mucous globules. This is driven by CFTR chloride channel function and by CFTR being able to regulate other ionic conductances (the epithelial sodium channel ENaC being shown here). In the CF cell, CFTR is absent from the apical or luminal ciliated membrane or is dysfunctional. A lack of chloride permeability results as well as dysinhibited and heightened ENaC-mediated sodium absorption. This dehydrates the airway lining fluid and cilia beat is impaired. As such, the mucous layer dehydrates and thickens, ciliary beat is impaired, mucociliary clearance is attenuated, and a neutrophil-dominated immune response to inflammation and *Pseudomonas aeruginosa* bacterial infection results.
Figure 2A:
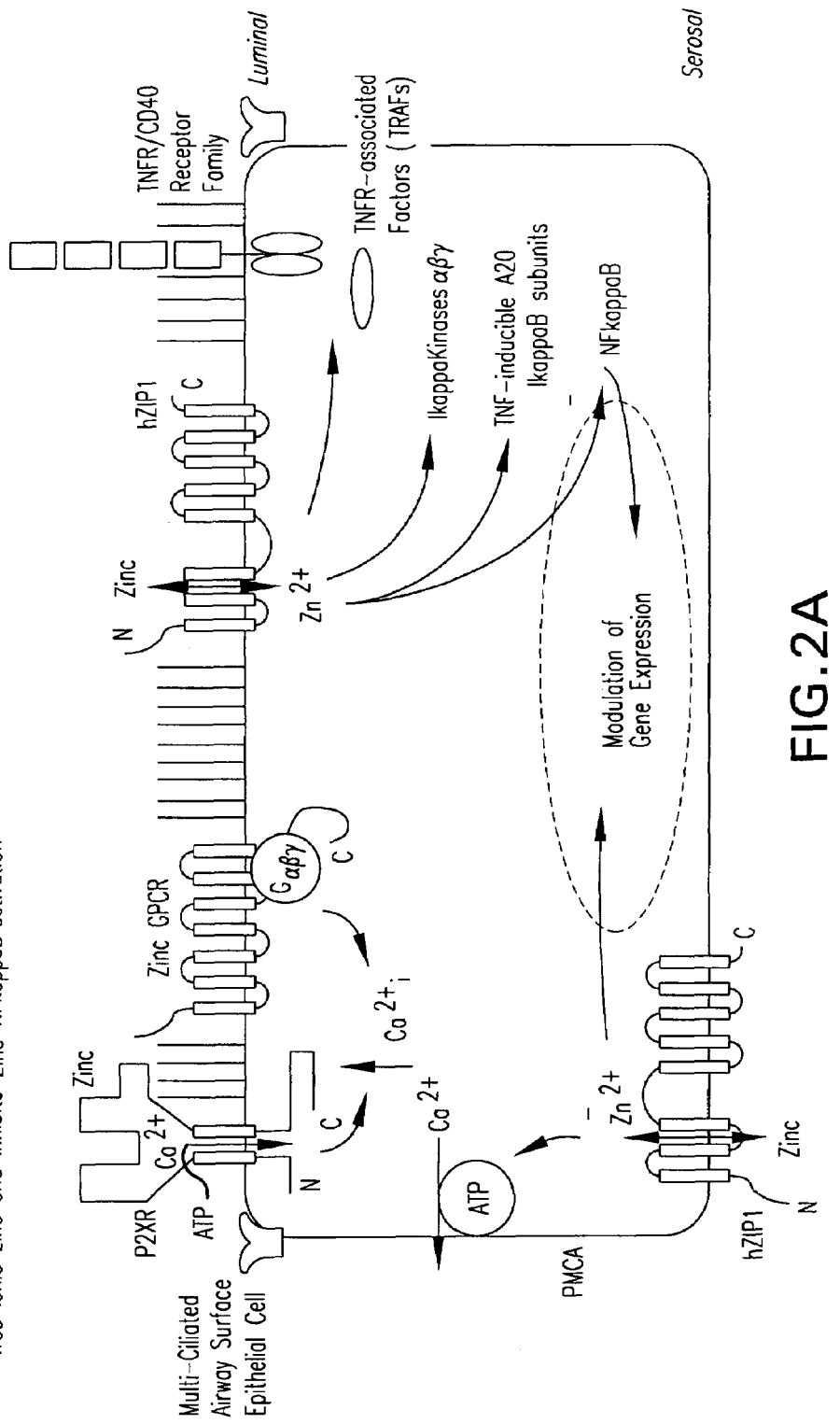
FIG. 2A shows that in addition to anti-inflammatory effects, zinc enters the cell and binds to and inhibits one or more signaling molecules that activate the key inflammatory signaling transcription factor, NFkappaB, or bind to and inhibit NFkappaB itself.
Figure 2B:
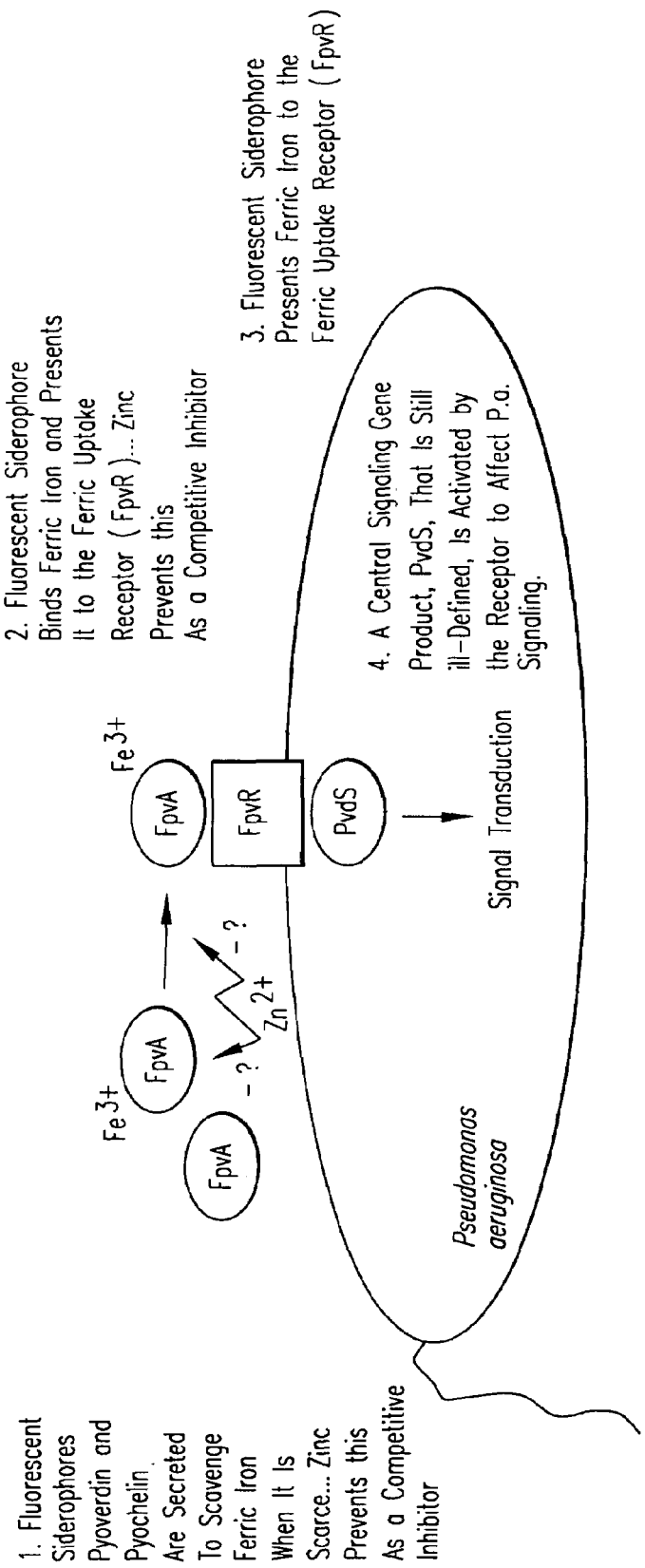
FIG. 2B shows the same time in the extracellular milieu surrounding both non-mucoid or mucoid *Pseudomonas aeruginosa*, as well as many other bacteria that share a metal scavenging system essential for growth and survival in the host. Avirulent lab strains of *E. coli* and *Bacillus anthracis* (anthrax) are inhibited in their growth and killed in a manner similar to non-mucoid and mucoid *Pseudomonas aeruginosa* by a variety of different zinc formulations.
Figure 3A:
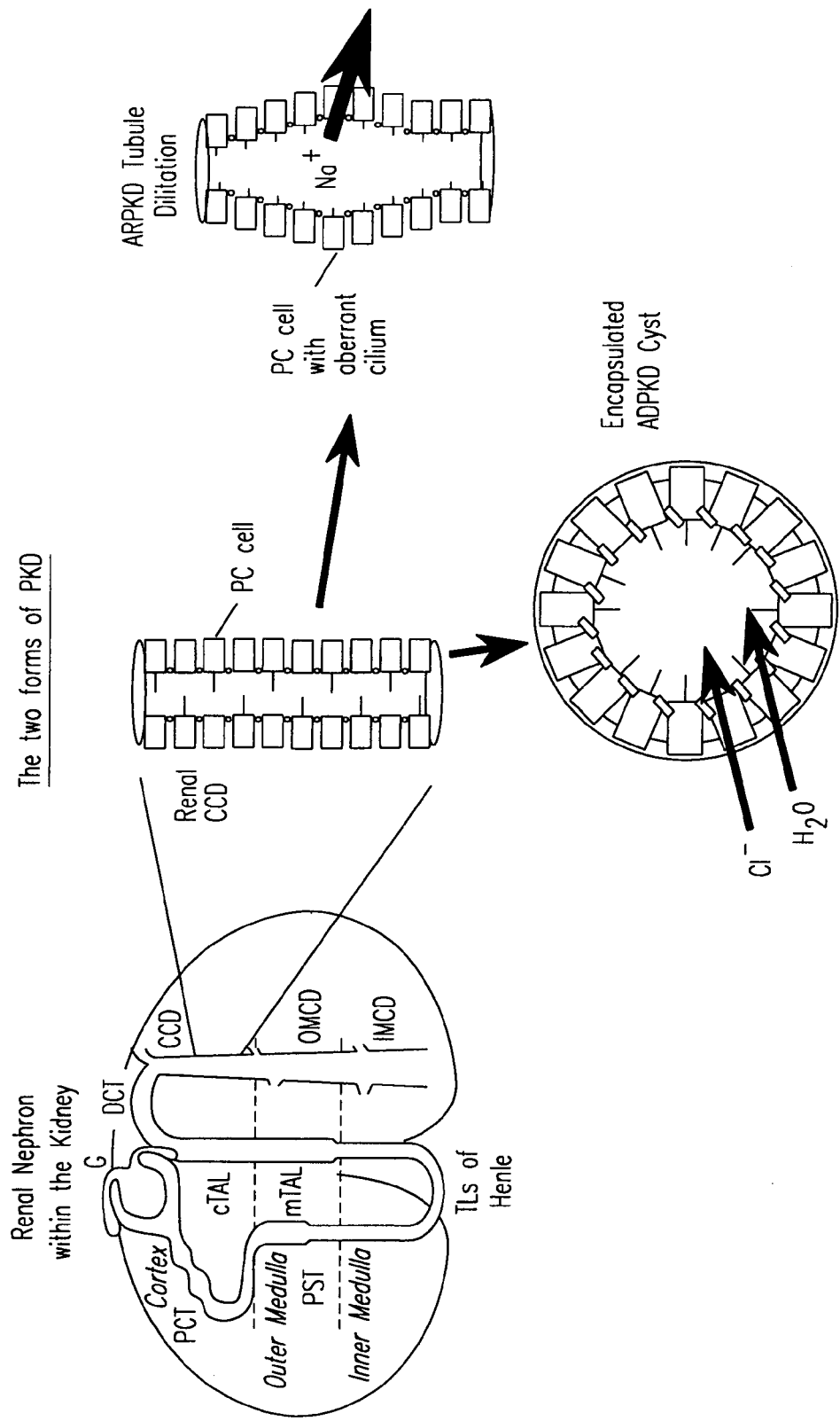
FIG. 3A shows a series of model figures depicting a renal nephron, the functional unit of the kidney, a normal renal tubule, and dysfigured renal tubules in autosomal dominant PKD (ADPKD) and autosomal recessive PKD (ARPKD) are shown. In ADPKD, both ends of a normal tubule close or pinch off, creating a fluid-filled cyst that is encapsulated by a single monolayer of cystic epithelial cells. In this new abnormal structure, chloride and water secretion mechanisms that are normally present become detrimental to the disease and cause accumulation of fluid within the cyst and expansion of the volume and size of each cyst. As such, the overall size of the kidney progresses from the size of a fist to the size of a football. In ARPKD, the normal tubules become profoundly dilated, leading to some kidney expansion. However, in this form of the disease, hyperabsorption is prevalent in the majority of subjects along with enhanced water excretion, leading to profound hypertension.
Figure 3B:
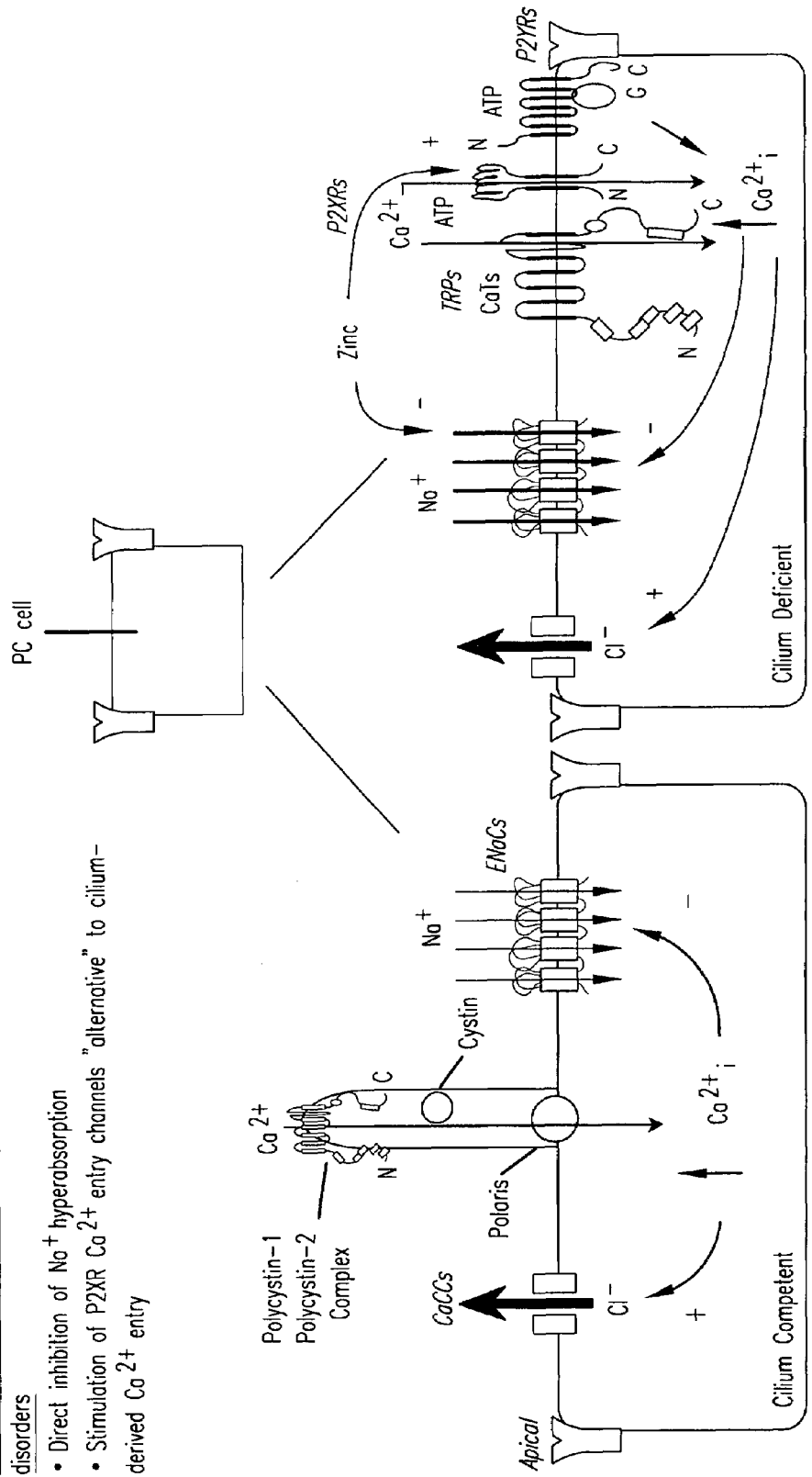
FIG. 3B shows collecting duct epithelial cell model illustrating the P2X receptor $Ca^{2+}$ entry channel therapeutic targets and the therapeutic benefits of zinc in ARPKD and in renal hypertensive disorders. In a normal principal cell, an apical central cilium is present that allows $Ca^{2+}$ entry stimulated by flow, touch, or another mechanical stimulus. In ARPKD, this cilium is dysfunctional or lost altogether, leading to enhanced sodium absorption in the human condition and in a mouse model of PKD. As such, stimulation of "alternative" $Ca^{2+}$ entry channels like the P2X receptor $Ca^{2+}$ entry channels rescues this $Ca^{2+}$ signal normally provided by an intact cilium.
Figure 4A:
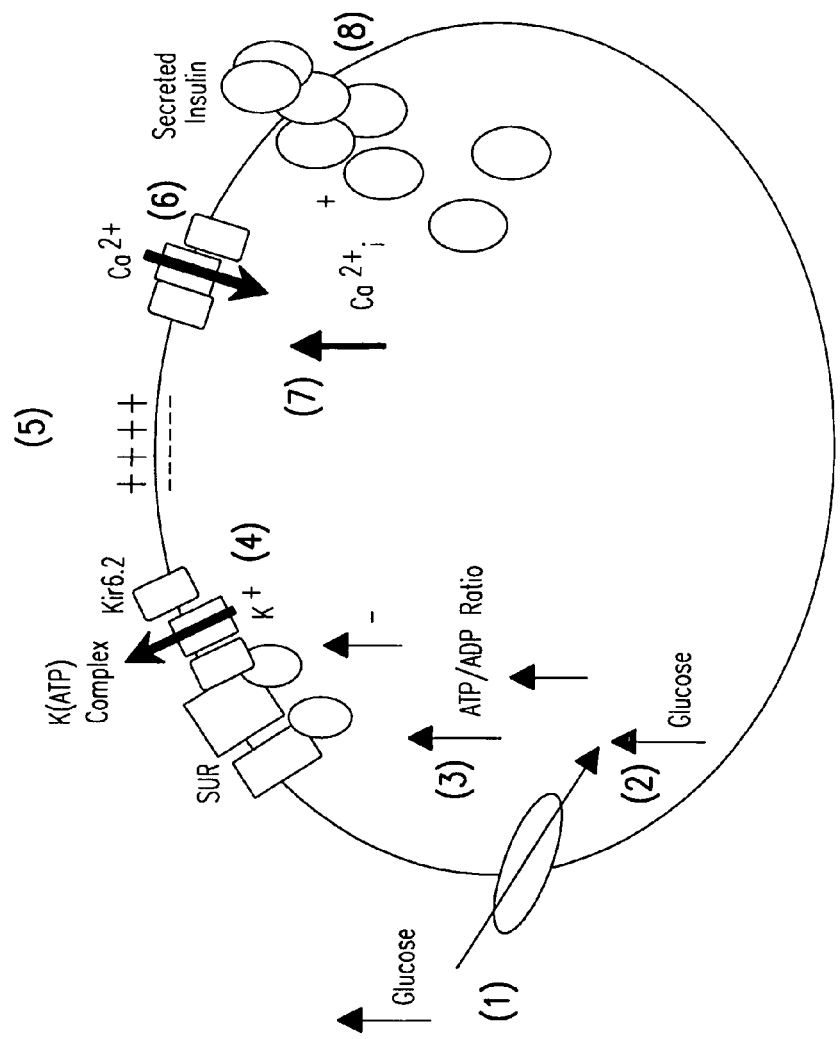
FIG. 4A shows insulin secretion and the cellular and molecular steps from glucose entry through exocytosis of insulin granules in a normal β cell within a pancreatic islet. Insulin secretion from the normal β cell is dependent upon glucose and a depolarization of the cell membrane voltage.
Figures 1, 5A:
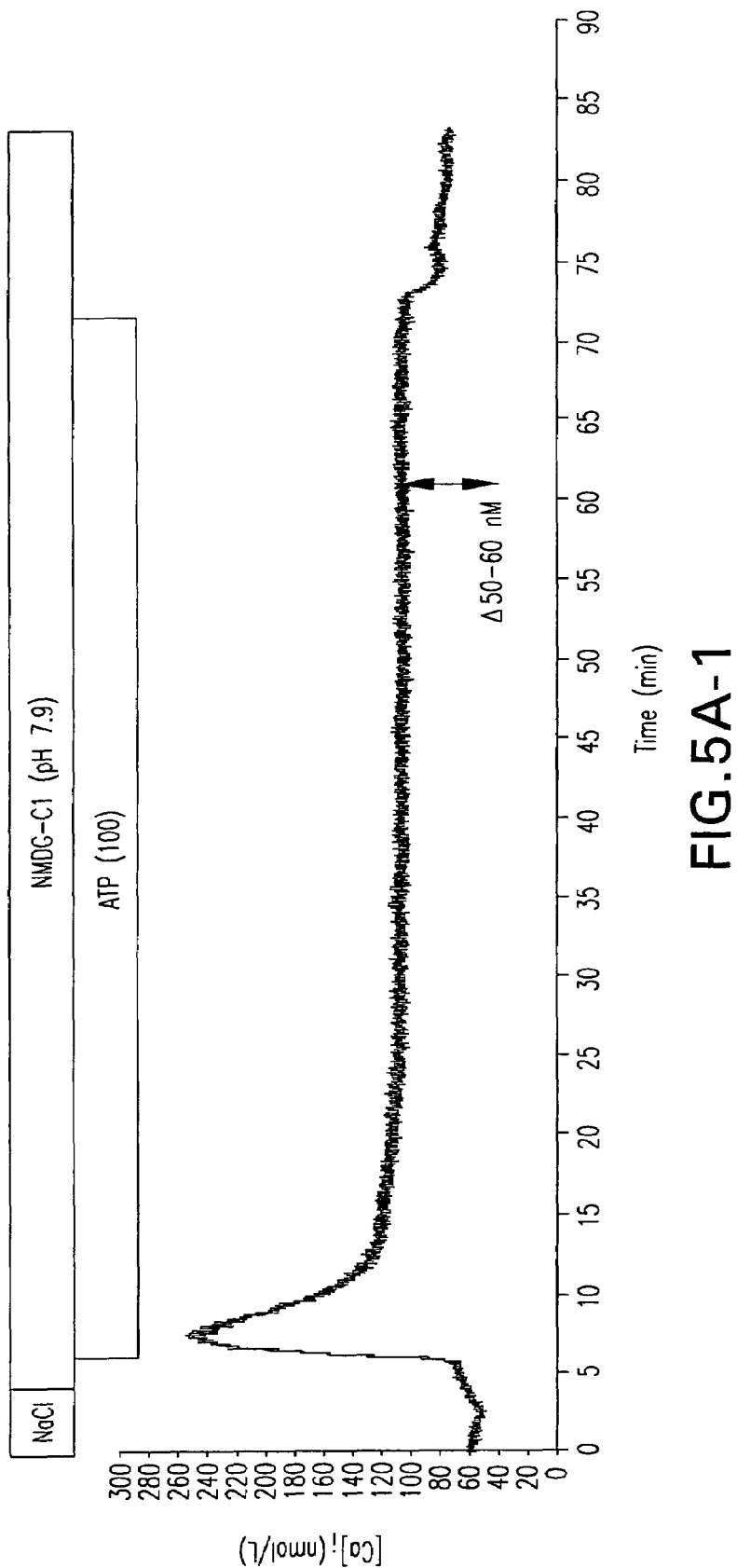
FIG. 1 shows lung tissue and cell model illustrating the airway environment and the multiple defects and problems in cystic fibrosis.
FIG. 5A shows the reversibility, long-lived, and reproducible nature of the sustained plateau induced by ATP and mediated by $P2X_4$. The transient spike that shows tachyphylaxis and disappears over time is ER-derived $Ca^{2+}$ release triggered by P2Y G protein-coupled receptors, the other subfamily of purinergic receptors expressed by epithelial cells.
Figures 2, 5A:
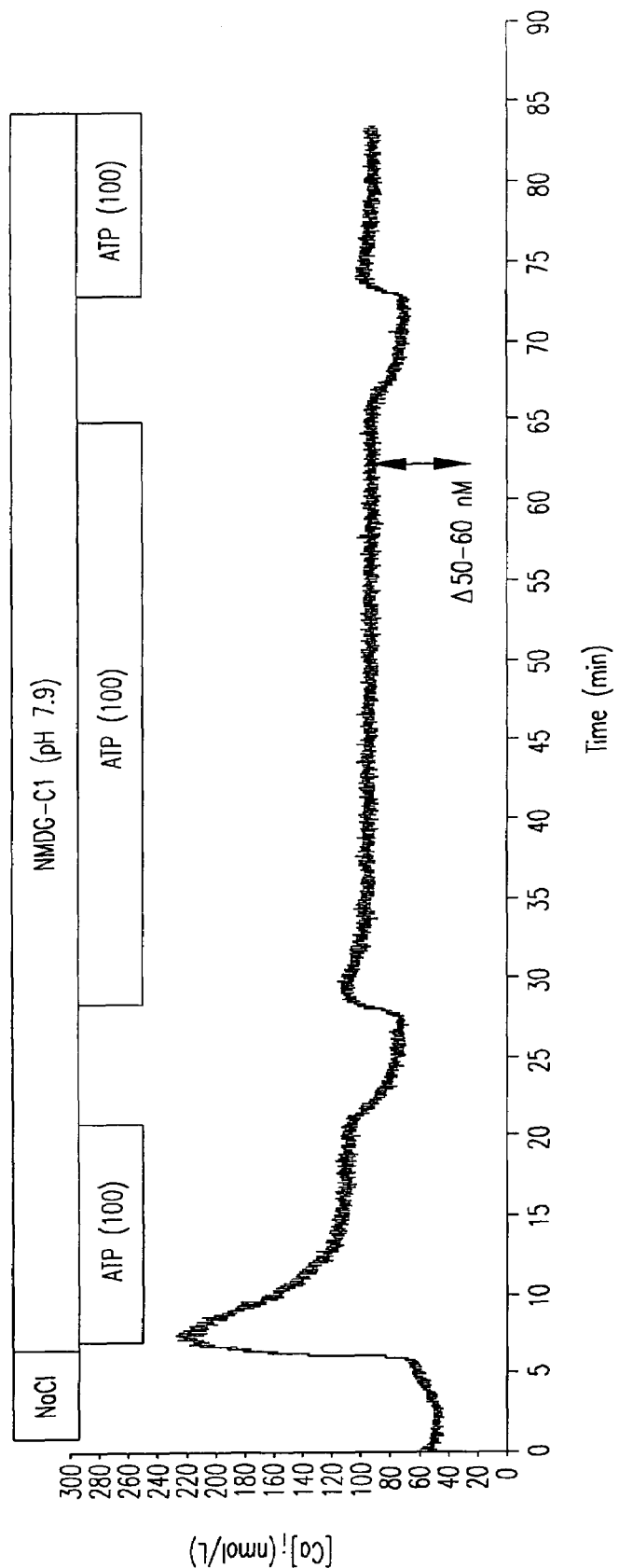
FIG. 2 shows zinc epithelial cell biology, chemistry and microbiology relevant to attenuation of inflammation and infection in CF, asthma, and the common cold. This CF airway epithelial cell model highlights the anti-inflammatory (FIG. 2A) and anti-bacterial (FIG. 2B) cellular and molecular mechanisms of a zinc-based therapy in a solution sprayed into the nose or inhaled by aerosolization or nebulization into the nasal passages, airways and lung.
Figure 5B:
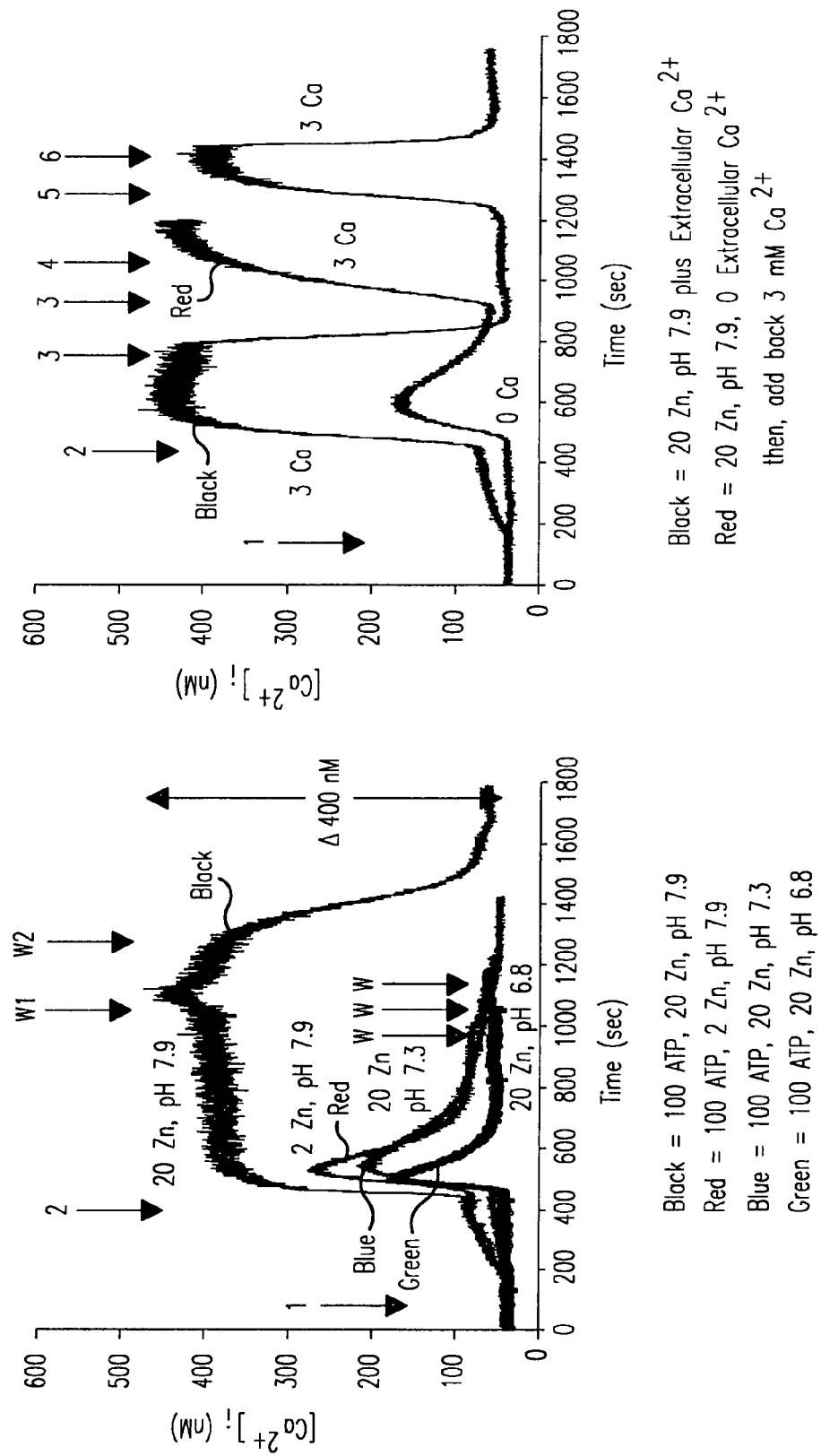
FIG. 5B shows the effect of ATP and $ZnCl_2$ on $[Ca^{2+}]_i$ in IB3-1 cells under different extracellular ionic conditions ideal for promoting $Ca^{2+}$ entry via P2X receptor $Ca^{2+}$ entry channels as well as any and all $Ca^{2+}$ entry channels (Left). After perfusing the cells with $Na^+$-containing Ringer solution (pHe 7.3), extracellular $Na^+$ was substituted by NMDG, extracellular $CaCl_2$ concentration was increased from 2 mM to 3 mM, and extracellular $MgCl_2$ was removed in all experiments. The NMDG-containing medium had pH 7.9, 7.3, and 6.4. When $[Ca^{2+}]_i$ reached a new steady state, ATP (100 µM) and $ZnCl_2$ (20 µM) or ATP (100 µM) and $ZnCl_2$ (2 µM) were added to the superfusion medium. Both agonists were washed out at the same time as indicated (W), except in black trace where ATP was first removed (W1) and then $ZnCl_2$ (W2). No loss occurred in the plateau upon removal of ATP but full reversal from the plateau upon removal of $ZnCl_2$. At right, two traces show the effect of $ZnCl_2$ (20 µM) alone in IB3-1 cells in the presence and in absence of extracellular $Ca^{2+}$. In the first case, zinc can be added again after a brief washout period and the sustained $Ca^{2+}$ plateau is re-acquired, showing reproducibility. In the second case, an ER-derived transient is triggered by zinc in the absence of extracellular $Ca^{2+}$, while re-addition of extracellular $Ca^{2+}$ unmasked zinc-facilitated $Ca^{2+}$ entry. These effects were also observed in other non-CF and CF human airway epithelial cell lines and primary cultures.
Figures 5C, 5D:
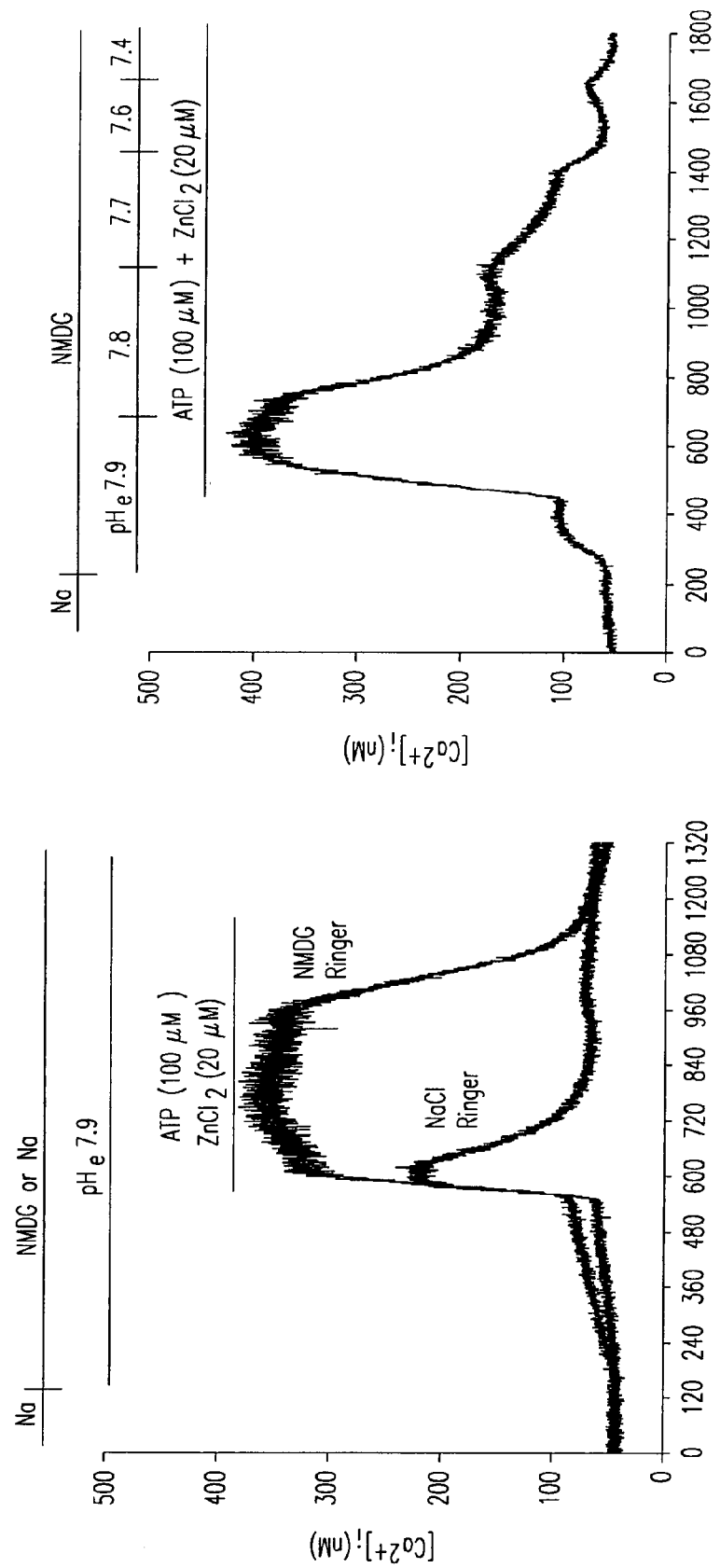
FIG. 5C shows effects of $ZnCl_2$ (20 µM) alone in IB3-1 cells in the presence and in absence of extracellular $Na^+$. Ionic composition of the superfusion medium was optimized as in FIG. 5B. A sustained plateau in $[Ca^{2+}]_i$ was shown in the absence of $Na^+$, while a transient spike was only triggered in $Na^+$ containing medium.
FIG. 5D shows ATP and zinc stimulation of $Ca^{2+}$ entry is again shown under optimal alkaline pH 7.9 conditions. Then, the pH was titrated back to neutral pH, showing the dependence of epithelial P2XR-mediated $Ca^{2+}$ entry on an alkaline external pH.
Figure 5F:
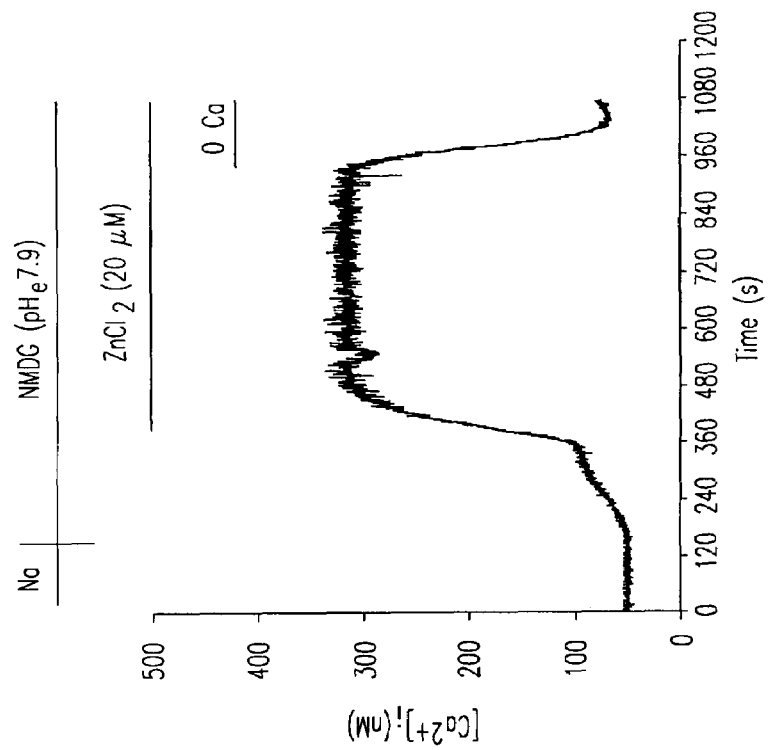
FIG. 5F shows dependence upon external $Ca^{2+}$ is shown for zinc-induced $Ca^{2+}$ entry, because the sustained plateau disappears in 0 extracellular $Ca^{2+}$.
Figure 5E:
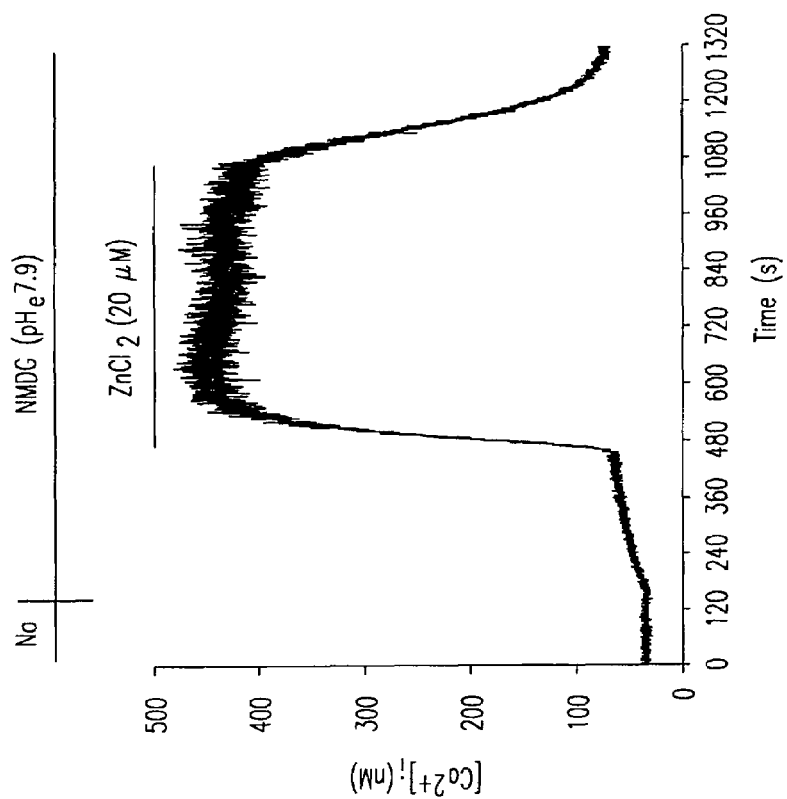
FIG. 5E shows reversibility of the zinc-induced $Ca^{2+}$ entry plateau is shown to be rapid upon removal of the biometal.
Figure 6A:
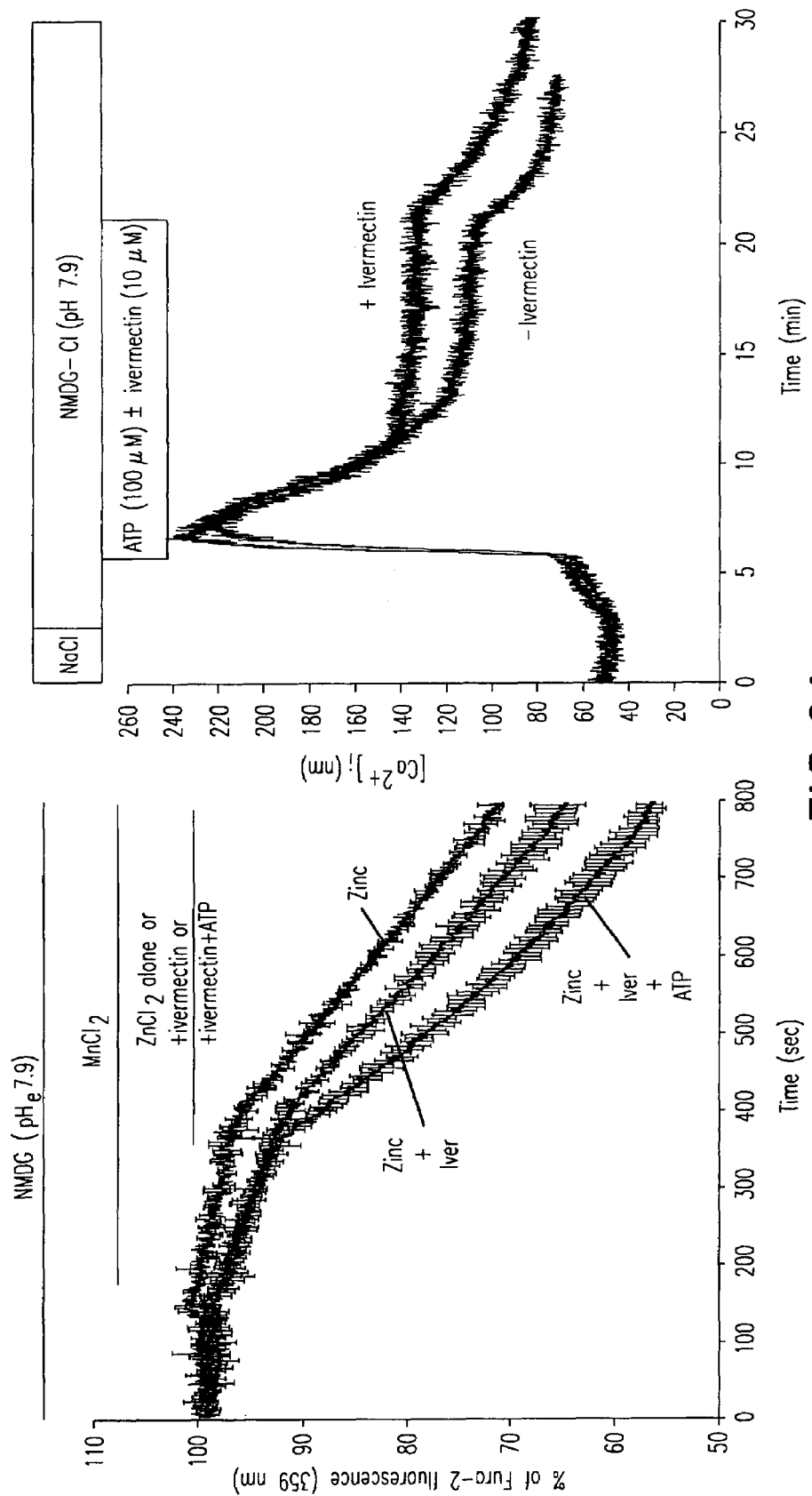
FIG. 6A shows that ivermectin is a selective allosteric modulator of the $P2X_4$ receptor channel subtype. Ivermectin was included with ATP and/or zinc in manganese entry and Fura-2 quenching assays (Left) and in direct measurement of Fura-2 fluorescence (Right). In both assays, ivermectin potentiated the zinc and/or ATP induced manganese or calcium entry, showing pharmacological evidence for $P2X_4$ involvement.
Figure 6B:
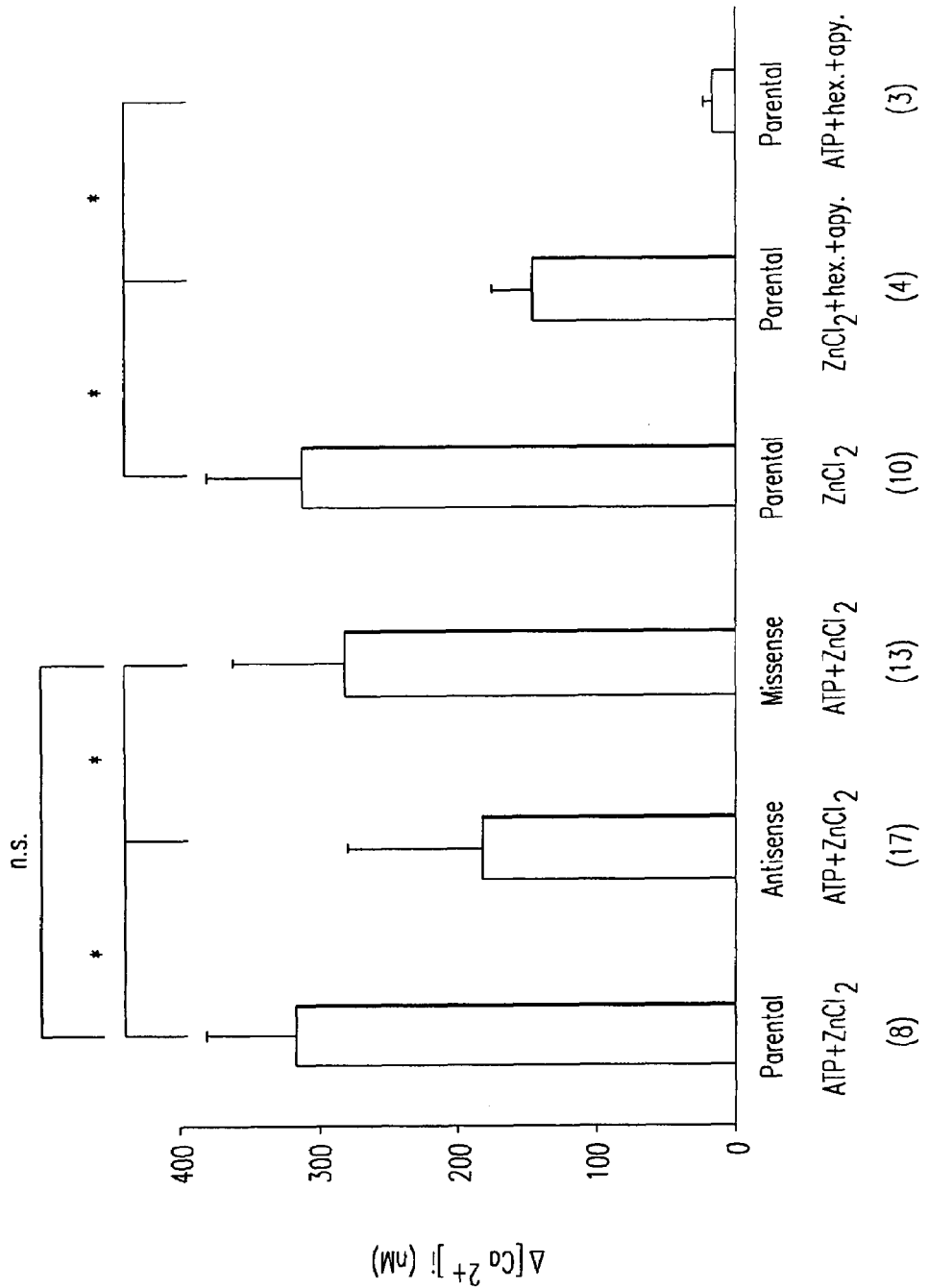
FIG. 6B shows further proof for $P2X_4$ involvement. IB3-1 CF airway epithelial cells were transiently transfected with antisense or missense constructs for $P2X_4$. The data, expressed as mean±SD for the sustained plateau of calcium entry 5 minutes after addition of agonist, show a 50% reduction in the sustained calcium signal with antisense "knockdown" of $P2X_4$ (an effect confirmed by immunoblotting for $P2X_4$ in parallel) versus controls. Experiments are also shown for zinc and ATP stimulation in the absence and presence of two different ATP scavenger enzymes, hexokinase and apyrase. Partial inhibition of zinc induction of sustained calcium entry by the ATP scavengers shows that some ATP is being released endogenously by the cells in this assay that contributes to the signal due to mechanically stimulated ATP release by flow of solution over the cells.
Figure 7A:
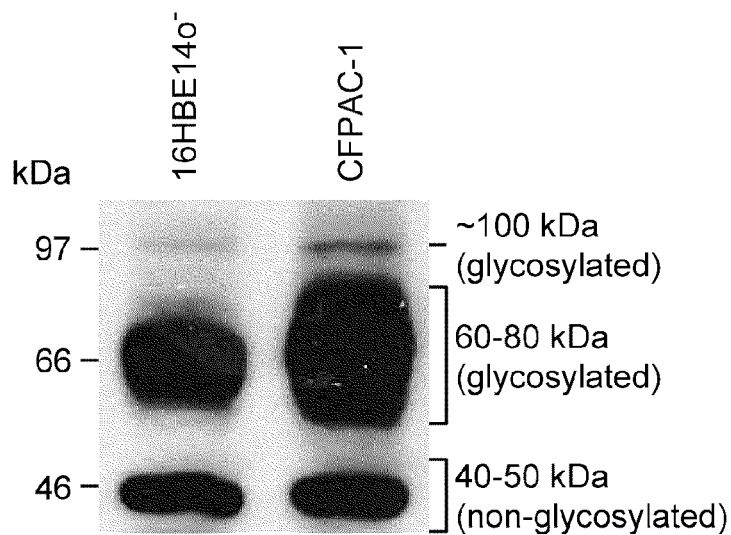
FIG. 7A shows immunoblot analysis of 16HBE14o-non-CF human airway epithelial cells and CFPAC-1 human CF pancreatic epithelial cells grown as polarized cell monolayers. The stronger expression is seen in polarized cell monolayers and the presence of a 40-50 kDa band is also seen (unglycosylated predicted molecular mass, a 60-80 kDa band (glycosylated form), as well as an even larger form at approximately 100 kDa (glycosylated form). Tunicamycin (10 µM), an inhibitor of glycosylation, added to the culture medium in 24 hour incubation of confluent cell monolayers grown in flasks abolished the 100 kDa form and inhibited the expression of the 60-80 kDa band, yielding more of the 40-50 kDa unglycosylated form. Peptide immunogens for P2X1, P2X2, and P2X7 did not block the P2X4 signaling, revealing additional specificity.
Figure 7B:
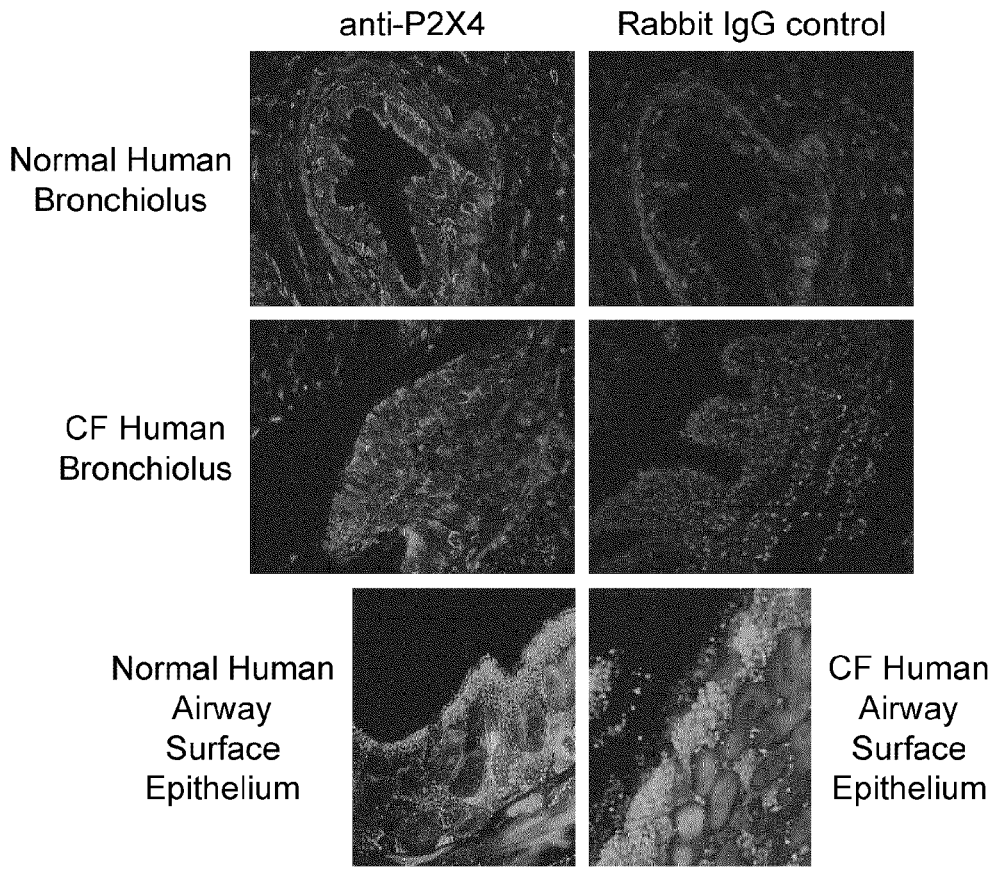
FIG. 7B shows immunohistochemical analysis of P2X4 expression in human airway epithelial cells in vivo. Staining with an anti-P2X4 antibody revealed localization on both the apical and basolateral membranes of airway surface epithelia, the basal half of cilia on ciliated airway surface epithelia, and in the cytosol of ciliated and non-ciliated cells and alveolar type II pneumocytes. Parallel staining for CFIR was done to verify the non-CF versus CF tissue sections as well as to provide an apical membrane marker. Co-staining was performed for P2X4 versus the tight junction marker, ZO-1, and versus ciliary tubulins (β and γ-tubulin). The following panels are presented. Staining is shown for P2X4 in normal human bronchiolus (a) and a rabbit IgG control of the same section (b). Anti-P2X4 staining is shown for CF human bronchiolus (c) and a rabbit IgG control (d). The entire airway surface epithelium is stained as well as some cells in the interstitium. Closer views are shown of the airway surface epithelium in normal (e) and CF (f) tissues showing the staining of the cilia atop the luminal membrane, in the luminal membrane, and intracellularly in the apical pole of the airway surface epithelium. In alveolar sections, intense P2X4 staining was revealed in the intracellular aspects of alveolar type II pneumocytes versus paired rabbit IgG controls. Apical CFTR staining was observed on the cell surface in the normal bronchioles, on ciliated and non-ciliated cells as well as in alveolar region in type 1 pneumocytes versus paired rabbit IgG controls. In CF tissue sections, staining was observed only in few cells and it appeared perinuclear. Staining for CFTR was undertaken to have a parallel apical membrane marker for the epithelium and to verify that the tissues were non-CF or CF. Co-staining of P2X4 versus two other epithelial markers, ZO-1 for the tight junction that lies between apical and basolateral membrane domains and beta- and gamma-tubulins that are found in cilia atop the airway surface epithelium. Co-staining revealed co-localization on the basal half of the cilia above the apical membrane for P2X4 and the ciliary tubulins. The staining is most dramatic in the most columnar epithelia in a given tissue. P2X4 and ZO-1 co-staining showed staining for P2X4 above the level of the tight junction that serves as the boundary between apical and basolateral membrane domains as well as on the apical membrane beneath the cilia at the level of the tight junctions. Six non-CF and 3 CF tissues were stained and screened in this analysis.

The present invention may be understood more readily by reference to the following detailed description of preferred embodiments of the invention and the Examples included therein and to the Figures and their previous and following description.

Definitions

As used in the specification and the appended claims, the singular forms "a," "an" and "the" include plural referents unless the context clearly dictates otherwise.

Thus, for example, reference to "a small molecule" includes mixtures of one or more small molecules, and the like.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

The terms "higher," "increases," "elevates," or "elevation" refer to increases above control level. The terms "low," "lower," "reduces," or "reduction" refer to decreases below control levels. For example, basal levels are normal in vivo levels prior to, or in the absence of, addition of an agent such as zinc or another small molecule or ligand.

"Epithelial cells" include, for example, airway epithelial cells, gastrointestinal cells, pancreatic cells, hepatocytes, cholangiocytes, and kidney cells.

"Airway epithelial cells" are defined as cells that form a barrier between the airways and the external environment. These cells either can be involved in the secretion or uptake or can perform a simple barrier function. These cells are found, by way of example, in the nasal cavity, nasopharynx, trachea, bronchi, bronchioles, and alveoli.

"Gastrointestinal epithelial cells" are defined as cells that line the alimentary canal, including the gastrointestinal tract. These cells can be involved in secretion, uptake, or can form a simple barrier. These cells can include, but are not limited to, lining cells of the following: the mouth, posterior pharynx, esophagus, gastroesophageal junction, stomach, gastroduodenal junction, the small intestine, duodenum, jejunum, the large intestine including the cecum, ilium, vermiform appendix, the colon, including the ascending colon, transverse colon, descending colon, and the rectum, as well as the pancreas and gall bladder. One example of a cystic fibrosis pancreatic epithelial cell is the CFPAC cell line.

"Renal epithelial cells" are defined as cells that line the tubules of the nephron of the kidney. These cells can be involved in secretion and/or absorption of substances and they can also form a simple barrier. These cells can include, but are not limited to, epithelial cells of the proximal tubule, all limbs of the loops of Henle, distal and connecting tubules, and all segments of the collecting duct. Examples are the principal cells of the collecting duct from normal and diseased kidneys that include mCCD-K1 cells, mIMCD-K2 cells, mutant and rescued orpk PC cells, for example.

"Endocrine cells" include, for example, pancreatic β cells, secretory endotroph cells of the pituitary and adrenal glands, and neurons that secrete key neurotransmitters in Alzheimer's disease and Lou Gehrig's disease. "Pancreatic β cells" refers to the insulin-secreting cell in the islets of Langarhans in the endocrine pancreas, a gastrointestinal tissue. Other "neuroendocrine or endocrine cells" can reside in the central nervous systems and/or in the pituitary and adrenal glands.

The term "airway disease" includes, but is not limited to, any disease of the respiratory system, such as obstructive dyspnea, restrictive dyspnea, lung embolism, emphysema, bronchitis, bronchiectasis, bronchiolitis, pneumonia, tracheal stenosis, pneumothorax, empyema, pleurisy, pleural effusions, alpha-1 antitrypsin deficiency, alveolar capillary dysplasia, black lung, asthma, lymphagioleiomyomatosis, pulmonary fibrosis, respiratory distress syndrome, tuberculosis, cystic fibrosis, and silicosis.

The term "renal hypertensive disorder" includes, but is not limited to, any disease of the renal system, such as salt-sensitive hypertension, Liddle's syndrome, Bartter's syndrome, Bartter's syndrome, and Gitelman's syndrome.

The term "failure to secrete endocrine disorder" includes, but is not limited to, any disease of an endocrine cell that is resident within any tissue, such as diabetes of the endocrine pancreas, pituitary dwarfism, and Addison's disease.

The term "test compound" is defined as any compound to be tested for its ability to interact with a selected channel, e.g., an epithelial $Ca^{2+}$ entry channel agonist. Examples of test compounds include, but are not limited to, small molecules such as $K^+$, $Ca^{2+}$, $Mg^{2+}$ $Fe^{2+}$ or $Fe3+$, as well as the anions $SO42-$, $H2PO4-$ (or $H3PO4$) and $NO3-$. Also, drugs, molecules, and compounds that come from combinatorial libraries where thousands of such ligands that are screened by drug class can also be used as test compounds.

The terms "control levels" or "control cells" are defined as the standard by which a change is measured, for example, the controls are not subjected to the experiment, but are instead subjected to a defined set of parameters, or the controls are based on pre- or post-treatment levels.

The compositions of the invention can be administered in vivo in a pharmaceutically acceptable carrier. By "pharmaceutically acceptable" is meant a material that is not biologically or otherwise undesirable. Thus, the material may be administered to a subject, without causing unacceptable biological effects or interacting in a deleterious manner with any of the other components of the pharmaceutical composition in which it is contained. The carrier would naturally be selected to minimize any degradation of the active ingredient and to minimize any adverse side effects in the subject, as would be well known to one of skill in the art.

The compositions maybe administered orally, parenterally (e.g., intravenously), by intramuscular injection, by intraperitoneal injection, transdermally, extracorporeally, topically or the like, including topical intranasal administration or administration by inhalant. As used herein, "topical intranasal administration" means delivery of the compositions into the nose and nasal passages through one or both of the nares and can comprise delivery by a spraying mechanism or droplet mechanism, or through aerosolization of the small molecule or ligand.

Administration of the compositions by inhalant can be through the nose or mouth via delivery by a spraying or droplet mechanism. Delivery can also be directly to any area of the respiratory system (e.g., lungs) via intubation.

The dosage of the compositions required will vary from subject to subject, depending on the species, age, weight and general condition of the subject, the severity of the airway disorder being treated, the particular active agent used, its mode of administration and the like. Thus, it is not possible to specify an exact amount for every composition. However, an appropriate amount can be determined by one of ordinary skill in the art using only routine experimentation given the teachings herein.

The materials may be in solution, suspension (for example, incorporated into microparticles, liposomes, or cells). These may be targeted to a particular cell type via antibodies, receptors, or receptor ligands.

Suitable carriers and their formulations are described in Remington: The Science and Practice of Pharmacy (19th ed.) ed. A. R. Gennaro, Mack Publishing Company, Easton, Pa. 1995. Typically, an appropriate amount of a pharmaceutically-acceptable salt is used in the formulation to render the formulation isotonic. Examples of the pharmaceutically-acceptable carrier include, but are not limited to, saline, Ringer's solution and dextrose solution. The pH of the solution is preferably from about 5 to about 8.5, and more preferably from about 7.8 to about 8.2. Further carriers include sustained release preparations such as semipermeable matrices of solid hydrophobic polymers containing the antibody, which matrices are in the form of shaped articles, e.g., films, liposomes or microparticles. It will be apparent to those persons skilled in the art that certain carriers may be more preferable depending upon, for instance, the route of administration and concentration of composition being administered.

Pharmaceutical carriers are known to those skilled in the art. These most typically would be standard carriers for administration of drugs to humans, including solutions such as sterile water, saline, and buffered solutions at physiological pH. Other compounds will be administered according to standard procedures used by those skilled in the art.

Pharmaceutical compositions may include carriers, thickeners, diluents, buffers, preservatives, surface active agents and the like in addition to the molecule of choice. Pharmaceutical compositions may also include one or more active ingredients such as antimicrobial agents, antiinflammatory agents, anesthetics, and the like.

The terms "effective amount" and "effective dosage" are used interchangeably. The term "effective amount" is defined as any amount necessary to produce a desired physiologic response. Effective amounts and schedules for administering the compositions may be determined empirically, and making such determinations is within the skill in the art. The dosage ranges for the administration of the compositions are those large enough to produce the desired effect in which the symptoms of the disorder are affected. The dosage should not be so large as to cause adverse side effects, such as unwanted cross-reactions, anaphylactic reactions, and the like. Generally, the dosage will vary with the age, condition, sex and extent of the disease in the patient, route of administration, or whether other drugs are included in the regimen, and can be determined by one of skill in the art. The dosage can be adjusted by the individual physician in the event of any counterindications. Dosage can vary, and can be administered in one or more dose administrations daily, for one or several days. Guidance can be found in the literature for appropriate dosages for given classes of pharmaceutical products.

As used throughout, by a "subject" is meant an individual. Thus, the "subject" can include domesticated animals, such as cats, dogs, etc., livestock (e.g., cattle, horses, pigs, sheep, goats, etc.), laboratory animals (e.g., mouse, rabbit, rat, guinea pig, etc.) and birds. Preferably, the subject is a mammal such as a primate, and, more preferably, a human.

"Alkalinizing" is defined as providing an active agent in an alkaline solution. "Alkaline" is defined as causing to have a pH of about 7.7-8.1, more preferably a pH of 7.8-7.9.

"Epithelial $Ca^{2+}$ entry channels" are defined as calcium-permeable, non-selective cation channels that are modified by extracellular ligands and small molecules. Examples of epithelial $Ca^{2+}$ entry channels include, but are not limited to, P2X purinergic receptor $Ca^{2+}$ entry channels, transient receptor potential (TRP) $Ca^{2+}$ entry channels, store-operated $Ca^{2+}$ (SOC) entry channels, calcium release activated channels (ICRAC), and CAT-1 $Ca^{2+}$ entry channels. Transient receptor potential channels are molecular substrates of receptor-mediated cation entry. TRP $Ca^{2+}$ entry channels are stimulated by ER store depletion, as well as by alkaline extracellular pH, for example. The epithelial polarity can be apical and basolateral.

Store operated calcium (SOC) entry channels and calcium release activated channels (ICRAC) are stimulated by ER depletion, for example. A major route for calcium influx is via the store-operated pathway in which the emptying of the endoplasmic reticular calcium stores activates calcium channels in the plasma membrane. CaT calcium entry channels have an apical epithelial polarity. They are related to the TRP family, but their expression is restricted to epithelia mainly from the gastrointestinal tract and kidney. Members of this family include, but are not limited to, CaT-1, CaT-2, and ECaC. They also contribute to store-operated calcium entry but limited to epithelial cells.

"P2X receptors" are defined as extracellular ATP-gated calcium-permeable, non-selective cation channels that are modulated by extracellular ligands and small molecules. By way of example, P2X receptors include subtypes such as P2X1, P2X2, P2X3, P2X4, P2X5, P2X6, and P2X7 are P2X receptors. They are referred to as "receptors" as well as "receptor channels" in the art.

Extracellular ATP-gated P2X purinergic receptor channels (P2XRs) are nucleotide receptors that also function as calcium ($Ca^{2+}$)-permeable, non-selective cation channels. At least nine subtypes have been cloned in mammals. Airway epithelial cells express mRNA for many P2XR subtypes; however, P2X4 appears the most abundant epithelial P2XR mRNA and protein. P2X4 receptors are poorly desensitizing or inactivating subtypes whose activity is sustained upon binding agonist. P2XRs possess a large extracellular domain, which accounts for approximately 70% of its molecular mass. Amiloride-sensitive epithelial sodium (Na+) channels (ENaC) and their relatives in mammalian, *Drosophila* and *C. elegans* neurons also share this extracellular domain. Therefore, this large domain exposed to the airway lumen functions as a "sensor" within the receptor channel. Stimulation of $Ca^{2+}$-permeable P2XRs under optimal extracellular conditions leads to $Ca^{2+}$ entry from extracellular stores.

Zinc is an agonist for the epithelial P2XRs critical to our therapeutic strategies in respiratory and renal epithelial diseases and disorders. Zinc is an antagonist for the ENaC channels, which hyperabsorb sodium and can effect CF, renal hypertensive disorders such as PKD, Bartter's syndrome, Liddle's syndrome, and Gitelman's syndrome. Zinc in an aerosolized, nebulized, or instilled solution cam inhibit ENaC-mediated hyperabsorption of sodium in CF as well as zinc provided in higher concentrations as an oral drug that is absorbed and freely filtered in the kidney may inhibit ENaC-mediated sodium hyperabsorption that leads to hypertension (higher than normal blood pressure).

CFPAC-1 CF human pancreatic epithelial cells as well as CF (IB3-1) and non-CF (16HBE41o-) human airway epithelial cell models were used to identify P2X-specific mechanisms of triggering an increase in $Ca^{2+}$. Fura-2/AM-based imaging shows activation of P2X receptors increases cytosolic $Ca^{2+}$ by triggering a sustained rise in $Ca^{2+}$, allowing $Ca^{2+}$ influx from the extracellular space. The P2X4 receptor is the major epithelial subtype present in both cell lines. Thus, epithelial P2X receptors function as ATP-gated $Ca^{2+}$ entry channels in the plasma membrane and have utility as a target for pharmacotherapy in airway diseases.

Methods

The present invention includes a method of increasing cytosolic $Ca^{2+}$ levels in airway epithelial cells comprising contacting P2X receptors on the cell with an effective amount of $Zn^{2+}$ or other small molecules or ligands. The present invention can also include adding an effective amount of ATP. An "increase in intracellular $Ca^{2+}$ levels" is defined as 100-1000 nM above basal levels, more preferably as 250-500 nM above basal levels. An "increase in extracellular $Ca^{2+}$ levels" is defined as 1.5-3 mM above basal levels. An "effective amount of cytosolic $Zn^{2+}$" is defined as 10-100 μM, more preferably 20-40 µM. An "effective amount of ATP" is defined as 50-150 µM, more preferably 90-110 µM, more preferably 95-105 µM, or any amount in between.

The present invention further provides methods of treating cystic fibrosis and other airway diseases comprising using ligands and other small molecules useful in targeting epithelial P2X receptors on the luminal membrane of human airways. Such ligands and small molecules can include zinc, ATP, nucleotides, ivermectin, α, β-methylene-ATP (α, β-meATP), benzoyl-benzoyl-ATP (BzBzATP), ATPγS, AMPPNP, and other ligands identified by the screening methods described herein.

A variety of agents can be used in combination with small molecules or ligands targeting P2X receptors. Ivermectin, an anti-parasitic agent, potentiates P2X receptor channels, which are expressed in human airway epithelia. BzBzATP induces an increase in $Ca^{2+}$ flux in P2X receptor channels. Such agents are useful in combination with zinc or other small molecules to increase $Ca^{2+}$ influx. These agents are also useful alone to increase $Ca^{2+}$ influx. Effective amounts of ivermectin can range from 10-1000 µM, preferably from 50-150 µM. Effective amounts of BzBzATP can range from 10-1000 µM, preferably from 50-150 µM.

As used in the methods and compositions described herein, $Zn^{2+}$ can optimally be in the form of zinc chloride. Zinc can also be formulated as zinc sulfate, zinc nitrate, and zinc citrate, for example. The present invention also includes an embodiment wherein the P2X receptors are not contacted with zincum gluconium. "Zincum gluconium" is also known as "zinc gluconate trihydrate" in the art.

Manipulation of the extracellular solution or vehicle promotes a robust increase in $Ca^{2+}$ derived from extracellular stores that is sustained. Thus, the effectiveness of the methods taught herein can be augmented by changes in the extracellular solution or the vehicle comprising the $Zn^{2+}$ or other small molecule or ligand. For example, reduction in Na+ levels to less than 0.1 mM can be used. In one embodiment, the Na+ level can be effectively reduced by using an effective amount of amiloride, which inhibits the cells' absorption of Na+. An "effective amount of amiloride" is defined as 1-100 µM, more preferably 10-80 µM, more preferably 15-55 µM. In another embodiment, extracellular Na+ can be substituted with N-methyl-D-glucamine (NMDG), or a comparable agent.

Another embodiment of the invention comprises reducing the cell's extracellular $Mg^{2+}$ or administering the agent in a vehicle with low $Mg^{2+}$. By "reducing the cell's extracellular $Mg^{2+}$" is meant reducing the amount of $Mg^{2+}$ compared to a control cell. By a "vehicle low in $Mg^{2+}$" is meant a level lower than normal resting extracellular fluid. For example, reduction in $Mg^{2+}$ levels to less than 0.1 mM can be used. Also contemplated by the present invention is increasing the cell's extracellular $Ca^{2+}$ or administering the agent in a vehicle high in $Ca^{2+}$, whereby extracellular $Ca^{2+}$ or levels of calcium are 250-500 µM over basal levels.

Alkalinization to pH 7.8 to 7.9 of the extracellular solution or the vehicle also optimizes the effect. $Zn^{2+}$ potentiates the sustained increase in $Ca^{2+}$ as compared to that caused by ATP. Both $Zn^{2+}$ and ATP caused a sustained increase in cytosolic $Ca^{2+}$ derived from extracellular stores. When either $Zn^{2+}$ or ATP was removed, the response was reversible. Normalization of extracellular pH to 7.3 or vehicle caused a reduction of the $Zn^{2+}$ or ATP response, as did replenishment of Na+ levels. Acidification of the extracellular fluid or vehicle reduced ATP and $Zn^{2+}$ stimulation of sustained $Ca^{2+}$ entry from extracellular stores. Thus, ATP and $Zn^{2+}$ bind to separate sites in the extracellular domain of epithelial P2X receptors under precise chemical and ionic conditions to stimulate a profound and fully sustained increase in $Ca^{2+}$. This augmented the effect of zinc and ATP in epithelial cells; however, changing of the extracellular or solution pH may not be necessary for every cell model.

$Zn^{2+}$, under optimal chemical and ionic conditions, triggers a similar magnitude of sustained $Ca^{2+}$ increase derived from extracellular stores as ATP plus $Zn^{2+}$. This sustained increase in $Ca^{2+}$ is fully reversible. Zinc alone, or in combination with other agents described herein, stimulates sustained $Ca^{2+}$ entry and rescues Cl− permeability and regulatory volume decrease (RVD). Regulatory volume is the cell's ability to shrink or swell in response to the osmotic environment of the cell. Cells without CFTR do not regulate well and often die as a result. For example, in response to a hypotonic environment, normal cells conduct RVD, while those without CFTR are unable to regulate their size. Zinc, alone or in combination with other agents, was able to restore RVD function. Zinc and ATP were required to restore Cl− secretion across monolayers in vitro and nasal mucosa in vivo. Zinc, alone or in combination with other agents, also triggers an increase in $Ca^{2+}$ derived from intracellular $Ca^{2+}$ stores.

The present invention also includes a method of restoring Cl− transport and rescuing impaired cell volume regulation in subjects with airway disease, such as CF, comprising administering to the cell or subject an effective amount of $Zn^{2+}$. By "impaired cell volume" is meant an impairment in the regulation of cells in response to the osmotic conditions of the cellular environment. By "restoring Cl− transport" is meant restoring the Cl− transport to the level of that found in a control cell. By "rescuing impaired cell volume" is meant restoring cell volume to that of a control cell.

The present invention also includes a method of treating an airway disease in a subject, comprising contacting epithelial cells in the airways (e.g., nasal passages, nasopharynx, trachea, bronchi, bronchioles, and alveoli) of the subject with an effective amount of $Zn^{2+}$, or another small molecule or ligand. As disclosed above, manipulation of the extracellular solution or vehicle promotes a robust increase in $Ca^{2+}$ derived from extracellular stores that is fully sustained. Thus, the effectiveness of the methods taught herein can be augmented by changes in the extracellular solution or the vehicle comprising the $Zn^{2+}$ or other small molecule or ligand. Examples of manipulation of the extracellular solution is disclosed above.

The present invention also includes a contacting step being performed with an agonist-containing inhalant, nebulization, aerosol, or instillant. An "inhalant" is defined as something used in or for inhaling; something that is inhaled, as in a medicine. "Nebulization" is defined as converting a liquid to a fine spray; atomizing. "Aerosol" is defined as "a gaseous suspension of fine particles." "Instillant" is defined as a means of instilling a fine substance over a period of time. A solution-based therapy bearing zinc as the therapeutic agonist is an effective strategy to treat CF, asthma, and common cold in the nasal passages and the airways, because the abnormalities, infections and inflammation are found in those passages and airways, especially at the level of the airways epithelium.

The present invention also includes a method of treating airway disease in a subject, comprising contacting the subject's airway epithelial cells with an alkaline composition comprising an effective amount of $Zn^{2+}$, or another small molecule or ligand, in a saline solution. Optimally, the saline solution has low levels of Na+, is enriched with $Ca^{2+}$, and modified to an alkaline pH of about 7.9. "Saline solution" is defined as "a solution that is isotonic with blood." By way of example, Ringer's solution may be used, which is a solution of recently boiled distilled water containing 8.6 gm sodium chloride, 0.3 gm potassium chloride, and 0.33 gram calcium chloride per liter—comparable concentrations compared to physiologic fluids. By "enriched for $Ca^{2+}$" is meant 1.5-3 mM above basal levels.

As disclosed above, manipulation of the extracellular solution or vehicle promotes a robust increase in $Ca^{2+}$ derived from extracellular stores that is sustained. Thus, the effectiveness of the methods taught herein can be augmented by changes in the extracellular solution or the vehicle comprising the $Zn^{2+}$ or other small molecule or ligand. Examples of manipulation of the extracellular solution is disclosed above.

The methods of the present invention are useful in various diseases, infections, and conditions. Zinc is anti-inflammatory and is protective in asthma and other airway diseases or ailments, including common cold. Zinc, given in the solution described herein, also has unique applications to be anti-inflammatory by entering mammalian cells and inhibiting inflammatory signaling cascades with the cell (by blocking induction of the key transcription factor NFkappaB) and by affecting the growth and/or metabolism of a wide variety of bacterial pathogens through competitive inhibition of metal scavenging pathways essential for bacterial pathogen survival and growth in the host.

Activation of P2X receptor $Ca^{2+}$ entry channels and the use of zinc as a therapeutic ligand have multiple possible therapeutic benefits. Zinc and nucleotides augment $Ca^{2+}$ entry via P2X receptors (North Physiol. Rev. 82: 1013-1067, 2002), an effect that rescues Cl– secretion in CF. Either by increasing cell $Ca^{2+}$ or by inhibiting ENaC channels directly, zinc inhibits Na+ hyperabsorption in CF.

Disclosed are methods of inhibiting inflammation in a subject comprising administering to the subject an effective amount of $Zn^{2+}$ or other small molecules or ligands. Also disclosed are methods of inhibiting NFkappaB by contacting the NFkappaB with an effective amount of $Zn^{2+}$. In addition to ion transport dysregulation, CF has profound inflammatory and microbiological components (Davis et al. Am. J. Respir. Crit. Care Med. 154: 1229-1256, 1996). Attenuation of airway inflammation as well as prevention of recurrent and tenacious bacterial infection by Pseudomonas aeruginosa and other bacterial pathogens is more critical than correcting salt and water transport in CF. Fortunately, in addition to correction of NaCl and water transport in CF airways epithelia, homeopathic and other zinc formulations inhibit the activity of the key inflammatory transcription factor, NFkappaB, in airway epithelial cells and they are bacteriastatic for both the non-mucoid and mucoid forms of *Pseudomonas aeruginosa*. Importantly, the latter form is antibiotic-resistant, illustrating the important benefit of growth inhibition of this mutated form by zinc.

Disclosed are methods of inhibiting bacterial growth comprising contacting bacteria with an effective amount of $Zn^{2+}$ or other therapeutic ligands or small molecules. Also disclosed are methods of killing bacteria comprising treating the bacteria with an effective amount of $Zn^{2+}$ or other small molecules or ligands. Zinc inhibits metal scavenging pathways important for growth and survival of *Pseudomonas aeruginosa* and other bacterial pathogens in vitro or in the host. Other bacterial pathogens (like *Streptomyces mutans, Escherichia coli, Streptococcus pneumoniae, bacillus subtilis*, and *bacillus anthracis*) use a similar or different metal scavenging pathway that zinc can competitively inhibit. In one embodiment, zinc formulations inhibit the growth (are bacteristatic) at lower concentrations and are bactericidal at higher concentrations for avirulent strains. For example, the zinc formulation can be bacteriastatic in the range of 0.01 to 1 mM, or 0.1 to 0.5 mM, and bactericidal in the range of 1.0 to 10 mM, or 5 to 50 mM. Examples of bacteria that can be treated by this formulation include, but are not limited, to *E. coli, Bacillus anthracis* (anthrax), and *Bacillus subtilis* in addition to non-mucoid and mucoid *Pseudomonas*. The effects of zinc have been similar in terms of bacteriastatic and bactericidal effects on all bacterial pathogens.

Disclosed are methods of inhibiting viral growth comprising treating a virus with an effective amount of $Zn^{2+}$. Zinc has also been reported to be an anti-apoptotic and anti-oxidant. Hence zinc is a therapeutic for asthma and reactive airways disease. It appears that zinc binds to the viral capsid proteins of viruses that cause common cold symptoms. Zinc, as an anti-inflammatory, anti-viral, and anti-bacterial, added to the nasal cavity and airways in a nasal spray or as an aerosolized or nebulized solution can have therapeutic benefit in these airway diseases in addition to CF. One example of a dosage range for zinc to be used as an antiviral is 0.01 to 100 mM, or 0.1 to 50 mM, or 1.0 to 10 mM.

Also disclosed are methods of treating polycystic kidney disease comprising administering to the subject an effective amount of $Zn^{2+}$. PKD arises in two genetic forms, an autosomal dominant form (ADPKD) and an autosomal recessive form (ARPKD) (Grantham Curr. Opin. Nephrol. Hypertens. 10: 533-542, 2001, Wilson Am. J. Physiol. 272: F434-F442, 1997). Both forms of the disease affect the growth of renal epithelial cells, but in a non-cancerous manner. The cells revert back to an undifferentiated state, have an increased proliferation rate, and do not polarize as readily as a normal epithelial cell. In both forms of PKD, this changes the morphology of the epithelial cell and the architecture of the normal tubules of the functional unit of the kidney, called the renal nephron. In ADPKD, each end of a given tubule pinches off, creating a fluid-filled cyst encapsulated by a single monolayer of cystic epithelial cells. In ARPKD, the tubules only become cysts in end-stage renal disease; however, they do become profoundly dilated. Moreover, in ARPKD, this tubule dilation is more restricted to the distal nephron; whereas, in ADPKD, cysts form in all portions of the nephron, contributing to the heterogeneity of this form of the disease.

A unifying feature of ARPKD and ADPKD explains multiple manifestations of the disease. Most protein products of both forms of the human disease as well as in mouse models of PKD localize to a central cilium, known as the "monocilium" or "apical central or core cilium" on epithelia from the kidney and elsewhere (PKD also has phenotypes in pancreas, liver, and other foci within brain and the vasculature that can cause cysts and aneurysm) (Sutters and Germino J. Lab. Clin. Med. 141: 91-101, 2003). The presence and proper formation of this monocilium has been linked to development of the organism, development of epithelial cell polarity, development of normal tissue architecture, and normal transepithelial ion transport. PKD gene products as well as the cilium itself have been implicated in $Ca^{2+}$ entry from extracellular stores. Loss of this $Ca^{2+}$ signal due to mutation of a key ciliary protein or loss of the cilia altogether is central to both forms of PKD (Praetorius and Spring J. Membr. Biol. 184: 71-79, 2001). Any alternative and cilium-independent $Ca^{2+}$ entry. channel or mechanism could provide a therapeutic target for this kidney disease. An effective amount of zinc can be in the range of 1 to 1000 mM or in the range of 50-100 mM.

In ARPKD, the majority of patients develop renal-derived hypertension (Guay-Woodford and Desmond Pediatrics 111: 1072-1080, 2003). Absorption of sodium (Na+) by human cells is heightened in ARPKD, as it is in many renal hypertensive disorders including salt-sensitive hypertension, Bartter's syndrome, Liddle's syndrome, and Gitelman's syndrome (Schafer Am. J. Physiol. 283: F221-F225, 2002; Rohatgi et al. J. Am. Soc. Neph. 14: 827-836, 2003). Raising cell $Ca^{2+}$ inhibits Na+ absorption through the epithelial Na+ channels (ENaCs) as well as through other mechanisms. Zinc, the agonist for P2X receptor $Ca^{2+}$ entry channels, also binds to ENaC channels directly and inhibits them (Amuzescu et al. Pflugers Arch. 446: 69-77, 2003, Sheng et al. J. Biol. Chem. 277: 50098-50111, 2002). As such, therapeutic approaches extend beyond both genetic forms of PKD into the realm of the many renal hypertensive disorders or syndromes listed above.

Disclosed are methods of treating neuro and endocrine disorders comprising administering to the subject an effective amount of $Zn^{2+}$. Hormones, agonists, neurotransmitters and other released substances are packaged within secretory vesicles or granules within a cell where they lie in wait for the proper stimulus to trigger them to fuse with the plasma membrane to release the substance packaged within (Barg Pharmacol. Toxicol. 92: 3-13, 2003). The process of fusion and release is called exocytosis. The stimulus can be the binding of another agonist, a change in membrane voltage, or a mechanical insult such as flow, pressure, or touch. Whatever the stimulus to the neuroendocrine cell, an increase in cell $Ca^{2+}$ occurs most often derived from $Ca^{2+}$ entry from extracellular stores via $Ca^{2+}$ entry channels (Ackerman and Clapham N. Engl. J. Med. 336: 1575-1586, 1997). In both forms of diabetes and in any disorders where there is a loss of secretion or a failure to release agonist (insulin released from pancreatic p cells in the case of diabetes), this $Ca^{2+}$ entry, its stimulus, or steps within the cellular mechanisms in between the stimulus and the $Ca^{2+}$ entry are impaired. Such is true in diabetes.

A normal pancreatic β cell responds to glucose after a meal by secreting insulin to trigger the liver, skeletal muscle, and adipocytes to sequester and store that glucose. In diabetes mellitus and in early type I diabetes before the degeneration of the β cells themselves, rising levels of glucose fail to translate into insulin secretion by the β cell due to defects in one or more of the steps within a unique cellular mechanism (see below in Model Figures). If normal, ultimately a rise in plasma and cell glucose depolarizes the β cell membrane voltage, opens voltage-dependent $Ca^{2+}$ entry channels, causes cell $Ca^{2+}$ to rise, and triggers fusion and release of insulin granules. In diabetes, insulin secretion is lost. The therapeutic targets of the invention again are "alternative" $Ca^{2+}$ entry channels and mechanisms that are independent of glucose or changes in membrane voltage and investigate the use of existing or new ligands for these said "alternative" $Ca^{2+}$ entry channels on the pancreatic β cell or any other endocrine cell involved in another "loss of function" endocrine disorder.

Diabetes is one of many syndromes, diseases, or disorders broadly defined as "failure to secrete" diseases. The targets, ligands, calcium entry solution, etc. described herein can be applied to calcium entry disorders (like those described in Alzheimer's disease)(Leissring et al. J. Cell Biol. 149: 793-798, 2000, Ito et al. Proc. Natl. Acad. Sci. USA 91: 534-538, 1994) or in neural, neuroendocrine, or endocrine disorders where there is failure to secrete agonist (neurotransmitter, hormone, ligand, etc.) in sufficient quantities to be biologically effective http://members.aol.com/henryhbk/endocrine.html, http://www.upei.ca/~cidd/Diseases/endocrine%20diseases/endocrine%20disorders%20list.htm, http://homepage.psy.utexas.edu/HomePage/Class/Psy308/Humm/lectures/05-07Neurotransmitters&Drugs). Because secretion of a vesicle or granule containing a physiological endocrine agonist is linked directly to an increase in cell calcium (usually derived from calcium entry from the extracellular space), these targets and ligands are applicable to Type 2 diabetes (diabetes mellitus). However, these targets and ligands are also applicable to a host of neural, neuroendocrine and endocrine diseases, like diabetes, which include, but are not limited to, growth hormone deficiency (pituitary dwarfism), adrenal insufficiency syndromes (Addison's disease), amyotrophic lateral sclerosis (ALS or Lou Gehrig's disease (http://members.aol.com/henryhbk/endocrine.html, http://www.upei.ca/~cidd/Diseases/endocrine%20diseases/endocrine%20disorders%20list.htm, http://homepage.psy.utexas.edu/HomePage/Class/Psy308/Humm/lectures/05-07Neurotransmitters&Drugs), and Alzheimer's disease (Leissring et al. J. Cell Biol. 149: 793-798, 2000, Ito et al. Proc. Natl. Acad. Sci. USA 91: 534-538, 1994).

The invention also provides methods of identifying an agonist of airway epithelial P2X receptors comprising the steps of contacting an airway epithelial cell with an agent to be tested and detecting an increase in cystolic $Ca^{2+}$. An increase in cystolic $Ca^{2+}$ indicates a P2X agonist. As described above, the detection method is enhanced by manipulating the extracellular fluid. Thus, agents that would not otherwise be identified as P2X receptors can be detected with optimizing conditions in pH and ionic composition.

Another embodiment includes methods of treatment for epithelial disorders of lung and kidney as well as endocrine and neuroendocrine disorders. The contacting and opening of P2XR and any other calcium entry channels or mechanisms rescues "failure to secrete agonist" disorders such as diabetes, Addison's disease, pituitary insufficiency disorders (dwarfism, etc.), Alzheimer's disease, and ALS or Lou Gehrig's disease. Zinc, given orally as a capsule, as a drink, or in a nutritional supplement, or any other calcium entry ligand rescues agonist secretion in these or other endocrine or neuroendocrine disorders.

The invention provides methods of screening for an epithelial $Ca^{2+}$ entry channel agonist, comprising contacting an epithelial cell with a test compound; detecting calcium levels in the epithelial cell; and screening for a sustained elevation in calcium as compared to a control level, indicating an airway epithelial $Ca^{2+}$ entry channel agonist. The epithelial cell is selected from the group consisting of an airway epithelial cell and a gastrointestinal epithelial cell.

Screening optionally takes place in multi-well plates. Multi-well plates are standard in the art and come in a variety of sizes and shapes. For example, the multi-well plate can be 96 or 384 well plates. Such screening assays can be automated or further modified for high throughput analysis.

A "sustained elevation in calcium" is defined as an increase in intracellular calcium levels greater than 50 nM above basal levels. The sustained elevation in intracellular calcium can also be greater than 100 nM above basal levels. The sustained elevation in intracellular calcium can also be greater than 200 nM above basal levels. The time defined as "sustained" can be greater than 5 minutes, greater than 10 minutes, or greater than 20 minutes, for example.

The invention also provides methods of screening for an epithelial $Ca^{2+}$ entry channel agonist, comprising contacting a first epithelial cell with more than one test compound; detecting calcium levels in the first epithelial cell; selecting each of test compounds in the group that contacted the first epithelial cell, wherein the first epithelial cell showed a sustained elevation in calcium; contacting a second epithelial cell with one test compound from the step of selecting each of the test compounds; and detecting calcium levels in the second epithelial cell, a sustained elevation in calcium as compared to a control level, indicating an epithelial $Ca^{2+}$ entry channel agonist.

Also contemplated are agents identified by the screening methods described herein, as well as methods of making those agents. An example of a method of malting an agent includes identifying the agent using the methods provided herein, and manufacturing the agent.

Also provided are methods of screening for a $Ca^{2+}$ entry channel agonist, comprising contacting a test compound with a cell that expresses a heterologous nucleic acid that encodes a $Ca^{2+}$ entry channel; and detecting calcium levels in the cell; a sustained elevation in calcium as compared to a control level, indicating a $Ca^{2+}$ entry channel agonist. Preferably, the cell is a cell that lacks the receptor prior to introduction of the heterologous nucleic acid. The cell can be transiently transfected with the heterologous nucleic acid. By "heterologous nucleic acid" is meant any exogenous nucleic acid inserted into a vector or other means of transfer for transfer into a cell, tissue or organism. The nucleic acid can encode a polypeptide or protein or an antisense RNA, for example. The nucleic acid can be functionally linked to a promoter. By "functionally linked" is meant such that the promoter can promote expression of the heterologous nucleic acid, as is known in the art, such as appropriate orientation of the promoter relative to the heterologous nucleic acid. Furthermore, the heterologous nucleic acid preferably has all appropriate sequences for expression of the nucleic acid, as known in the art, to functionally encode, i.e., allow the nucleic acid to be expressed. The nucleic acid can include, for example, expression control sequences, such as an enhancer, and necessary information processing sites, such as ribosome binding sites, RNA splice sites, polyadenylation sites, and transcriptional terminator sequences.

The heterologous nucleic acid introduced into the cell can include, for example, one or more nucleic acids encoding one or more subparts of the $Ca^{2+}$ channel. For example, four different subparts of a P2X receptor could be encoded in four different nucleic acids or in three, two, or one nucleic acids. In various embodiments, specific agonists could be tested using different subparts for the channel. These assays would thus identify agonists for different subtypes of P2X channels (e.g., P2X6, P2X5, P2X4, etc.) that complex together to form the fully functional receptor channel present in native epithelial cells.

The invention also provides methods of screening for an epithelial $Ca^{2+}$ entry channel agonist, further comprising screening for reversibility of response by removing the agonist during the assay and testing $Ca^{2+}$ entry after the agonist is removed. In a preferred embodiment, the agonist identified by the methods described herein is a reversible agonist.

The invention also provides methods of screening for an epithelial $Ca^{2+}$ entry channel agonist, further comprising screening for dependence upon extracellular $Ca^{2+}$ by performing the contacting step in a solution devoid of extracellular $Ca^{2+}$.

Also contemplated are methods for screening for an epithelial $Ca^{2+}$ entry channel agonist by using a Fura-2 quenching experiments in which Fura-2 fluorescence is measured at a $Ca^{2+}$-insensitive wavelength (at or about 359 nm) and manganese, $Mn^{2+}$, is added outside the cells. $Mn^{2+}$ enters like $Ca^{2+}$ entry in this screening assay but it inhibits or quenches Fura-2 fluorescence. This shows that a ligand promotes $Ca^{2+}$ entry, but by using $Mn^{2+}$ as the transported substrate.

There are several known $Ca^{2+}$ entry channels. The $Ca^{2+}$ entry channel can be a P2X purinergic receptor $Ca^{2+}$ entry channel, a transient receptor potential (TRP) $Ca^{2+}$ entry channel, a store-operated $Ca^{2+}$ (SOC) entry channel, a calcium release activated channel (ICRAC), or a CaT $Ca^{2+}$ entry channel.

The airway epithelial cell can originate from a cystic fibrosis airway epithelial cell line, such as an IB3-1 human CF bronchial epithelial cell line, a CFBE41o- human bronchial epithelial cell line, and a CFPAC-1 cell line. In methods of screening for epithelial $Ca^{2+}$ entry channel agonists, wherein the epithelial cell to be tested is a gastrointestinal epithielial cell, the gastrointestinal epithelial cell is a cystic fibrosis pancreatic epithelial cell. More specifically, the cystic fibrosis gastrointestinal epithelial cell can be a CFPAC CF human pancreatic epithelial cell line.

Calcium levels and changes in calcium levels can be detected using a calcium indicator such as the cell-permeable methyl ester form of Fura-2, which is Fura-2/AM. In another example, a fluorescence plate reader is used that detects a single wavelength, such as $Ca^{2+}$ indicator dyes Fluo 3, Quin 2, Indo-1 and Indo-4.

A decrease in the extracellular solution promotes a robust increase in $Ca^{2+}$ derived from extracellular stores that is fully sustained. Thus, the effectiveness of the methods taught herein can be augmented by changes in the extracellular solution. For example, a "low Na+solution" is defined as a reduction in Na+ levels to less than 0.1 mM. The airway epithelial cell can also be in a 0 Na+ solution. Various embodiments of the screening methods taught herein include contacting the epithelial cell with the agent to be tested, wherein the epithelial cell is at a low or 0 Na+ level.

The screening methods described herein can optimally comprise contacting the cell, wherein the cell is in a solution with low $Mg^{2+}$. "Low $Mg^{2+}$" is defined as a reduction in $Mg^{2+}$ levels to less than 0.1 mM. The epithelial cell can also be in a 0 $Mg^{2+}$ solution.

Also contemplated is contacting the epithelial cell, wherein the cell is in a solution enriched for extracellular $Ca^{2+}$. Calcium is normally present in the amount of 1-1.5 mM in extracellular solution, Ringer's solution, and plasma. "Enriched for extracellular $Ca^{2+}$" is defined as levels of calcium about twice that of basal levels, or about 2.5 to about 3.5 mM.

Optionally, the compound being screened can augment the effects of other compounds such as ATP, zinc, or ionomycin, for example. In this case, the 10 compound being screened can be tested in the presence of another compound that stimulates the calcium entry channel. For example, the epithelial cell can be in a solution containing an effective amount of ATP. An "effective amount of ATP" is defined as about 1 to about 500 mM of ATP or 10 to about 200 mM of ATP. The solution of the cell can also contain an effective amount of zinc. An "effective amount of zinc" is defined as about 1 to about 100 mM of zinc or about 10 to about 50 mM of zinc.

Alkalinization of the extracellular solution of the cell optimizes the effect of screening for an agonist. Thus the contacting step can be performed with the epithelial cell present in an alkaline solution. The alkaline solution can have a pH of about 7.6-8.0, or a pH of about 7.8-7.9, or a pH of about 7.8.

The above is generally applicable for measuring sustained levels of calcium whether by fluorescence, luminescent or other detection techniques. The invention has particular application to high throughput screening and whole cell functional assays for compounds with biological activity. In the most general premise, one can use any type of compound that can affect the calcium entry channel.

The process is also applicable for screening compounds with biological activity characterized by rapid and transient changes in cellular calcium. Examples include the evaluation of receptor agonists that elicit changes in cellular calcium concentration. Intracellular reporters (calcium indicators) such as the calcium-sensitive bioluminescent acquorin protein or fluorescent proteins or synthetic probes such as the fluorescent calcium dyes (Fura 2, Fluo 3, Quin 2, Indo-1, and Indo-2, for example) can be used.

Also provided are protocols that delay the calcium response as measured by calcium-sensitive reporters. For this purpose, a cell permeable calcium chelator, for example, BAPTA-AM is used. These protocols are useful for both fluorescent and luminescent calcium-sensitive reporters. For example, the calcium signal caused by activation of a ligand-gated calcium channel in an aequorin-expressing cell line can be delayed by several seconds and the response extended for several minutes with BAPTA without significantly reducing the total signal output. This means that the fast and transient calcium signals which previously required instrumentation that simultaneously injects and measures these signal can now be performed by a host of other instruments. The methods of this invention can be advantageously applied to whole-cell functional assays of a calcium ion channel and a G-protein-coupled receptor. In both cases the delay of the fluorescent or luminescence signals are sufficient enough for simultaneous addition of agonist to multiple wells by an external liquid handling system followed by rapid transfer into fluorescent or luminescence imaging systems, for example, the PE BIOSYSTEMS NORTHSTAR™ HTS Workstation.

Glow luminescence assays have been readily adopted into high throughput screening facilities because of their intrinsically high sensitivities and long-lived signals. The signals for chemiluminescence systems such as luciferase and beta-galactosidase reporter genes or for alkaline phosphatase conjugates are often stable for several hours.

A flash luminescence assay system can optionally be used. An example of a flash luminescence-based functional assay is the measurement of calcium signaling pathways in cells containing the bioluminescent protein, aequorin (Button, D Cell Calcium 14, 663-671). Aequorin is a calcium-dependent enzyme that produces light (466 nm) upon oxidation of coelenterazine. Typically, aequorin-based functional cellular assays for G-protein-coupled receptors (GPCRs) or ligand-gated calcium channels are initiated by addition of agonist which increases the intracellular concentration of calcium from intracellular stores or intake of external calcium. The increase of intracellular calcium concentration initiates the reaction of aequorin with its substrate giving rise to a rapid luminescence signal. Therefore the detection of these signals must be made simultaneously upon addition of the agonist. For assays performed in microtiter plates, this requires a luminometer that has simultaneous liquid injection and sample detection capabilities.

Using a chelator to delay the calcium kinetics enables high throughput screening assays to take place. (See U.S. Pat. No. 6,514,709 which is incorporated herein by reference in its entirety for use of chelators for delaying calcium kinetics). With the introduction of FLIPR (MOLECULAR DEVICES) (Sullivan, E., Calcium Signaling Protocols 114, 125-133), it is possible to record fluorescence from 96 and 384-well plates with simultaneous liquid addition.

Several commercial luminescence and fluorescence detectors are available that can simultaneously inject liquid into single or multiple wells such as the WALLAC VICTOR2 (single well), MICROBETA RTM JET (six wells), or AURORA VIPR (eight wells). Typically, these instruments require 12 to 96 minutes to read a 96-well plate in flash luminescence or fluorescence mode (1 min/well). An alternative method is to inject the stimulant/agonist into all sample wells at the same time and measure the luminescence in the whole plate by imaging with a CCD camera, similar to the way that calcium responses are read by calcium-sensitive fluorescent dyes in the FLIPR or FLIPR-384 instruments. Other luminescence or fluorescence imaging systems include LEADSEEKER from AMERSHAM, the WALLAC VIEWLUX™ ultraHTS microplate imager, and the MOLECULAR DEVICES CLIPR imager.

PE BIOSYSTEMS TROPIX produces a CCD-based luminometer, the NORTHSTAR™ HTS Workstation. This instrument is able to rapidly dispense liquid into 96-well or 384-well microtiter plates by an external 8 or 16-head dispenser and then can quickly transfer the plate to a CCD camera that images the whole plate. The total time for dispensing liquid into a plate and transferring it into the reader is about 10 seconds.

Compositions

The present invention also encompasses a composition comprising zinc and a saline solution. The present invention includes an optimized saline vehicle in which zinc, ATP, or other small molecules or ligands increase $Ca^{2+}$ derived from extracellular stores in a sustained manner and restore transepithelial secretory Cl– transport to airway epithelia in vitro and in vivo that is sustained, reversible, and reproducible (e.g., epithelial P2XRs do not desensitize or inactivate). Luminally expressed epithelial P2XRs are a therapeutic target that are normally expressed on cilia and the airway surface epithelium and restore normal Cl– secretory function.

The present invention also includes a composition comprising zinc and a saline solution, wherein said saline solution has low levels of Na+, is enriched with $Ca^{2+}$, and modified to an alkaline pH of about 7.9. "Low levels of Na+" is defined as "sodium free" or having less than 0.1 mM Na+. The saline vehicle may be modified in order to obtain a therapeutic effect. Removal of Na+ benefits P2XR $Ca^{2+}$ entry channel function, as it may for other $Ca^{2+}$ entry channels.

The present invention also includes a nasal spray comprising a composition comprising zinc or other small molecules or ligands and a saline solution. Nasal 20 sprays are well known in the art and are used to combat sinusitis and allergies, among other disorders or diseases of the nasal passages. Nasal sprays are also known in the art as being an effective carrier for various medicaments, which may be delivered to the blood stream via the small capillaries found in the nasal passages.

The present invention also includes a nebulizer comprising a composition comprising zinc or other small molecules or ligands and a saline solution. Nebulizers are well known in the art. Typically, a nebulizer functions as a continuous aerosol generator. A liquid medication is added to a reservoir and a gas flow converts the liquid to an aerosol when in operation.

The present invention also includes an aerosol inhaler comprising a composition comprising zinc and a saline solution. There are a number of different devices for delivering asthma medication into the lungs. One of the most commonly used is the aerosol inhaler or puffer. This delivers a set dose of medication by using a chemical propellant, e.g. chlorofluorocarbon (CFC) or hydrofluroalkane (HFA), to force the medication out of the inhaler.

Also, provided are kits for performing the methods of the present invention. For example, the kit may contain a composition comprising $Zn^{2+}$ or other small molecules or ligands, and a saline solution, and optionally may contain a nebulizer, aerosol, nasal spray, inhaler, or instiller. The kit may also contain instructions for use as well as packaging materials.

The present invention is more particularly described in the following examples, which are intended as illustrative only since numerous modifications and variations therein will be apparent to those skilled in the art.

Although the present process has been described with reference to specific details of certain embodiments thereof, it is not intended that such details should be regarded as limitations upon the scope of the invention except as and to the extent that they are included in the accompanying claims.

EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

Example 1

Cell Cultures

IB3-1 cells derive from airway epithelia of a CF patient carrying two different mutations of the CFIR gene, the most common trafficking mutation (ΔF508) and a premature stop codon mutation (W1282X). 16HBE41o- are non-CF or normal airway epithelial cells, which express CFTR at the plasma membrane. The cells were grown on uncoated tissue-culture flasks in 5% CO2 incubator at 37° C. IB3-1 cells were cultured in LHC-8 (Biofluids, Rockville, Md., USA) medium supplemented with 5% fetal bovine serum (Gibco BRL, Grand Island, N.Y., USA), 100 U/ml of penicillin-streptomycin (GEBCO BRL), 1× L-glutamine (Gibco BRL) and 1.25 μg/ml of Fungizone (Gibco BRL). 16HBE41o-cells were cultured in MEM (GIBCO BRL) medium supplemented with 10% fetal bovine serum and 100 U/ml penicillin-streptomycin. When cells reached confluency, they were washed twice with $Ca^{2+}/Mg^{2+}$-free PBS. The cells were then suspended using typsin/EDTA solution and plated on diluted Vitrogen-coated (collagen types I and IV diluted 1:15 in Dulbeccos phosphate buffered saline) glass coverslips. For $[Ca^2]_i$ measurements, cells were used 48-72 hours after plating.

CFPAC-1 cells are a human pancreatic epithelial cell line derived from a CF patient that was homozygous for the most common trafficking mutation (ΔF508). Iscove's minimum essential medium is the basal medium for these cells, all other constituents the same.

INS-1 cells are a rat pancreatic β cell line derived from the islets of Langarhans in the endocrine pancreas. They are among the few β cell models that maintain the ability to secrete insulin. These cells are grown in RPMI1640 supplemented with 11 mM glucose, 2 mercaptoethanol, sodium pyruvate, HEPES, and L-glutamine.

Example 2

Transgenic Mouse Models

Three different CF mouse models generated by different methods are used for in vivo nasal potential difference measurements. They are also used to test the effects of aerosolized and nebulized zinc and other ligands as well as orally derived zinc and other ligands. The first is a CF knockout mouse in which the CF gene has been deleted and the CF gene product, CFTR, is absent from every tissue and cell. The second is a bitransgenic CF knockout mouse in which the lung and airways are still null for CFTR and the CF gene but where the wild-type CFTR gene has been re-inserted into the intestines of the mice to overcome intestinal and nutritional problems. These mice are referred to as the bitransgenic or Cincinnati mice. The third is a CF mouse engineered to express the most common human mutation, the ΔF508-CFTR trafficking mutation, in all tissues and cells. Wild-type and heterozygous controls (with two or one wild-type CFTR allele are/is present) are bred along with the homozygous animals and are studied in parallel.

Example 3

Fura-2/AM Fluorescence-Based Imaging of $Ca^{2+}$ of Airway and Kidney Epithelial Cells and in Rat Pancreatic β Cells Cytosolic $Ca^{2+}$ concentration was measured with dual excitation wavelength fluorescence microscopy (Deltascan, Photon Technologies, Princeton, N.J.) after cells were loaded with the permeant form of the fluorescence dye, Fura-2-acetoxymethyl ester (Fura-2-AM; Teflabs, Austin, Tex., USA). Fura-2 fluorescence was measured at an emission wavelength of 510 nm in response to excitation wavelength of 340 nm and 380 nm, alternated at a rate of 50 Hz by a computer-controlled chopper assembly. Ratios (340 nm/380 nm) were calculated at a rate of points/s using PTI software. Cells were incubated in Dulbecco's phosphate buffered saline containing 2 mM CaCl2 and 1 mM MgCl2 in the presence of 5 μM Fura2-AM and 1 mg/ml Pluronic F-127 dissolved in DMSO for 120 min to allow loading of the dye into the cells. After loading, coverslips were rinsed at least for 10 min in Dulbecco's phosphate buffered saline to remove extracellular Fura 2-AM and the surfactant, and were positioned in the cuvette at a 45° angle from the excitation light. Two glass capillary tubes were inserted into the top of the cuvette out of the patch of the excitation light. One tube was extended to the bottom of the cuvette and connected by way of polyethylene tubing to an infusion pump. The other capillary tube was positioned at the top of the cuvette and served to remove fluid from the cuvette. The volume of the cuvette was ~1.5 ml, and the flow rate through the cuvette was 5 ml/min. It is important to note that switch in perfusion solutions is removed in time and space for the cuvette, such that a 10-15 second time lag exists before agonist is exposed to the cells. Experiments were performed at room temperature. Fluorescence intensities at both wavelengths were assessed and only those preparations in which there were >200,000 counts/s for both wavelengths were used for experiments. At the beginning of each experiment, cells were perfused with solution A (see below) and the fluorescence ratio was monitored for at least 100 sec to establish a stable baseline value. Agonists and antagonists were then added to the appropriate solutions. The 340/380 ratios (R) were converted into $Ca^{2+}$ values using the equations of Grynkiewicz et al. as follows: $Ca^{2+}=Kd\times[(R-Rmin)/(Rmax-R)]\times(Sf380/Sb380)$ where Kd is the dissociation constant of Fura-2 for $Ca^{2+}$, Rmax and Rmin are R values under saturating and $Ca^{2+}$-free conditions, respectively, and Sf380 and Sb380 are the fluorescent signals (S) emitted by $Ca^{2+}$-free (f) and $Ca^{2+}$+-bound (b) forms of Fura-2 at a wavelength of 380 nm. In situ cell calibrations were accomplished after the cells were permeabilized with 2 μM ionomycin under $Ca^{2+}$-free (10 mM EGTA) and saturating $Ca^{2+}$ (3 mM CaCl2) conditions. The Kd was assumed to be 224 nM.

The best conditions for $Ca^{2+}$ entry were a $Ca^{2+}$ entry solution where sodium was substituted fully with N-methyl-D-glucamine (other impermeant cations such as Tris and choline also work), magnesium was omitted, and calcium could be enriched (from 1.5 to 3 mM) were the conditions in which the best rescues of chloride secretion in CF and insulin secretion from β cells were observed. Modification of the vehicle pH is also essential in the case of zinc's effects in airway epithelial cells for cystic fibrosis. However, this is not an absolute requirement, because zinc increases cell calcium in pancreatic β cells in the same effective dose range at neutral pH. All other constituents remained similar to what is found in standard Ringers or saline solutions.

Airway epithelial P2XRs are calcium entry channels gated by ATP and modulated by extracellular zinc, Na+ and pH. Both ATP and zinc in Na+-free medium at pH 7.9 induce a fully sustained $Ca^{2+}$ signal. In IB3-1 and 16HBE14o-cells, administration of ATP (100 µM) and $ZnCl_2$ (20 µM) induced a rapid increase in $Ca^{2+}$ followed by a sustained plateau. The sustained $Ca^{2+}$ plateau was significantly higher than basal $Ca^{2+}$ in IB3-1 cells ($\Delta[Ca^{2+}]i$=297±44 nM; n=7) and in 16HBE41o-cells ($\Delta[Ca^2+]i$=444±69 nM; n=6). The $Ca^{2+}$ plateau was eliminated upon removing agonists, reducing external pH, or replenishing external Na+ and was not achieved with inclusion of 2 µM $ZnCl_2$ with ATP.

Using the same optimized and novel chemical conditions within the saline vehicle for $Ca^{2+}$ entry, removal of Na+ and $Mg^{2+}$ along with enrichment of $Ca^{2+}$ led to sustained $Ca^{2+}$ entry in the INS-1 rat pancreatic β cells without any addition of agonist. The same was true with alkalinization of the pH in addition to the modification in saline cation content. Furthermore, addition of zinc alone (1-50 micromolar) led to a further sustained increase in $Ca^{2+}$ entry quite similar to what was observed in airway and kidney epithelial cells.

Example 4

Fura-2 Quenching Experiments to Show Direct $Mn^{2+}$ Entry through $Ca^{2+}$ Entry Channels Induced by Zinc In a modification of this technique, instead of directly measuring cytosolic $Ca^{2+}$ with the Fura-2 dye, a Fura-2 quenching experiment was performed in which MnCl2 (500 µM) was added to the $Ca^{2+}$- and EGTA-free solutions to directly assess cation entry (where $Mn^{2+}$ was carrier instead of $Ca^{2+}$ through $Ca^{2+}$ entry channels). In these studies, a ligand like zinc is added to stimulate $Mn^{2+}$ entry and Fura-2 fluorescence is inhibited, lowered, or quenched by $Mn^{2+}$ binding to the Fura-2 dye (in contrast, $Ca^{2+}$ binding excites the Fura-2 fluorescence). This assay provided further proof that zinc (10-50 µM) and/or ATP (10-100 µM) were potent $Ca^{2+}$ entry channel agonists.

Cells were loaded and washed as described for intracellular $Ca^{2+}$ measurement. Fluorescence signal was measured at 359 nm (isosbestic wavelength) in the presence of MnCl2 (500 µM), to detect $Ca^{2+}$-independent changes in Fura-2 fluorescence. Data are expressed as mean±SD. Unpaired Student t-test was used to compare the data in different experimental groups. Results were considered significant if p<0.05. For original Fura-2 traces shown in the Figures, data are graphed with calibrated cytosolic free calcium on the Y-axis, because data from an individual preparation of cells was accumulated for all of the experiments in that Figure where a calibration was also performed.

To directly demonstrate the effect of ATP on $Ca^{2+}$ influx from extracellular sources via another approach, quenching of Fura-2 at 359 nm was measured in the presence of MnCl2 (500 µM). $Mn^{2+}$ is known to permeate the same entry channels as $Ca^{2+}$ and quenches Fura-2 fluorescence when it enters the cells. In Na+-free medium, acidic extracellular pH (6.4) inhibited $Mn^{2+}$ entry, while alkaline extracellular pH (7.9) potentiated markedly $Mn^{2+}$ entry and quenching of the dye. To further support the involvement of P2X4 receptor channels, the effect of the P2X receptor co-agonist, $Zn^{2+}$, on ATP-induced $Ca^{2+}$ entry mechanisms was tested. Inclusion of $ZnCl_2$ (20 µM) further augmented the sustained increase in $Ca^{2+}$ induced by ATP in Na+-free medium but had no effect in Na+-containing medium. Since the biochemical data indicated that P2X4 receptors are also present in 16HBE41o-non-CF airway epithelial cells, they were tested to establish whether increasing extracellular pH or addition of $Zn^{2+}$ augmented the ATP-induced sustained $Ca^{2+}$ entry in Na+-free medium in 16HBE41o-cells. ATP elicited extracellular pH-dependent quenching of Fura-2, suggesting that ATP-stimulated $Ca^{2+}$ influx is facilitated by alkaline pH. In addition, similar to results obtained with IB3-1 cells, both $Zn^{2+}$ and increasing pH potentiated the effects of ATP on sustained $Ca^{2+}$ signal.

The evidence for a specific effect of $ZnCl_2$ alone or with ATP on P2X receptor $Ca^{2+}$ entry channels (P2Xs) is multifold. First, the effective concentrations of zinc and the nucleotide, ATP, as well as the fact that zinc and ATP act as synergistic co-agonists to have optimal effect suggest roles for P2XRs. Second, potentiation of the $Ca^{2+}$ entry phenotype with alkaline pH and an allosteric modulator of P2XRs, ivermectin, shows P2XRs in general and P2X4 in particular. Third, copper and other metals competitively inhibit zinc effects, which also speaks to P2XRs and P2X4. Fourth, molecular biological approaches that allow for "knockdown" of the translation of a particular protein through antisense oligonucleotide inhibition of the mRNA or interference of an mRNA with a small interference RNA (siRNA) construct also inhibited the zinc-induced $Ca^{2+}$ entry when targeted against P2X4, P2X5, and/or P2X6. Fifth, other $Ca^{2+}$ entry mechanisms including voltage-dependent $Ca^{2+}$ entry channels, store-operated (SOCs) or transient receptor potential (TRPs), zinc-activated cation channels (ZACs), epithelial $Ca^{2+}$ entry channels (ECaCs, CaTs), and the reverse mode of the Na/Ca exchange were ruled out.

Zinc increased $Ca^{2+}$ in a sustained manner. Zinc also triggers the release of $Ca^{2+}$ from so-called intracellular or ER stores. In addition to zinc-induced $Ca^{2+}$ entry via P2XRs, these two additional effects of zinc aid a sustained $Ca^{2+}$ signal that is induced by zinc. Nevertheless, zinc does not inhibit all calcium buffering mechanisms, because the effect was reversible upon washout of zinc, a change in external pH to 7.3, or a replenishment of external Na+. Zinc-induced increases in $Ca^{2+}$ were merely small and transient in $Ca^{2+}$-free medium. In $Ca^{2+}$-free medium, thapsigargin pretreatment abolished zinc-induced $Ca^{2+}$ transients, indicating a minor involvement of intracellular $Ca^{2+}$ stores. Taken together, these data show that zinc increases $Ca^{2+}$ from intracellular and extracellular $Ca^{2+}$ stores and can also inhibit a Ca$^{2+}$ buffering mechanism, the plasma membrane Ca$^{2+}$ ATPase pump, in order to elicit a long-lived increased cell Ca$^{2+}$ signal plateau.

Example 5

Analysis of Cl$^-$ Transport using SPQ Fluorescence Dye-Based Imaging of Intracellular Halide Activity The methods used in this assay are essentially the same as those used in Braunstein et al. (J. Biol. Chem. 276:6621-6630, 2001). Modifications to this method involved the use of NaCl at the beginning and end of protocols. Agonists were tested in NMDGNO3-containing solution (as above for Ca$^{2+}$ assays).

In our modified saline vehicle that was devoid of Na+ and Mg$^{2+}$ and enriched in Ca$^{2+}$ (3 mM) along with modifications in the halides (Cl− substituted with iodide to quench the SPQ dye and nitrate to unquench), ATP plus zinc or zinc alone was added to IB3-1 CF cells and halide efflux was rescued in these cells. The effects were dependent upon an alkaline extracellular pH (pH 7.9) and the presence of extracellular Ca$^{2+}$. In essence, the rescue of Cl− transport (measured with a different halide in this case) was dependent upon the same chemical conditions as the zinc-induced Ca$^{2+}$ entry. This data showed that zinc-induced Ca$^{2+}$ entry provided a sustained Ca$^{2+}$ signal for rescue of Cl− transport in CF cells.

Example 6

Analysis of Transepithelial Cl$^-$ Secretion and Na+ Absorption Using Electrophysiological Recordings in Circulating Ussing Chambers or with Voltohmmeters Primary cultures of mouse and human non-CF airway epithelial monolayers were studied that have a higher electrical resistance (mouse=>1,000 Ω·cm2; human=>500 Ω·cm2), are well differentiated, and have a ciliated apical membrane. This high resistance is achieved over 8-14 days on 6 mm diameter collagen-coated Costar Transwell filters. Substantial positive (>20 µA/cm2) transepithelial current (Isc) and negative (>−10 mV) transepithelial voltage are observed routinely in these monolayers under basal conditions. For mouse tracheal monolayers, four monolayers were studied simultaneously in four parallel Ussing chambers interfaced with two Ussing chamber amplifiers. Zinc, small molecules, or ligands were added to either side of the monolayer and were not washed from the chamber at any time during the 1-2 hour recording. The same was true of amiloride, Cl− channel inhibitors, bumetanide, and barium chloride. For human airway epithelial monolayers, these methods have been published (Smith, J. J. and M. J. Welsh. J. Clin. Invest. 89:1148-1153.1992.19. Zabner, J., L. A. Couture, A. E. Smith, and M. J. Welsh. Human Gene Therapy 5:585-593.1994). Transepithelial resistance was ≧1000 Ω/cm2. Apically, we used NMDGgluconate solution containing amiloride (20 µM), CaCl2 (3 mM) (pH 7.9 adjusted with gluconate). Basolaterally, we used NaCl solution (1.5 mM CaCl2; pH 7.3 adjusted with NaOH).

Zinc and ATP stimulate Cl− secretion in CF and non-CF human airway epithelial cell monolayers. Rescue of transepithelial Cl− transport across a polarized epithelium is useful in airway disease therapy. Thus, primary human CF and non-CF cells were screened, as well as immortalized non-CF (CALU-3) airway epithelial cell monolayers. In the presence of amiloride and a "basolateral towards apical" Cl− gradient in Na+-free solution, ATP and ZnCl$_2$ stimulated Cl− secretion in both CF and non-CF airway epithelial cells. Stimulated Cl− secretion was biphasic, showing transient and sustained components. Washout of the agonists abolished the sustained current, while re-addition of agonists stimulated Cl− secretion that was fully sustained. Taken together, these data show that P2XR agonists, under conditions that allow for optimal Ca$^{2+}$ entry from extracellular stores, stimulated sustained Cl− secretion in polarized CF and non-CF human airway epithelia Both kidney and airway epithelia in CF show enhanced Na+ absorption across airway epithelia. It is shown in kidney collecting duct epithelia in autosomal recessive polycystic kidney disease, and in renal hypertensive syndromes such as salt-sensitive hypertension, Liddle's syndrome, Bartter's syndrome, and Gitelman's syndrome. The rate-limiting step in this enhanced Na+ absorption detrimental to cystic fibrosis and hypertension is the epithelial Na+ channel or ENaC. Despite no amino acid or nucleotide sequence homology, the topology or overall structure of ENaCs is quite similar to the P2XRs. In fact, the extracellular domain of ENaCs and P2XRs accounts to 70% of the molecular mass of the two similar cation channel protein subfamilies, and there are an large and even number of extracellular cysteines thought to participate as pairs in intrachain disulfide bonding in two cysteine-rich regions. Ussing chamber recordings were performed in mouse non-CF and CF airway epithelial cell monolayers in primary cultures as well as mutant PKD collecting duct epithelial cell monolayers versus genetically rescued controls. First and foremost the diseased cell monolayers for both CF airway and PKD kidney had enhanced ENaC activity that mediated enhanced Na+ absorption. In direct comparison to the diuretic, amiloride, a known inhibitor of ENaC also used in hypertension management, zinc inhibits ENaC in a similar micromolar concentration range (50-100 micromolar for zinc, 1-50 micromolar for amiloride). Although zinc is an agonist for the P2XRs, it is an antagonist for ENaCs. While zinc, via P2XRs, can rescue Cl− secretion in CF, zinc attenuates ENaC-mediated hyperabsorption of Na+ in CF, an added therapeutic benefit. Zinc inhibition of ENaC is also beneficial to quell Na+ absorption and fight hypertension in affected individuals in the collecting duct of the kidney.

Example 7

Coulter Counter Multisizer III-Based Cell Volume Assays

The methods used in this assay are essentially the same as those used in Braunstein et al. (J. Biol. Chem. 276:6621-6630, 2001) and Braunstein et al. (J. of Cystic Fibrosis Epub Ahead of Print). Modifications to this method were use of a Coulter Counter Multisizer III (Beckman Coulter) with Accu-Comp software that allows continuous data collection. All experiments were performed in NMDG-containing solution (as above for Ca$^{2+}$ assays).

Zinc and/or ATP in modified solution restored Cl− transport through activation of CLCAs in CF cells. In SPQ halide fluorescence assays of Cl− efflux, ZnCl$_2$ alone or in combination with ATP restored Cl− permeability. These effects are dependent upon the presence of extracellular Ca$^{2+}$ and the modified external Na+ and H+. IB3-1 CF cells are impaired in their cell volume regulatory processes. However, ZnCl$_2$ alone or in combination with ATP corrected regulatory volume decrease (RVD) after hypotonic cell swelling. Rescue of RVD was dependent upon extracellular $Ca^{2+}$, since no rescue was observed in $Ca^{2+}$-free medium.

Example 8

In Vivo Nasal Potential Difference Electrophysiological Recordings in Normal and Cystic Fibrosis Transgenic Mouse Models Lactated Ringer was instilled into the nasal passages, and an electrode was placed into the nose of wild-type or CFTR knockout mice while the tail was placed in a vessel of Ringer as the ground. A three-step protocol was used in these nasal PD recording. First, nasal PD was measured until stable in lactated Ringer containing amiloride to inhibit IscNa. Second, amiloride in a "low Cl−" lactated Ringer was circulated into the mouse nose and measured until stable. Third, P2X receptor agonists were added to amiloride-containing low Cl− Ringer to evaluate activation of Cl− transport across the nasal mucosa.

Furthermore, zinc and ATP correct defective Cl− transport in nasal potential difference assays of mice. A critical test for a therapeutic agonist for CF airway dysfunction is the NPD assay in anesthetized mice, tested by measuring the effects of combined application of ATP and zinc on Cl− secretion in wild-type and CF mice in a Na+-free solution (pH 7.9). In mice with at least one wild-type allele, the NPD depolarizes in a gradual decay in the presence of amiloride. In the presence of amiloride, reduction of mucosal Cl− caused significant hyperpolarization. Addition of ATP and $ZnCl_2$ caused further hyperpolarization that was sustained. This protocol was tested in two different CF mouse models; a $\Delta F508$-CFTR homozygous mouse and a transgenic mouse where the lungs are null for CFTR but intestinal dysfunction was corrected with a fatty acid-binding protein promoter (FABP)-driven CFTR construct (referred to as "the Cincinnati CF mouse"). Reduction of mucosal Cl− in the presence of amiloride (50 μM) was without effect. However, administration of ATP and $ZnCl_2$ caused marked hyperpolarization in both CF mouse models. Taken together with the results above, these data support P2XRs as a therapeutic target for CF airway disease.

Nasal PD and $Ca^{2+}$ imaging showed that zinc and/or ATP could stimulate $Ca^{2+}$ entry or Cl− transport that was reversible and fully re-acquired upon re-addition of agonists. This is another novel feature of epithelial P2XRs, lack of desensitization or inactivation. The duration, reversibility, and reproducibility of a potential therapeutic are key issues, especially one that targets an endogenous receptor. The duration of agonist effect as well as washout and re-administration of agonists was tested. In CF mice, administration of ATP and zinc hyperpolarized the NPD in a sustained manner for 15 minutes. This long-lasting stimulation was fully reversible upon removal of the agonists. In addition, multiple exposures of the nasal mucosa to the agonists elicited similar Cl− secretory responses, suggesting that P2XRs do not desensitize or inactivate. Notably, in both CF mouse models, ATP and zinc induction of Cl− secretion was more rapid when the low Cl− solution added prior to the agonist-containing solution was pH 7.9. Furthermore, an assay was done in which P2XR agonists hyperpolarized the nasal PD by approximately 10 mV under modified vehicle conditions in solution each of three times, where the assay was washed out and the agonist/solution was readministered. Taken together, these data show that P2XR-mediated effects are reversible and reproducible.

Example 9

Reverse Transcription Polymerase Chain Reaction (RT-PCR) Analysis of Specific Epithelial and Pancreatic β Cell P2XR Subtypes.

PCR primers specific to P2X4, P2X5, and P2X6 were designed to amplify the full-length open reading frame or complementary DNA (cDNA) for each P2XR subtype. In the context of this work that successfully amplified and cloned these cDNAs for P2X4, P2X5, and P2X6 from human airway epithelia (work in progress for mouse kidney epithelia and rat pancreatic β cells), we also amplified several splice variant forms of each P2XR subtypes that had specific exons missing, multiple exons missing from a single transcript, partial exon deletions, and intron insertions.

PCR products of the expected size were amplified for TRPC3 (@300 base pairs (bp)) and TRPC4 (@400 bp). These PCR products were verified by DNA sequencing to be TRPC3 and TRPC4. IB3-1 cells are a CF human bronchial epithelial cell line, 16HBE and 9HTE cells are normal human airway epithelial cell lines, MDCK cells are a canine kidney epithelial cell line, and mCCD-K1 cells are a mouse kidney collecting duct epithelial cell line. Six such amplifications were performed. This is a representative blot from at least 5 such analyses. IB3-1 cells are a CF human bronchial epithelial cell line, 16HBE and 9HTE cells are normal human airway epithelial cell lines, and T84 cells are a human intestinal epithelial cell line. Calu-3 cells are a serous cell line derived from human submucosal gland and are negative for TRPC4. This shows that specific RT-PCR reveals abundant and broad expression of TRPC3 and TRPC4.

Example 10

Immunoblotting with P2X Receptor Channel and TRP Channel Isoform-specific Antibodies in Epithelial Cells and Pancreatic β Cells Cells were lysed in a buffer containing 10 mM Tris, 0.5 mM NaCl, 0.5% Triton X-100, 50 μg/ml aprotinin (Sigma, St. Louis, Mo., USA), 100 μg/ml leupeptin (Sigma) and 100 μg/ml pepstatin A (Sigma) adjusted to pH 7.2-7.4. Twenty micrograms of protein were run per lane and separated on a 8% SDS-polyacrylamide gel and then transferred to a polyvinyledene difluoride membrane (Osmonics, Westborough, Mass., USA.) Inmunoblotting was performed with a rabbit polyclonal antibody to P2X4 (Alomone Laboratories, Jerusalem, Israel) at a dilution of 1:500. P2X1, P2X2, and P2X7 antibodies were also obtained from Alomone Laboratories and were tested in a similar manner. Reactivity was detected by horseradish peroxidase-labeled goat anti-rabbit secondary antibody (1:3,000 dilution, New England BioLabs, Beverly, Mass.). Enhanced chemiluminescence was used to visualize the secondary antibody.

Membrane protein lysates from IB3-1 cells were prepared and were subjected to immunoblotting with a P2X4-specific polyclonal antibody. Positive results were obtained for P2X4 receptor channel protein in total membrane protein lysates from IB3-1 cells grown on collagen-coated plastic as confluent monolayers. Inconsistent signals or a lack of a signal was observed for P2X1, P2X2, and P2X7 using specific antibodies to those subtypes. The P2X4 signal displayed a similar biochemical phenotype compared to human vascular endothelial cells and human polycystic kidney disease renal epithelial as well as P2X4 receptor biochemistry in cardiac tissue and myocytes. An unglycosylated band was detected at approximately 46 kDa (the predicted molecular mass for P2X4) and a larger and broader glycosylate band at 60-65 kDa. These immunoblotting data show that P2X4 is the most abundant P2X subtype expressed in IB3-1 cells. However, these data do not rule out less abundant expression of other P2X subtypes that is below the limit of detection with these antibodies. Further chemical modification of the extracellular solution also supports the abundant expression of P2X4 receptor channels as the major P2X receptor subtype mediating $Ca^{2+}$ entry.

Western blot analysis reveals abundant and broad expression of TRPC4. A blot was done for at least 5 such analyses. IB3-1 cells are a CF human bronchial epithelial cell line, 16HBE and 9HTE cells are normal human airway epithelial cell lines, and T84 cells are a human intestinal epithelial cell line and are positive for TRPC4. Calu-3 cells are a serous cell line derived from human submucosal gland and are negative for TRPC4. This shows that epithelial cells express multiple TRPC calcium entry subtype proteins.

Example 11

Biotinylation of Plasma Membrane P2X Receptor Channels and TRP Channels in Epithefial Cells and Pancreatic β Cells Cells were seeded on Vitrogen-coated (collagen types I and IV diluted 1:15 in Dulbecco's phosphate buffered saline) 12 mm filters and grown as polarized monolayers with a transepithelial resistance that exceeded 400 Ohm/cm2. Cells were placed on ice and washed 3 times with cold PBS supplemented with 0.1 mM CaCl2 and 1.0 mM MgCl2. Cells were then incubated in 1.0 mg/mL PEO maleimide (Pierce, Rockford, Ill.) or sulfo-NHS-LC biotin (Pierce) in cold supplemented PBS for 25 minutes at 4° C. Cells were washed 4 times with cold supplemented PBS, and the biotin was quenched with 0.1% BSA (Sigma). Cells were then washed with cold supplemented PBS 3 times. Alternatively, cells could be biotinylated with biocytin hydrazide. Filters were first incubated in 300 µl of a stock solution containing 30 mM NaIO4 and 600 µl of a stock solution containing 100 mM Na-acetate and 0.02% Na-azide, pH 5.5 for 30 minutes at room temperature in the dark. Filters were washed and subsequently incubated with 1.0 mg/ml biocytin hydrazide (Pierce) for 1 hour at 4° C. The reaction was quenched with 0.1 M Tris, pH 7.5. Cell lysates were collected as described above in immunoblotting procedures. Immobilized streptavidin beads (Pierce) were added to the lysates at a 1:10 dilution and rocked overnight at 4° C. Beads were washed 3 times with lysis buffer and incubated in sample buffer for 5 minutes at 95° C. The mixture was centrifuged and the supernatant was loaded onto an SDS-PAGE gel. The immunoblotting procedure then continued as described above.

Immunoblotting of non-polarized cells grown in flasks as well as biotinylation of polarized monolayers grown on permeable supports revealed robust and apical membrane-localized expression of P2X4. In these lysates, a third band of approximately 100 kDa was also found. Biotinylation was performed on the apical and basolateral surface of these monolayers. Secondary antibody controls and blocking of antibody binding with the peptide immunogen provided with the primary antibody in all biochemical assays verified the specificity of P2X4 receptor expression. Therefore, P2X4 receptors are expressed abundantly by human airway epithelial cells grown under non-polarized and polarized conditions.

Biotinylation of cell surface TRPC4 calcium entry channels occurs in polarized epithelia. Biotinylation of both sides of the epithelial monolayer were performed, except for the mCCD lanes containing apical membrane and basolateral membrane. This confirms that TRPC4 calcium entry channels are expressed in the plasma membrane of polarized epithelial cell monolayers.

Example 12

Immunohistochemical Staining for the P2X Receptor Channels and TRP Channels in Epithelial Cells and Pancreatic β Cells Human tissues were procured and handled by the UAB CF Center. Tissues were fixed in buffered formalin and embedded in paraffin using standard conditions. After sectioning and deparaffination, tissue sections were rehydrated in PBS and were blocked with goat serum (1:20 in PBS/0.1% Tween-20) for 2 hours. Primary antibodies (anti-P2X4 rabbit polyclonal antibody 1:100 dilution, Alomone Labs; anti-CFTR monoclonal antibodies M3A7, Upstate Biotech, and 24-1, Genzyme, in tandem at 1:50 dilution each) and secondary antibodies (anti-mouse Alexa-Fluor594 for P2X4 and Alexa-Fluor488 for CFTR at 1:400 dilution) were diluted in blocking solution. Primary antibody incubations were 14 hours followed by three 15-minute washes in PBS/Tween-20; secondary antibody incubations were 1 hour followed by similar washes. Tissues were mounted and nuclei stained with Vectashield/DAPI (Vector Labs). Slides were visualized on a Leitz epifluorescence microscope equipped with step motor, filter wheel assembly (Ludl Electronic Products), and 83,000 filter set (Chroma Technology). Images were captured with a SenSys-cooled charge-coupled high-resolution camera (Photometrics), and partial deconvolution of images was performed using IPLab software (Scanalytics).

Immunohistochemistry of human non-CF and CF airway tissue with an anti-P2X4 polyclonal antibody revealed staining of the airway surface epithelium and on cilia. Verification of CFTR expression was assessed in parallel staining of the same tissues with anti-CFTR antibodies, revealing apical staining of non-CF airway surface epithelium, but no staining in CF tissue. Staining for P2X4 was also apparent on the basolateral aspect of the epithelium, a finding consistent with functional studies, and on alveolar type II pneumocytes. Staining for P2X4 was not different in non-CF and CF tissues. P2X4 receptors are present on the luminal membrane and on cilia in CF human airways and can be targeted with aerosolized, nebulized, sprayed, or instilled P2XR agonists contained in optimal saline vehicle.

A co-staining was also done for the apical membrane marker, the cystic fibrosis transmembrane conductance regulator or CFTR, the CF gene product. Both CFTR and P2X4 were present in the apical or luminal membrane lining the airways. Co-staining for P2X4 and the tight junction marker, zonula occludens 1 or ZO-1, the boundary between apical and basolateral epithelial cell membrane domains, revealed both luminal and serosol (basolateral) staining consistent with past functional studies. Co-staining for P2X4 and the ciliary structural proteins, beta- and gamma-tubulin, revealed staining for P2X4 on the basal half of luminal cilia.

Example 13

Enzyme-Linked Absorbance Assay (ELISA Assay) for Secreted Insulin from a Rat Pancreatic β Cell Line, INS-1, and from Rat Primary Islets from Endocrine Pancreas A rat pancreatic β cell line, INS-1, was chosen from several candidates for this analysis because it maintains the ability to secrete significant amounts of insulin, as pancreatic β cell lines are notorious for losing this function over time. Cells are grown routinely in 11 mM glucose. Two days prior to the ELISA assay of insulin secretion, the cells are switched into a medium with 5 mM glucose. After several washes to remove medium, Ringers modified in their ionic content and/or pH with and without 15 mM glucose (or zinc, zinc plus ATP, etc. as alternative stimuli) are added to the INS-1 cell cultures. Samples are removed at 15 seconds after stimulation and at 15, 30, 60, and 120 minutes after stimulation. The rationale for this time course was to assess the effect of an experimental maneuver on the immediate and later phases of insulin secretion normally observed from β cells in vitro and in vivo. Samples of the solution are then processed in a rat/mouse insulin ELISA kit (Linco Products, Inc.) according to the manufacturer's instructions.

Example 14

High-Throughput Screen for New Ligands that Stimulate Sustained Calcium Entry from Extracellular Stores in CF Epithelial Cells, PKD Epithelial Cells, and Pancreatic β Cells Mammalian cells (epithelial cells, pancreatic β cells, etc.) grown to confluence in 96-well plates. Two hours prior to experimentation, the cells are loaded with 5 μmol/L Fura-2/AM in a low concentration of 1 mg/ml pluronic F-127 surfactant to facilitate loading. The assay is performed in our modified NMDG solution (Na+ free, Mg2-free, 3 mM $Ca^{2+}$) validated to optimize $Ca^{2+}$ entry derived from extracellular stores through $Ca^{2+}$ entry channels. The 96-well plates are then washed for 10 minutes in the saline solution in which the agonists are screened. The Fura-2/AM-loaded cells are then analyzed in a fluorescence plate reader that measures fluorescence at dual excitation wavelengths of 340 nM and 380 nM and at an emission wavelength of 510 nM before and after addition of positive controls for $Ca^{2+}$ entry such as zinc, zinc plus ATP, ionomycin, and thapsigargin and before and after addition of individual test drugs from drug libraries.

Specific ligands are identified out of the larger ligand pool. A new lead ligand that gives a sustained intracellular calcium increase of 300 nM above baseline 5 that is similar to zinc and/or ATP and ionomycin controls is subjected to secondary screens in CF (rescue of chloride secretion in vitro and in vivo, see Examples above), in diabetes (rescue of insulin secretion, see Example above), and in all disease paradigms with relevance to any possible cell toxicity. Candidate ligands are tested in secondary Fura-2/AM based fluorescence experiments to determine whether they synergize with zinc, ATP, or BzBzATP to trigger sustained calcium entry or whether they stimulate another calcium entry channel.

Example 15

Secondary Screens of Rescue of Chloride Secretion in CF Mice

CF mice that were corrected in their intestine by an FABP-CFTR construct but that were still null in the lung and airways for CFTR were used. The mice were treated with low Cl– and isoproternol (isoprel), both of which were without effect in CF mice. The nasal PD continued to decay or depolarize. A challenge with P2XR agonists hyperpolarized the nasal PD by 5-12 mV under modified vehicle conditions in solution (low NaCl, amiloride, P2XR agonists, pH 7.9, 3 mM $Ca^{2+}$).

A delF508/delF508 mice were used. The low Cl– step or addition of isoproterenol (isoprel) were without effect in the mouse; however, challenge with P2XR agonists hyperpolarized the nasal PD by 5-12 mV under modified vehicle conditions in solution (low NaCl, amiloride, P2XR agonists, pH 7.9, 3 mM $Ca^{2+}$). There was a long initial challenge (2 times longer than the normal protocol) and a sustained response when P2XR agonists were used. The assay was washed and re-challenged for a second time, showing the reversibility, reproducibility, and lack of desensitization of the P2XR targets. The second stimulation was also 8-12 mV.

Challenge with P2XR agonists hyperpolarized the nasal PD in delF508/delF508 mice by approximately 10 mV under modified vehicle conditions in solution (low NaCl, amiloride, P2XR agonists, pH 7.9, 3 mM $Ca^{2+}$). The assay was washed and re-challenged three times, each time the nasal PD was hyperpolarized by approximately 10 mV, thus showing the reversibility, reproducibility, and lack of desensitization of the P2XR targets (FIG. 22).

Example 16

RT-PCR in Mammalian Cells for P2X Receptor Channels and TRPC Calcium Entry Channel Messenger RNAs Specific RT-PCR reveals abundant and broad expression of TRPC3 and TRPC4. PCR products of the expected size were amplified for TRPC3 (@300 base pairs (bp)) and TRPC4 (@400 bp). These PCR products were verified by DNA sequencing to be TRPC3 and TRPC4. IB3-1 cells are a CF human bronchial epithelial cell line, 16HBE and 9HTE cells are normal human airway epithelial cell lines, MDCK cells are a canine kidney epithelial cell line, and mCCD-K1 cells are a mouse kidney collecting duct epithelial cell line. Six such amplifications were performed. Western blot analysis revealed abundant and broad expression of TRPC4 in epithelial cells. IB3-1 cells are a CF human bronchial epithelial cell line, 16HBE and 9HTE cells are normal human airway epithelial cell lines, and T84 cells are a human intestinal epithelial cell line. Calu-3 cells are a serous cell line derived from human submucosal gland and are negative for TRPC4. Specific RT-PCR reveals abundant and broad expression of TRPC3 and TRPC4.

Example 17

Enzyme-Linked Absorbance Assay (ELISA) for Insulin Secretion from Pancreatic β Cells A rat pancreatic β cell line, INS-1, is chosen from several candidates for this analysis because it maintains the ability to secrete significant amounts of insulin, as pancreatic β cell lines are known to lose this function over time. Cells are grown routinely in 11 mM glucose. Two days prior to the ELISA assay of insulin secretion, the cells are switched into a medium with 5 mM glucose. After several washes to remove medium, Ringers modified in their ionic content and/or pH with and without 15 mM glucose (or zinc, zinc plus ATP, etc. as alternative stimuli) are added to the INS-1 cell cultures. Samples are removed at 15 seconds after stimulation and at 15, 30, 60, and 120 minutes after stimulation. The rationale for this time course is to assess the effect of an experimental maneuver on the immediate and later phases of insulin secretion normally observed from p cells in vitro and in vivo. Samples of the solution are then processed in a rat/mouse insulin ELISA kit (Linco Products, Inc.) according to the manufacturer's instructions.

Example 18

Immunocytochemical and Biochemical Analysis Reveals P2X$_5$ and P2X$_6$ Protein Expression in Human Airway Epithelial Cells Staining of a 16HBE14o-non-CF human airway epithelial cell monolayer with a P2X5 antisera showed staining of the apical pole of multiple cells in the field of the monolayer. Staining of an island of primary non-CF human nasal epithelial cells derived from a nasal brushing revealed membrane-delimited as well as intracellular staining (secondary antibody controls were negative). Molecular biological analysis of P2X6, P2X5 and P2X4 in human airway epithelial cells has also revealed fall-length and splice variant forms of each epithelial P2XR subtype. RT-PCR amplification specific to P2X6 was performed. A smaller than expected size PCR product was obtained that was confirmed by DNA sequencing to be a P2X6 sequence lacking exon 4 from the genomic DNA. In summary, full-length cDNAs were cloned for P2X6, P2X5 and P2X4 as well as isolated or multiple splice variant forms of these receptor subtypes in epithelia.

Example 19

Zinc Alone or with ATP Rescued Cl− Efflux in IB3-CF Cells

Figure 8A:
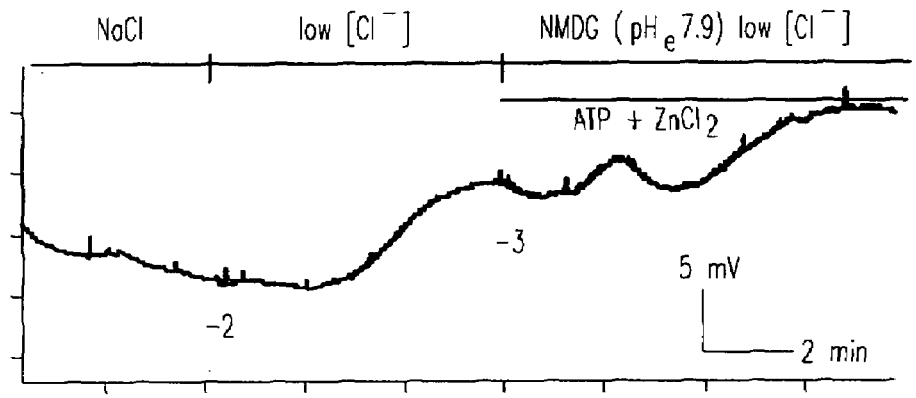
FIG. 8A shows a typical experiment in control animals. The nasal cavity of the mouse was perfused with Na+-containing Ringer solution (pH 7.3) in presence of amiloride (50 μM, showing a gradual decay in NPD (depolarization). Then, a low Cl-containing (6 mM) solution was used. Hyperpolarization occurred upon lowering external [Cl−]. Due to a delay in the perfusion system, hyperpolarization occurred approximately 2 minutes after changing solutions. ATP (100 μM) and $ZnCl_2$ (40 μM) were added in Na+-free medium at pH 7.9. An additional hyperpolarization was seen in the presence of agonists. Typical experiments in a ΔF508 homozygous CF mouse (FIG. 8B) and in a bitransgenic CF mouse (FIG. 8C) were conducted using the same protocol as in FIG. 8A. In both CF mouse models, hyperpolarization occurred only upon addition of agonists.
Figure 8B:
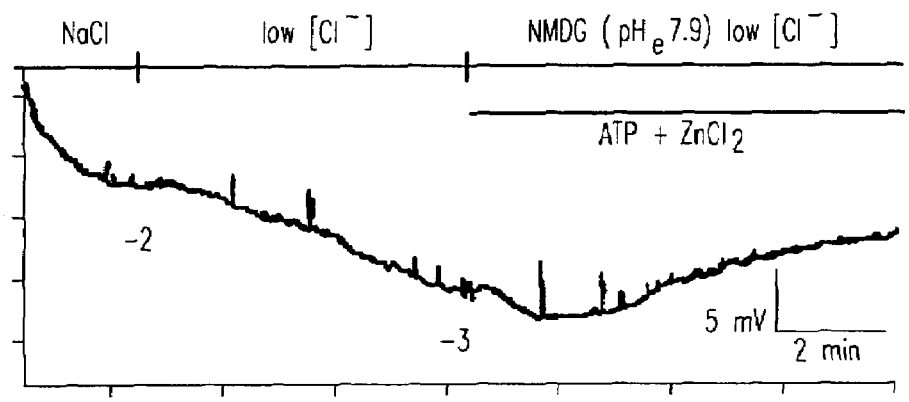
FIG. 8 shows the rescue of secretory chloride transport across control and CF mouse nasal mucosa in vivo.
FIG. 8D shows long exposure to agonists in a ΔF508 homozygous mouse. Extracellular Na+ was substituted by NMDG and pH was raised to 7.9 in low Cl-containing medium before addition of agonists. Then, ATP and $_{ZnCl2}$ were added. The time lag between switching to agonist-containing solution and hyperpolarization is shorter (approx. 1 min) and the amplitude of the response is greater than that achieved in FIG. 8B. Also note that washout of agonists reversed the response completely.
FIG. 8E shows multiple exposures to ATP and $_{ZnCl2}$ in a ΔF508 homozygous mouse. The amplitude of the responses did not decline with time, even upon removal and re-addition of agonists two additional times. CF mice were also exposed to ATP alone in Na+-free low [Cl−]e solution at pHe 7.9. Before adding the agonist, nasal epithelia was perfused with Na+-free low [Cl−]e solution at pHe 7.9.
FIG. 8F shows a data summary table from all of the nasal PD experiments. Starting points represent values (mV) obtained in Ringer solution containing amiloride immediately after the beginning of experiments. Low [Cl−] responses represent the changes in values (mV) reducing [Cl−]e to 6 mM in Na+— or NMDG-containing medium at different pHs. Negative and positive values reflect changes towards hyperpolarization and depolarization, respectively. Effects of ATP and $_{ZbCl2}$ were tested in NMDG-containing medium at pH 7.9 following reduction of [Cl−]. n=number of experiments. *p<0.05 vs. control animals, # p<0.05 vs. CF animals ATP+$ZnCl_2$ after low [Cl−] response with Na+ (pH: 7.3), and p<0.05 vs. Cincinnati animals ATP+$ZnCl_2$ after low [Cl−] response with Na+ (pH:7.3), and p<0.05 vs. ATP+$ZnCl_2$ with NMDG in presence of extracellular $Ca^{2+}$. Effect of ATP alone was assessed by the peak of the hyperpolarization response because of the transient nature of the response.
Figure 8C:
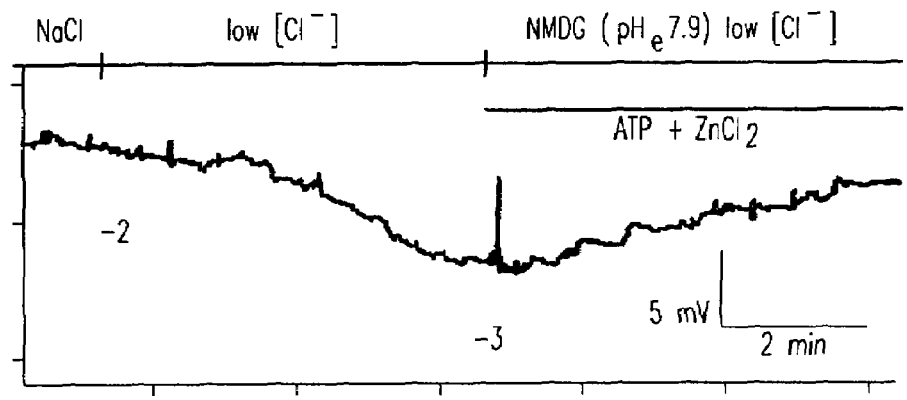
Figure 8D:
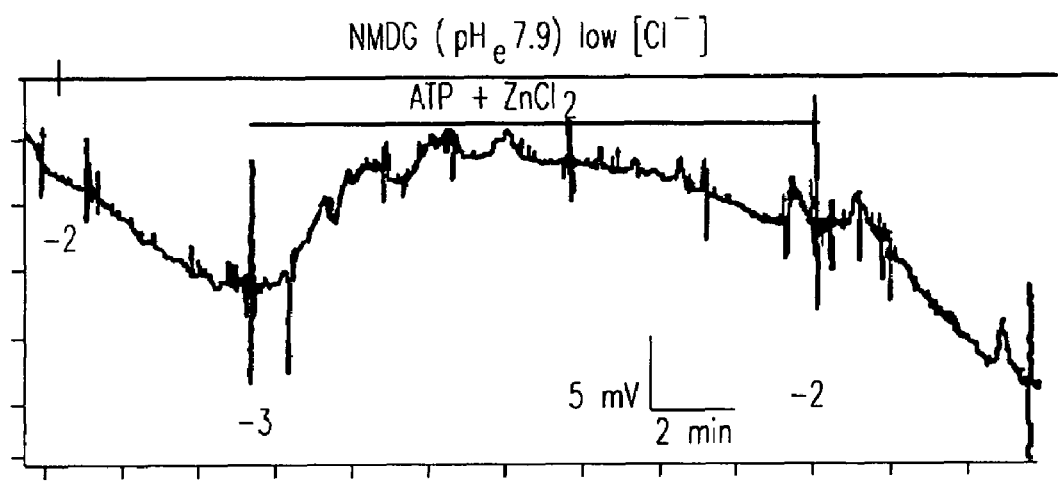
Figure 8E:
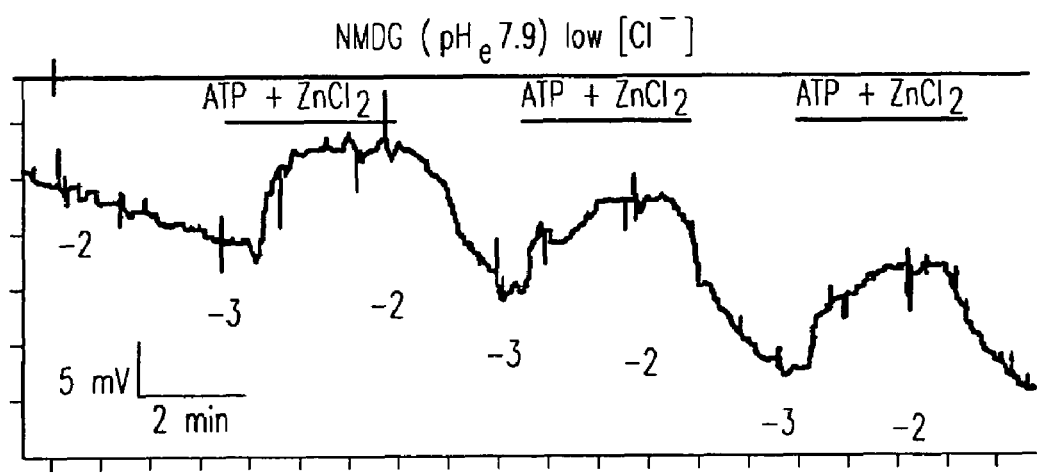
Figure 9A:
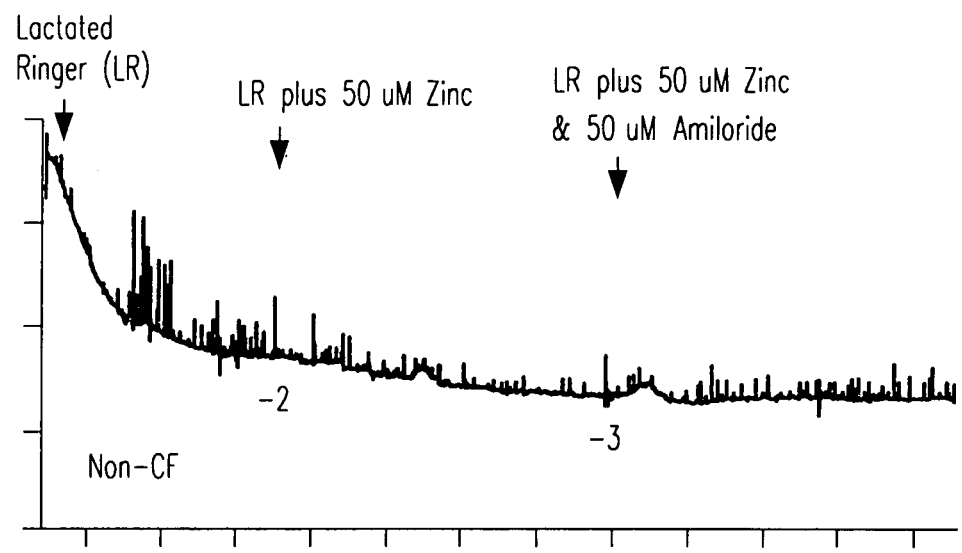
FIG. 9A shows a recording from a control mouse showing a 3-4 mV depolarization induced by zinc indicative of ENaC inhibition; amiloride addition had no additional effect.
Figure 9B:
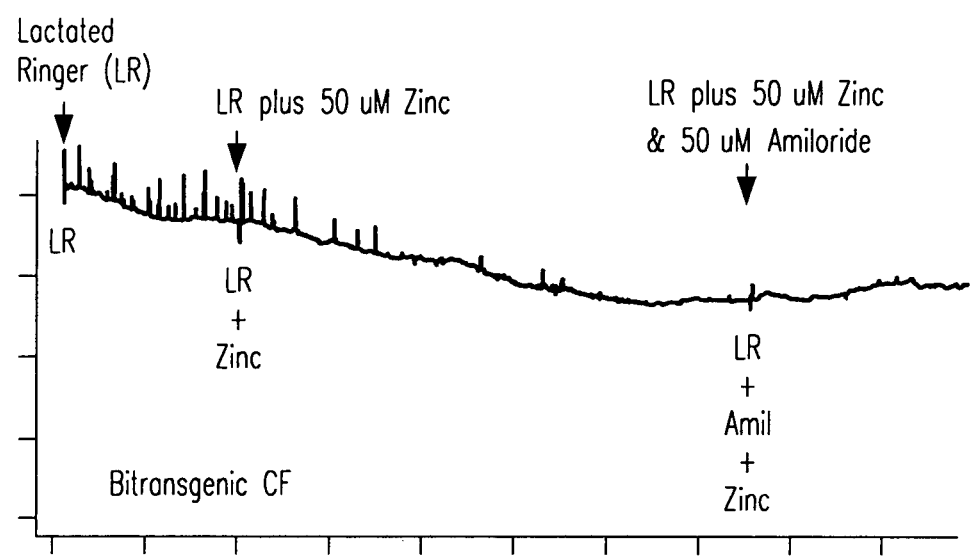
FIG. 9B shows a recording of a Cincinnati bitransgenic CF mouse showing depolarization of the NPD by ~10 mV induced by zinc.
Figure 9C:
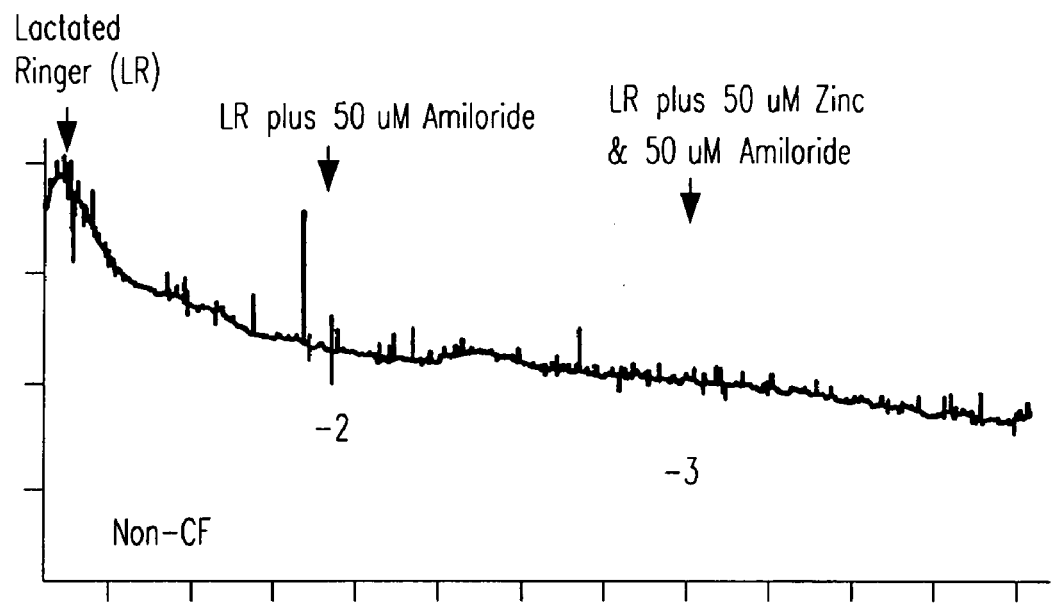
FIG. 9C shows a recording from a control mouse where amiloride also elicited a 3 mV depolarization; addition of zinc with amiloride caused the PD to decay still more. In all non-CF mouse NPD recordings, zinc or amiloride-sensitive Na+ absorptive ENaC current averaged 2-4 mV, while the amount of zinc- and/or amiloride-sensitive ENaC current in CF animals ranged from 6-10 mV. These data are in agreement with in vitro and in vivo data showing upregulated ENaC activity in CF.
Figure 9D:
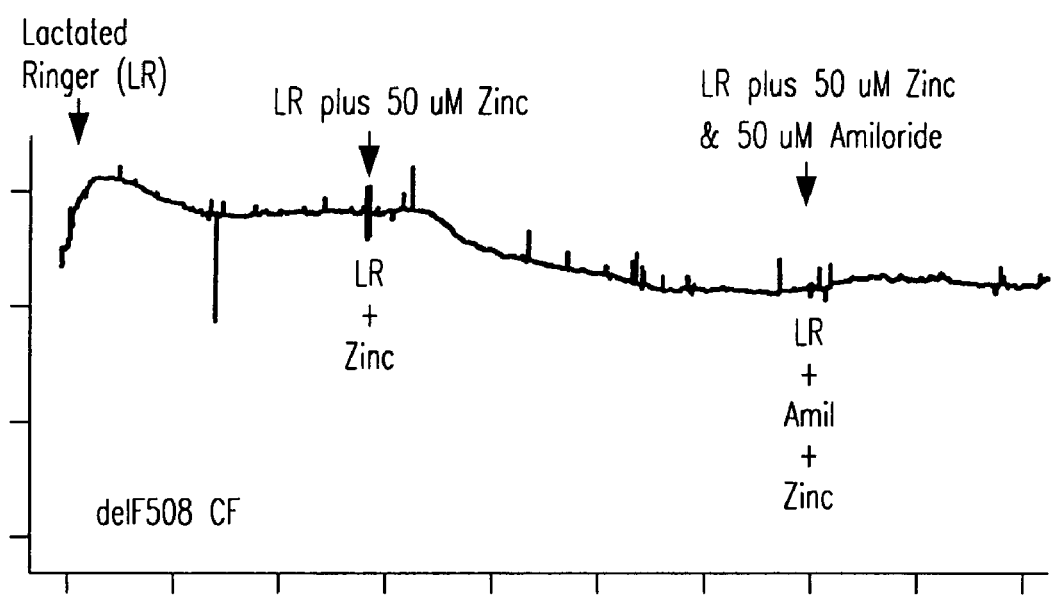
FIG. 9D shows a recording of a delF508 CF mouse showing depolarization of the NPD by ~6-7 mV caused by zinc. Later addition of amiloride (50 μM), the dose used in all solutions in the rescue of Cl− secretion data to fully inhibit ENaC, had no further effect (e.g., there was no ENaC to inhibit). These are typical traces of several such recordings.
Figure 10A:
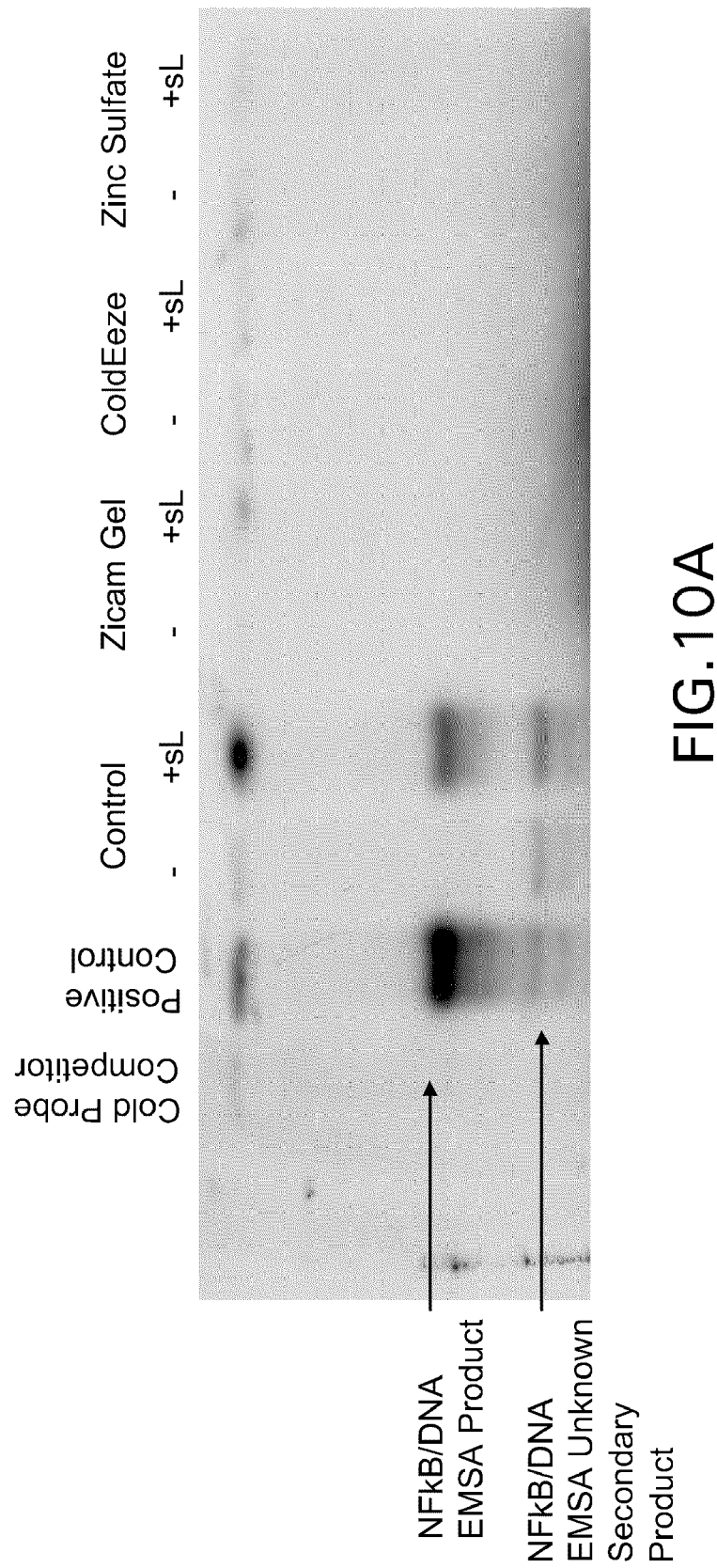
FIG. 10A shows NFkappaB activation by soluble CD40 ligand activation of the epithelial CD40 receptor is inhibited by homeopathic zinc formulation and zinc sulfate. Complete abolishment of CD40 receptor-induced NFkappaB activation was observed with both Zicam (1:10 dilution of the nasal gel in medium) and 1:10 dilution of a 1 gram/ml stock of ColdEeze (as well as 10 mM zinc sulfate studied in parallel), sL=soluble CD40 ligand (400 ng/ml for 30 minutes), 4 micrograms of nuclear extract run for each sample, and 3 day exposure. Note that a lower secondary product is also inhibited by the zinc formulations.
Figure 10B:
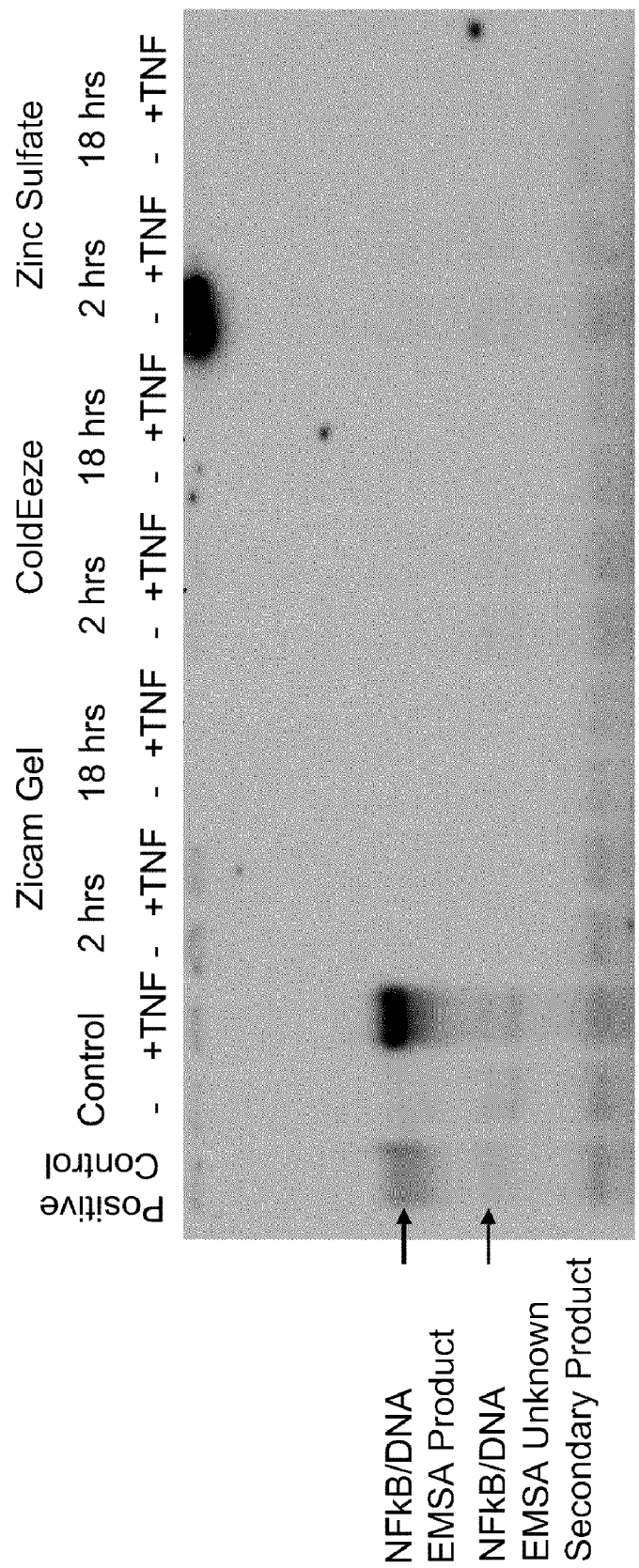
FIG. 10B shows a similar experiment where the human airway epithelial cells were exposed to the same zinc formulations for both 2 and 18 hours. NFkappaB was induced by TNFalpha (100 ng/ml) in this experiment.
Figure 10C:
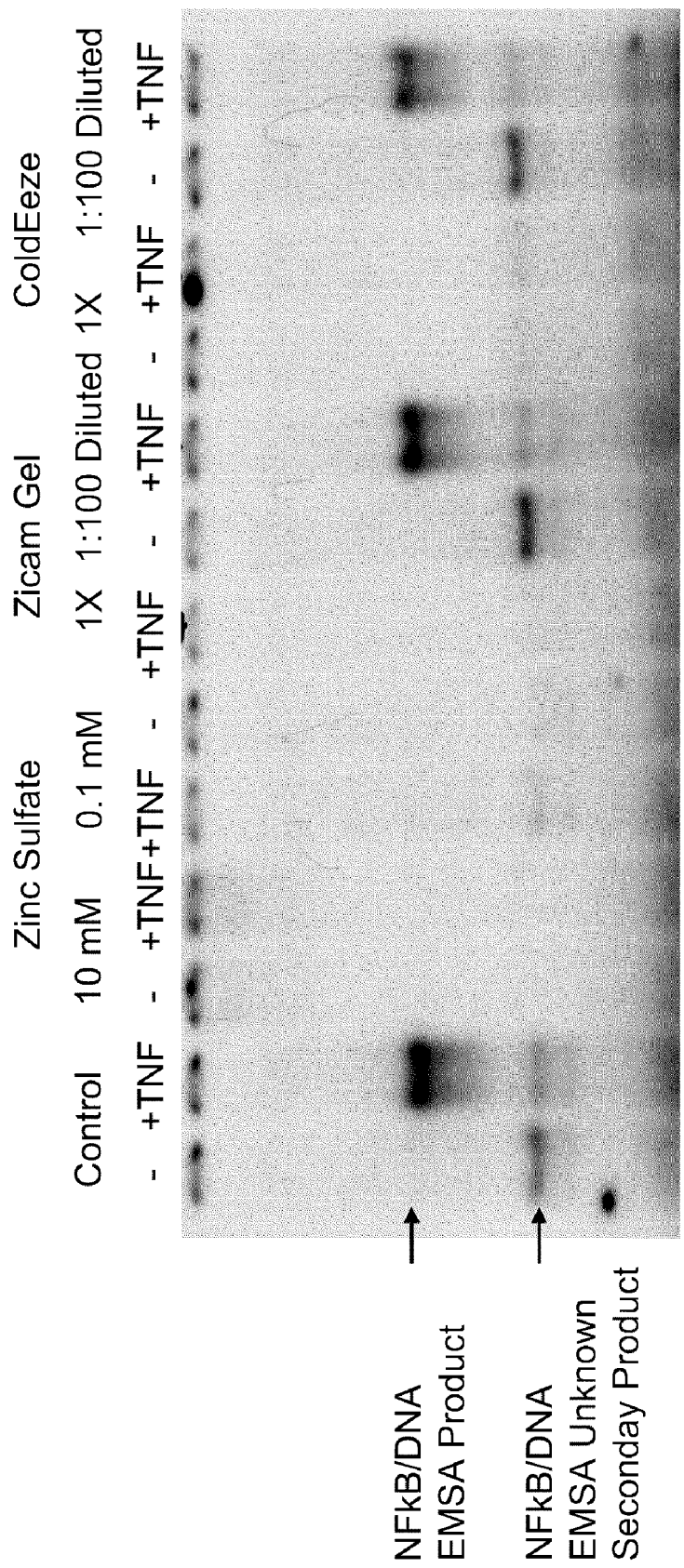
FIG. 10C shows similar experiment to FIG. 10A but with 1× and 1:100 dilutions of the three zinc formulations above 1:100 dilution of Zicam and ColdEeze blunted their block of NFkappaB induction, while 100 μM zinc sulfate still fully blocks NFkappaB induction.
Figure 11A:
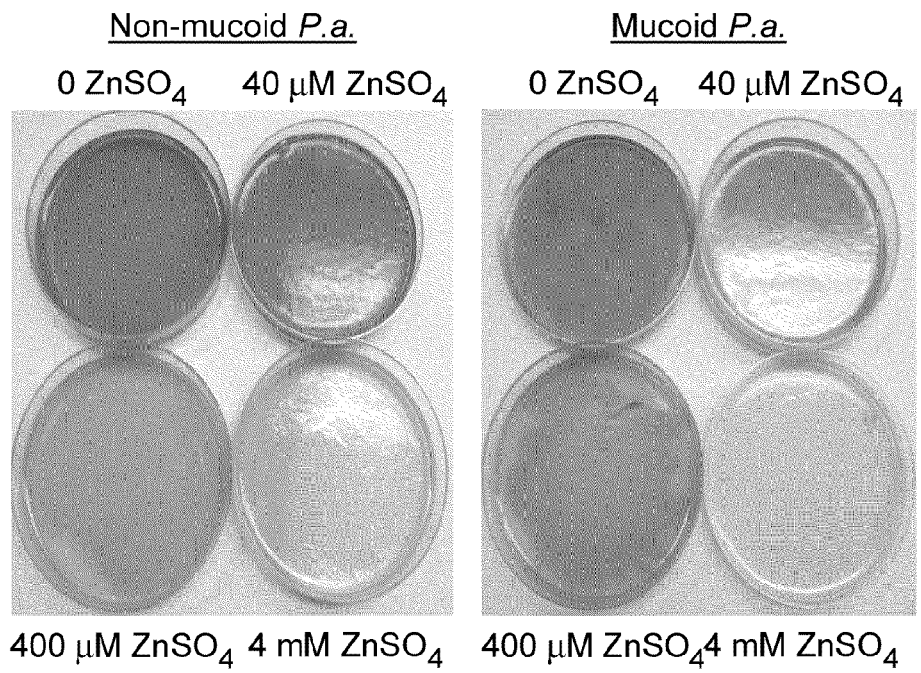
FIG. 11A shows marked inhibition of a non-mucoid and mucoid *Pseudomonas aeruginosa* lab strain by pharmacy-grade zinc sulfate. Zinc sulfate, normally prescribed as an adjunct therapy for Wilson's disease, was added to liquid LB-agar in known concentration before the agar hardened. An incomplete lawn of lighter color was seen with the micromolar doses of zinc sulfate. Only patchy and incomplete growth was observed for both non-mucoid and mucoid *P. aeruginosa* with the 4 mM dose of ZnSO4 RX.
Figure 11B:
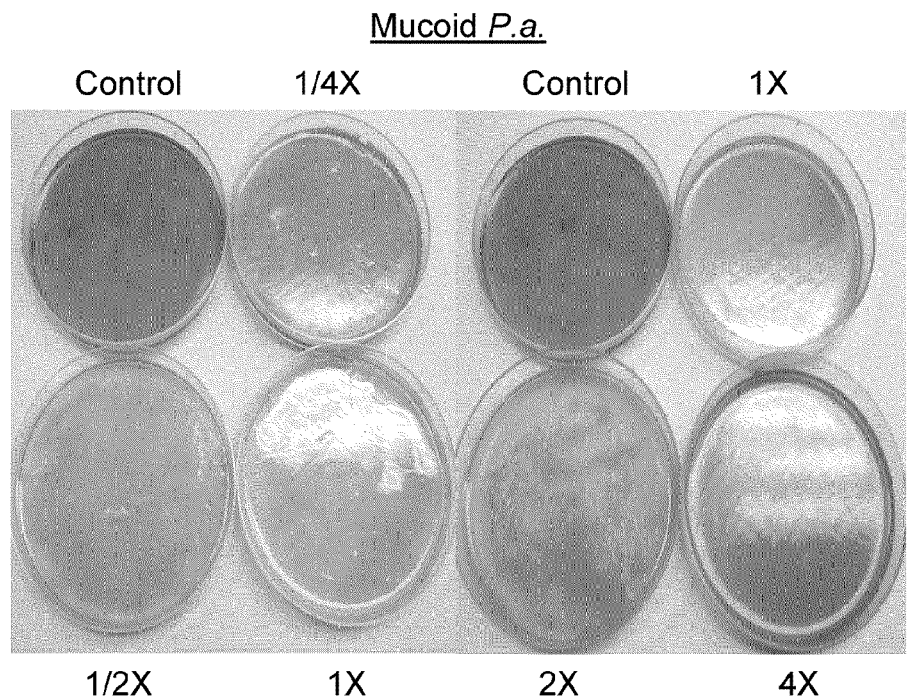
FIG. 11B shows marked inhibition of a mucoid *P. aeruginosa* lab strain by ColdEeze™. Zinc gluconate-containing ColdEeze was dried, ground with a mortar and pestle into small pieces, and the small pieces were solubilized into LB-agar medium (the 1× concentration was 5 grams of ColdEeze or 1 lozenge in 100 mls of LB medium) and poured on plates before agar hardening. The dark brown color is indicative of a fully-grown lawn of mucoid *P. aeruginosa*. Only patchy growth was observed in 1× ColdEeze, while no growth was observed on a 4× ColdEeze plate. For FIGS. 11A and 11B, all cultures were grown in a 37° C. warm room for 20 hours. The dark green color is indicative of a fully-grown lawn of non-mucoid *P. aeruginosa* that has used up all of the iron in the LB-agar and has released its siderophores in excess to scavenge more. The color change in the cultures was also blunted, if not prevented. The dark orange/brown color is indicative of a fully-grown lawn of mucoid *P. aeruginosa* that becomes darker as the lawn matures. Note that only patchy and incomplete growth was observed for both non-mucoid and mucoid *P. aeruginosa*.
Figure 11C:
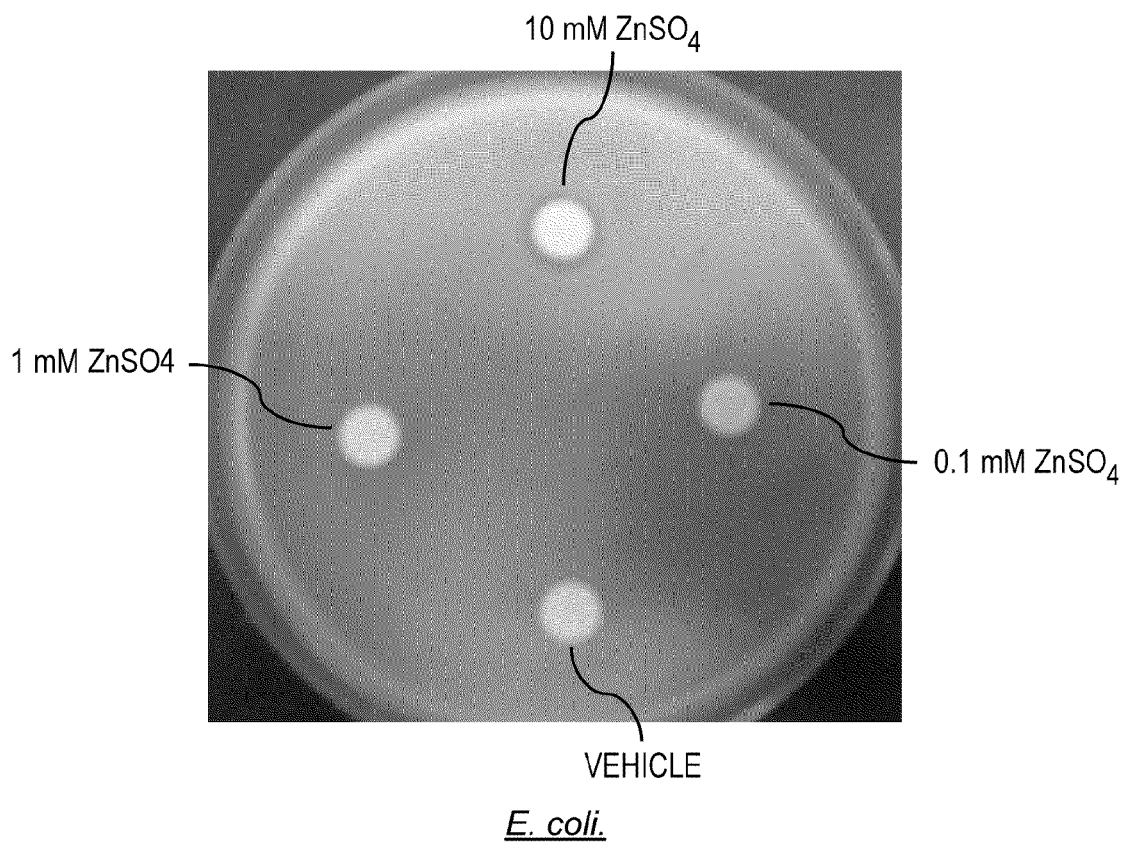
In FIG. 11C, top agar overlay experiments were performed where bottom agar served as the growth medium and the top agar contained a log-phase growth culture of a bacterial pathogen. A sterile disc soaked in a zinc formulation or in vehicle was inlaid in the top agar. Halos of clear top agar where bacteria are not present was indicative of diffusion of the zinc into the top agar from the disc and bacterial killing. Significant halos observed with zinc sulfate in millimolar concentrations as well as Zicam nasal gel and ColdEeze in concentrated form for both non-mucoid and mucoid *P. aeruginosa*, *E. coli.*, and the Steme strain of *Bacillus anthracis*. Marked inhibition of non-mucoid *Pseudomonas aeruginosa* lab strain Pa01 growth by the over-the-counter cold remedy Zicam™ nasal gel was also observed. Swabs laden with the zinc gluconate-containing nasal gel were dipped into bacterial cultures for fixed time periods or were added to the cultures during growth incubations. The latter proved more effective, as it inhibited growth in a dose-dependent manner. The OD control was a bacterial culture inoculated as the others with bacteria but then placed at 4° C. All cultures were grown at 37° C. with gentle shaking. Marked inhibition of growth of a mucoid *Pseudomonas aeruginosa* lab strain was also observed with Zicam™. Marked inhibition of non-mucoid and mucoid *Pseudomonas aeruginosa* by Zicam™ was also observed when the zinc gluconate-containing nasal gel was squirted onto plates before 25 mls of liquid LB-agar was poured into them. The nasal gel was then mixed well with the liquid before the agar hardened. All cultures were grown in a 37° C. warm room for 20 hours. The dark green color is indicative of a fully-grown lawn of non-mucoid *P. aeruginosa* that has used up all of the iron in the LB-agar and has released its siderophores in excess to scavenge more. The dark orange/brown color is indicative of a fully-grown lawn of mucoid *P. aeruginosa* that becomes darker as the lawn matures. Note that only patchy and incomplete growth was observed for both non-mucoid and mucoid *P. aeruginosa* with the 12 squirts of Zicam nasal gel. The color change in the cultures was also blunted, if not prevented. Similar inhibition of non-mucoid and mucoid *Pseudomonas aeruginosa* lab strain Pa01 was observed with the over-the-counter cold remedy, Cold-Eeze™. LB medium containing 1× Cold-Eeze (5 grams of Cold-Eeze solubilized with heat in 100 mls of LB medium) or more diluted concentrations inhibited growth markedly. Higher concentrated stocks of Cold-Eeze contained too much red dye and changed the color of the growth cultures, adversely affecting OD readings. Cultures were grown as described above.
Figure 12A:
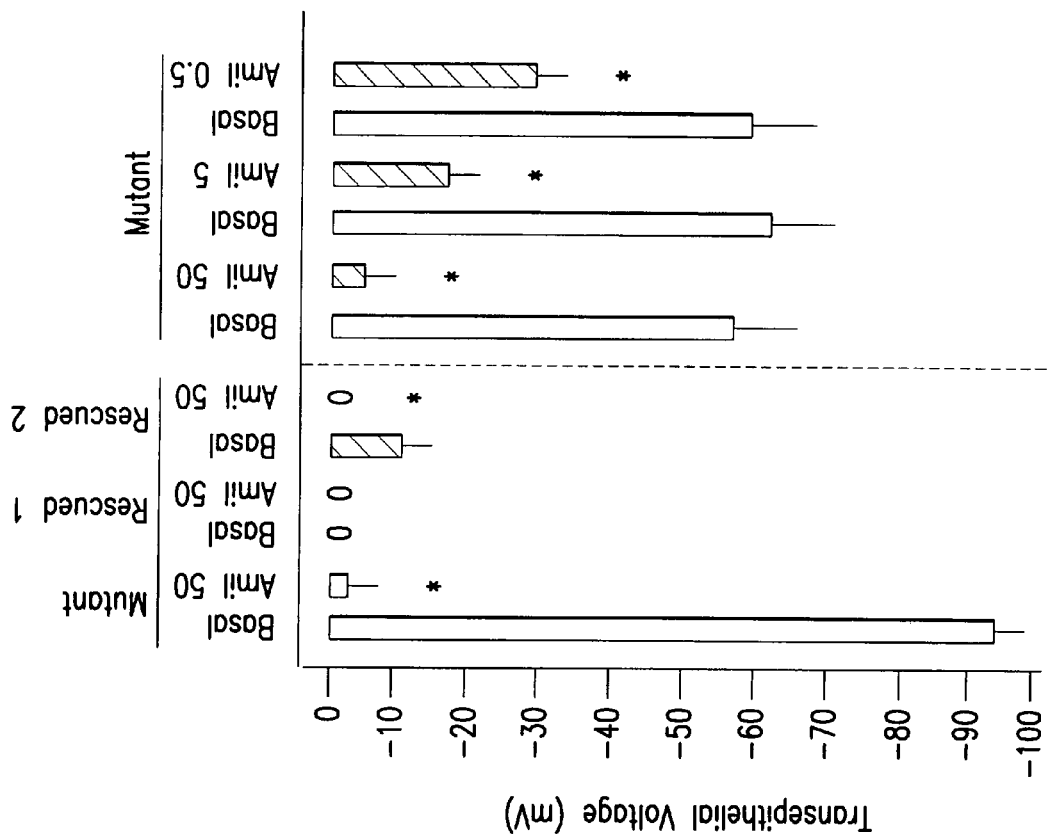
FIGS. 12A and 12B show ENaC-selective amiloride analogs inhibit upregulated voltage and current in PKD mutant monolayers. Ten micromolar was the dose used for each amiloride analog. *$P<0.05$ or lower for ISC data at left. *$P<0.01$ or lower for open-circuit data at right. Amiloride analog doses are micromolar. N is shown for ISC data; n=24 for the amiloride dose-response set of VTE data and n=12-24 for the amiloride analogs. It was also observed that serine protease inhibitors attenuate the upregulated voltage and current in PKD mutant monolayers. At right, aprotinin was diluted from its 10 μg/ml working dose. Inhibition was only gauged to be significant in mutant monolayers. n=12 for data sets at right. Full inhibition took 30 minutes to occur in PD assays. This was another diagnostic feature that suggested that ENaC sodium channels were upregulated and caused sodium hyperabsorption in PKD.
Figure 12A:
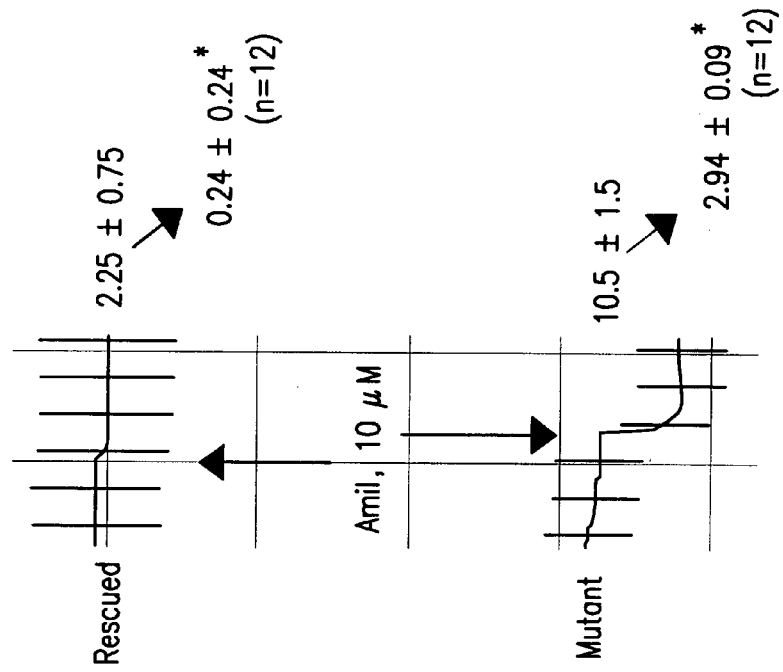
Figure 12B:
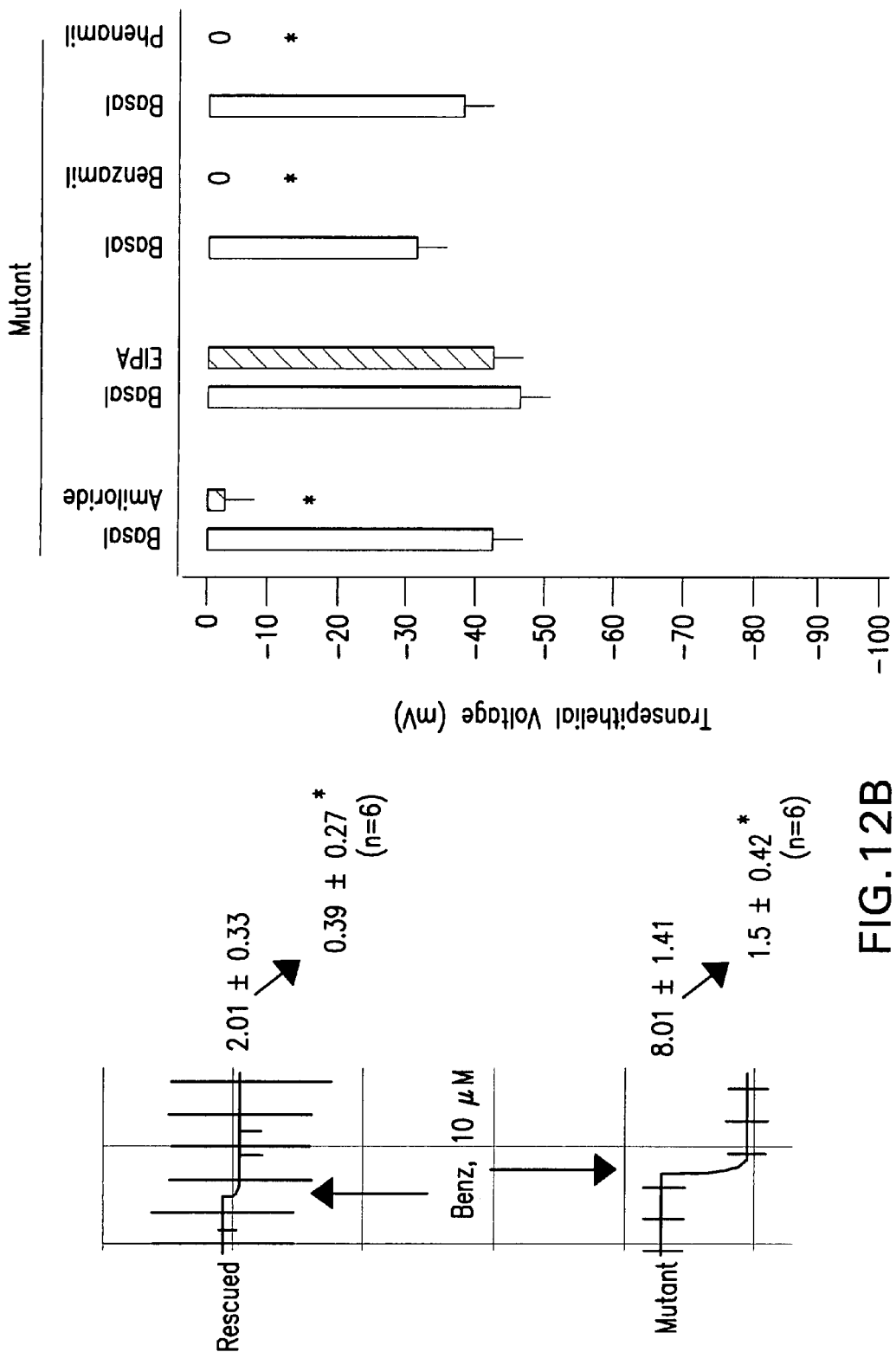
Figure 13A:
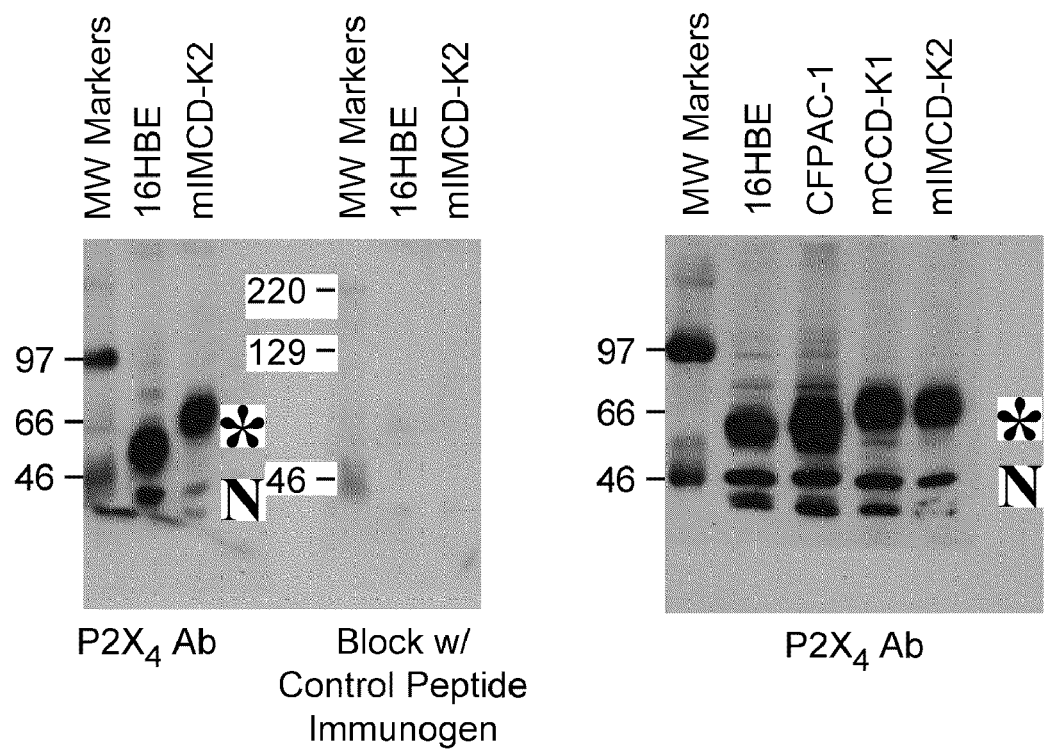
FIG. 13A shows immunoblots showing expression of P2X4 in kidney collecting duct epithelial cell lines as well as human airway and pancreatic epithelial cell lines. Both non-glycosylated and glycosylated forms are shown.
Figures 1, 13B:
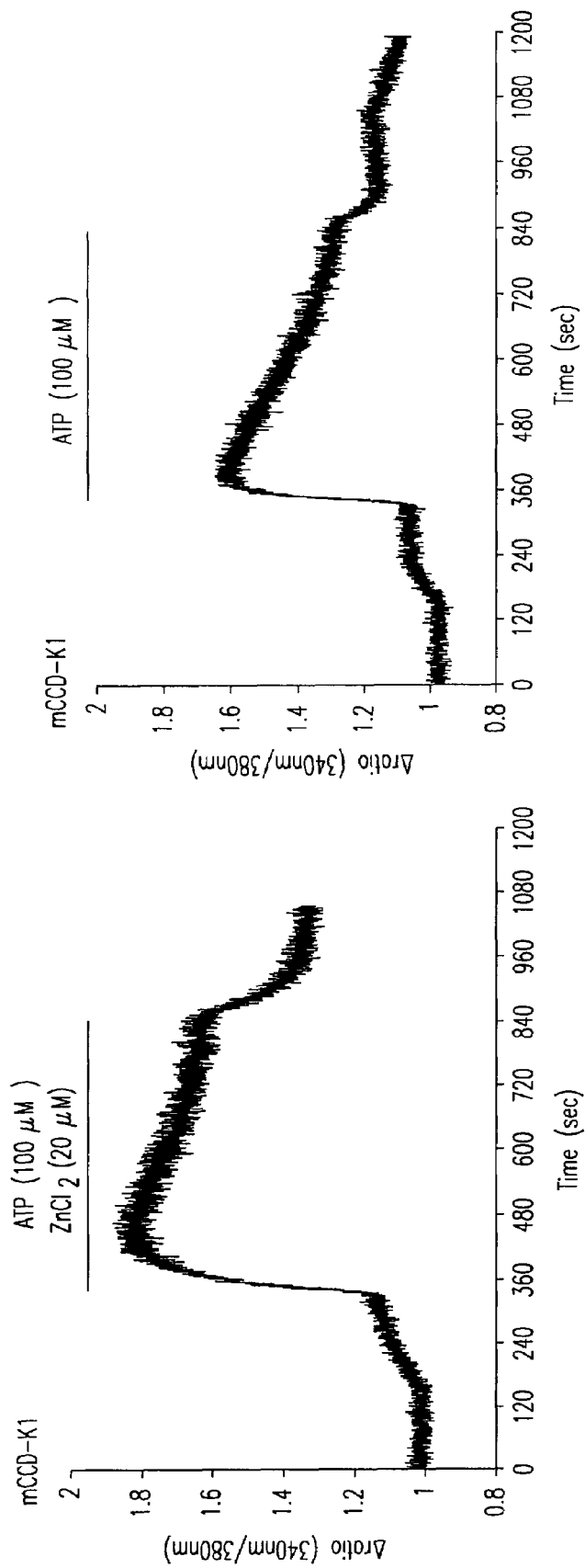
FIG. 13B shows Fura-2 analysis of normal and polycystic kidney collecting duct cell models showing that extracellular zinc and/or ATP also increases cell calcium in a sustained manner due to calcium entry in both diseased and normal cells. Taken together, this figure shows mRNA and protein expression for therapeutic target in kidney collecting duct, the site of the most severe abnormalities in PKD, and that zinc and ATP, via opening of P2XRs, increases cell calcium in a sustained manner like they do in airway epithelia.
Figures 2, 13B:
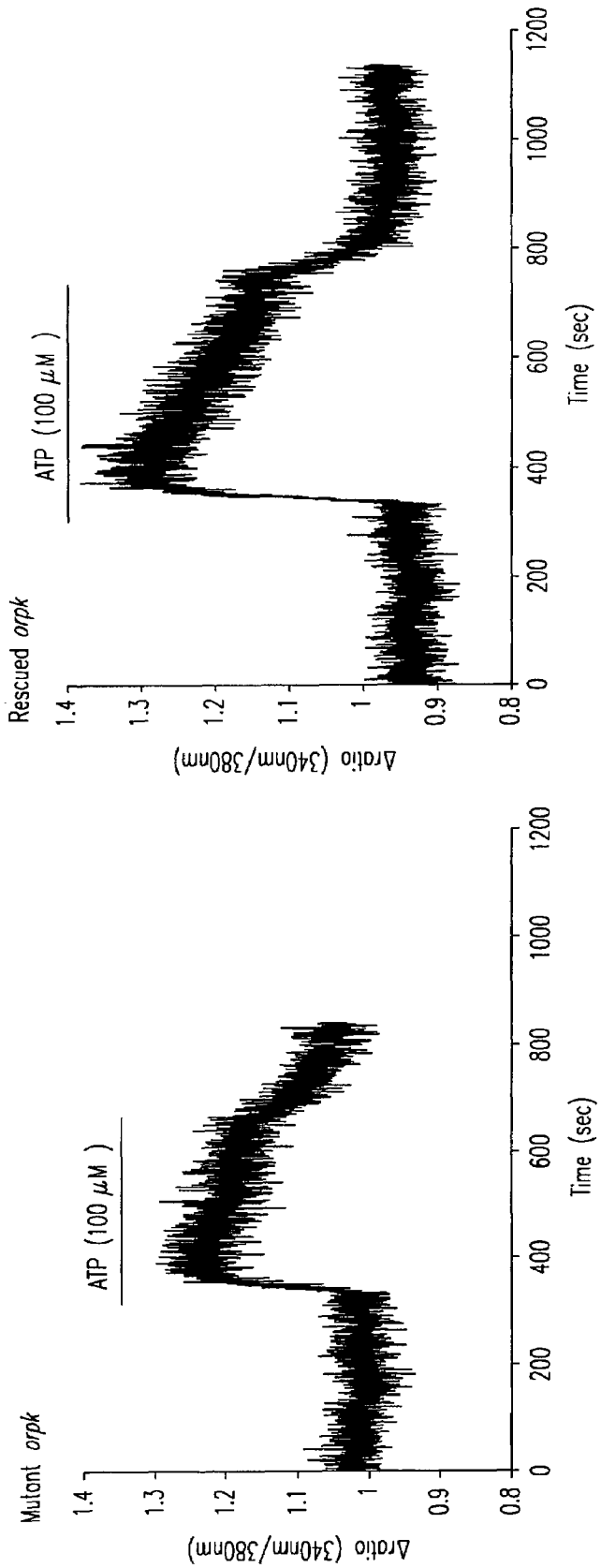
Figure 14A:
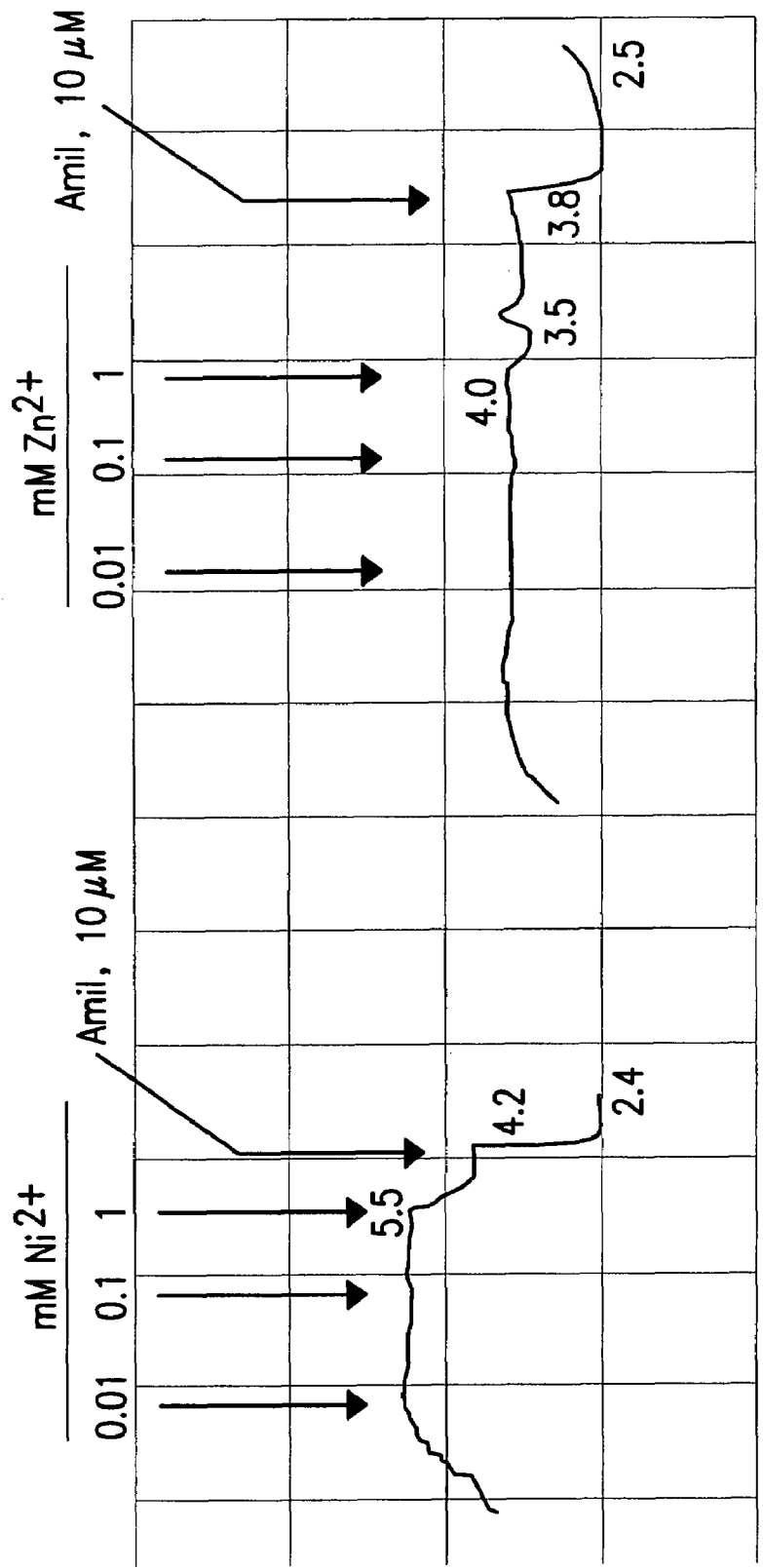
FIG. 14A shows ISC traces.
Figure 14B:
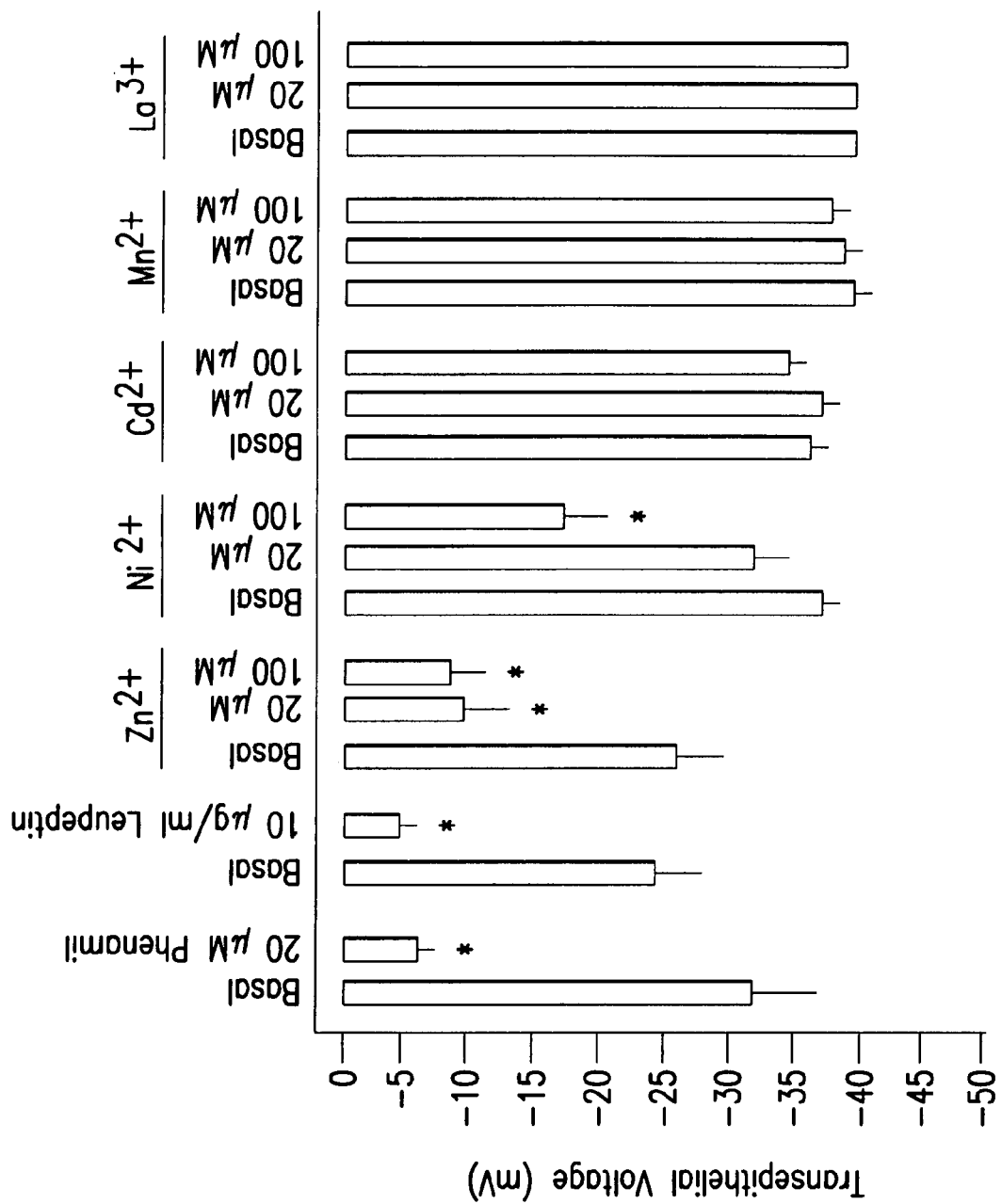
FIG. 14B shows VTE data. As another diagnostic tool for ENaC activity, typical experiments are shown illustrating the inhibitory effects of the biometals, nickel and zinc when compared to amiloride. The transient effect of zinc in ISC traces may reflect some stimulation of Cl− secretion in this epithelium; zinc is a potent agonist at apical eP2XRs that allow calcium entry and stimulation of airway epithelial Cl− channels. Millimolar concentrations were required for inhibition in ISC recordings, while mid-micromolar doses were inhibitory in PD assays. N=6 for each data set in A and B; *$P<0.05$.

Zinc alone or with ATP rescued Cl− efflux in IB3-1 CF cells by a halide-sensitive fluorescence dye (SPQ)-based assay. Also, zinc or nucleotide rescued regulatory volume decrease, a cell volume regulatory process, following hypotonic cell swelling in IB3-1 CF cells that have defective RVD rates and magnitude. Zinc and ATP also stimulated chloride and bicarbonate transport across non-CF and CF human airway epithelial cell monolayers in Ussing chamber analysis. This correlates with the in vivo nasal potential difference data in vivo efficacy and translation of these potential therapeutic ligands, zinc and ATP, activating P2XRs to rescue defective chloride secretion in CF (FIG. 8).

Example 20

Multiple Zinc Formulations are Bacteriastatic for Non-Mucoid and Mucoid *Pseudomonas aeruginosa*

Marked inhibition of non-mucoid Pseudomonas aeruginosa lab strain Pa01 growth by the over-the-counter cold remedy Zicam™ nasal gel was observed. Swabs laden with the zinc gluconate-containing nasal gel were dipped into bacterial cultures for fixed time periods or were added to the cultures during growth incubations. The latter proved more effective, as it inhibited growth in a dose-dependent manner. The OD control was a bacterial culture inoculated as the others with bacteria but then placed at 4° C. All cultures were grown at 37° C. with gentle shaking. Marked inhibition of growth of a mucoid *Pseudomonas aeruginosa* lab strain was also observed with Zicam™. Marked inhibition of non-mucoid and mucoid *Pseudomonas aeruginosa* by Zicam™ was also observed when the zinc gluconate-containing nasal gel was squirted onto plates before 25 mls of liquid LB-agar was poured into them. The nasal gel was then mixed well with the liquid before the agar hardened. All cultures were grown in a 37° C. warm room for 20 hours. The dark green color is indicative of a fully-grown lawn of non-mucoid *P. aeruginosa* that has used up all of the iron in the LB-agar and has released its siderophores in excess to scavenge more. The dark orange/brown color is indicative of a fully-grown lawn of mucoid *P. aeruginosa* that becomes darker as the lawn matures. Only patchy and incomplete growth was observed for both non-mucoid and mucoid *P. aeruginosa* with the 12 squirts of Zicam nasal gel. The color change in the cultures was also blunted, if not prevented. Similar inhibition of non-mucoid and mucoid *Pseudomonas aeruginosa* lab strain Pa01 was observed with the over-the-counter cold remedy, Cold-Eezem. LB medium containing 1× Cold-Eeze (5 grams of Cold-Eeze solubilized with heat in 100 mls of LB medium) or more diluted concentrations inhibited growth markedly. In general, zinc formulations inhibited the growth (bacteriastatic) at lower concentrations (0.01 to 1 mM) and were bacteriacidal at higher concentrations (1-100 mM) for avirulent strains of *E. coli*, *Bacillus anthracis* (anthrax), and *Bacillus subtilis* in addition to non-mucoid and mucoid *Pseudomonas*. The effects of zinc were similar in terms of bacteriastatic and bacteriacidal effects on all bacterial pathogens tested to date.

Example 21

Figure 15A:
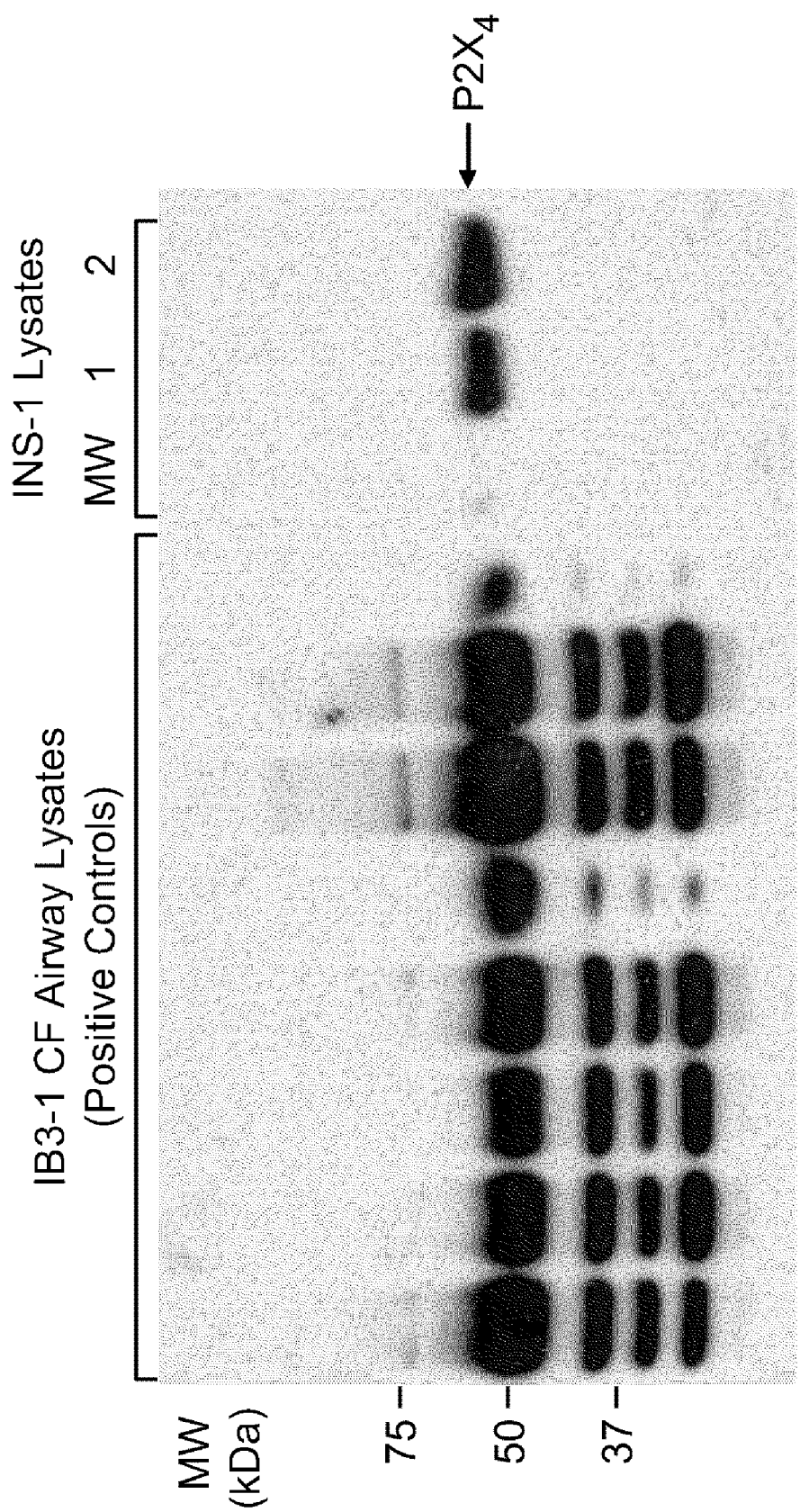
FIG. 15A shows an immunoblot showing expression of the glycosylated form of the P2X4 receptor channel subtype in the INS-1 rat pancreatic beta cell line in parallel with IB3-1 human airway epithelial cell line positive controls. These data are similar to biochemical Western blot analysis in airway, pancreatic, and kidney epithelial cell lines above.
Figure 15B:
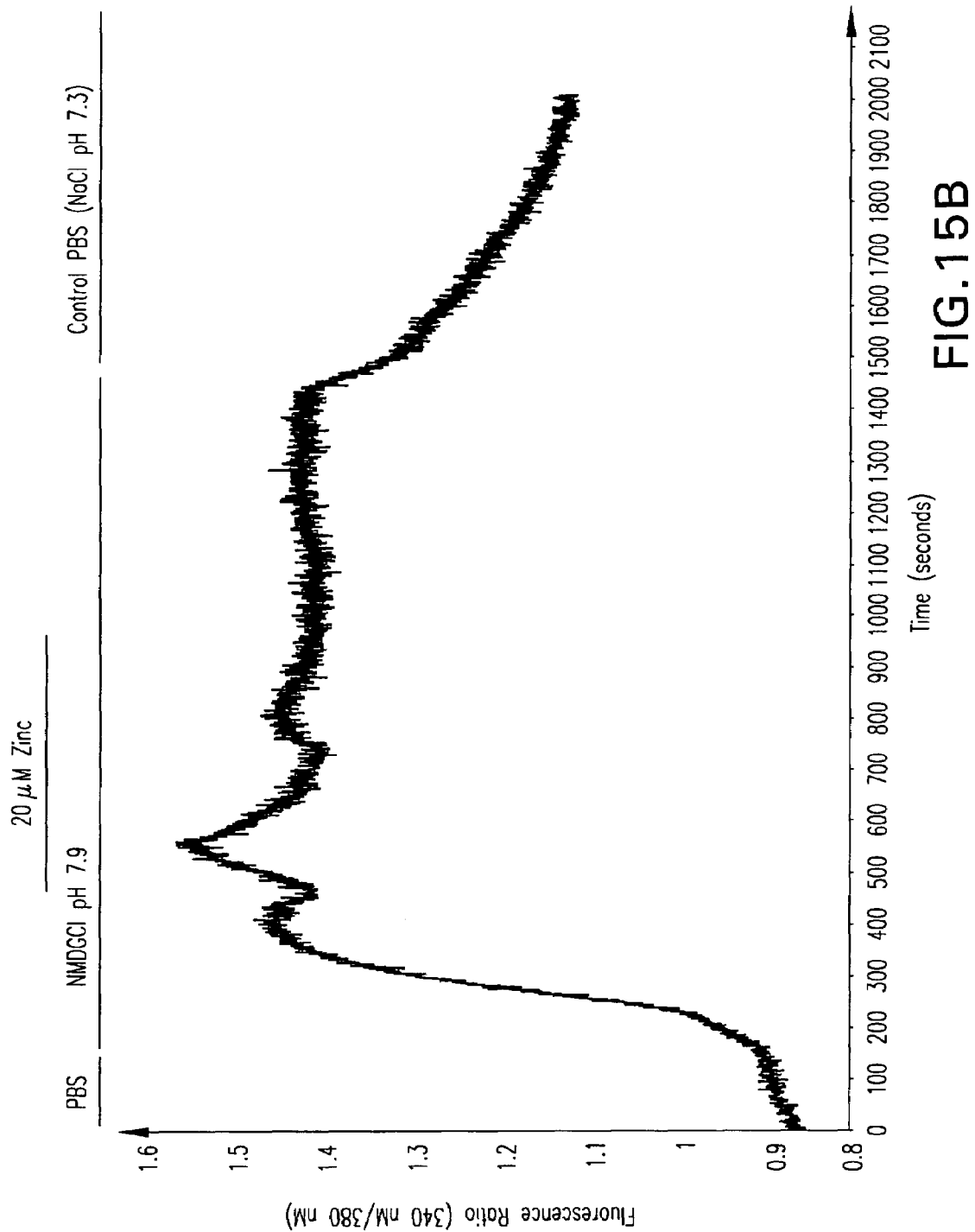
FIG. 15B shows solution changes with regard to ionic content and pH augment calcium entry in INS-1 rat pancreatic β cells. Fura-2 fluorescence assay shows that a solution switch from a standard NaCl-containing Ringer (pH 7.3) to a sodium-free NMDGC1 Ringer (pH 7.9) led to a large and sustained rise in cell calcium that was reversible upon adding back NaCl Ringer. Addition of zinc led to a small transient increase above the sustained plateau. The sustained calcium signal was partially reversed by adding back NaCl-containing Ringer.
Figure 16B:
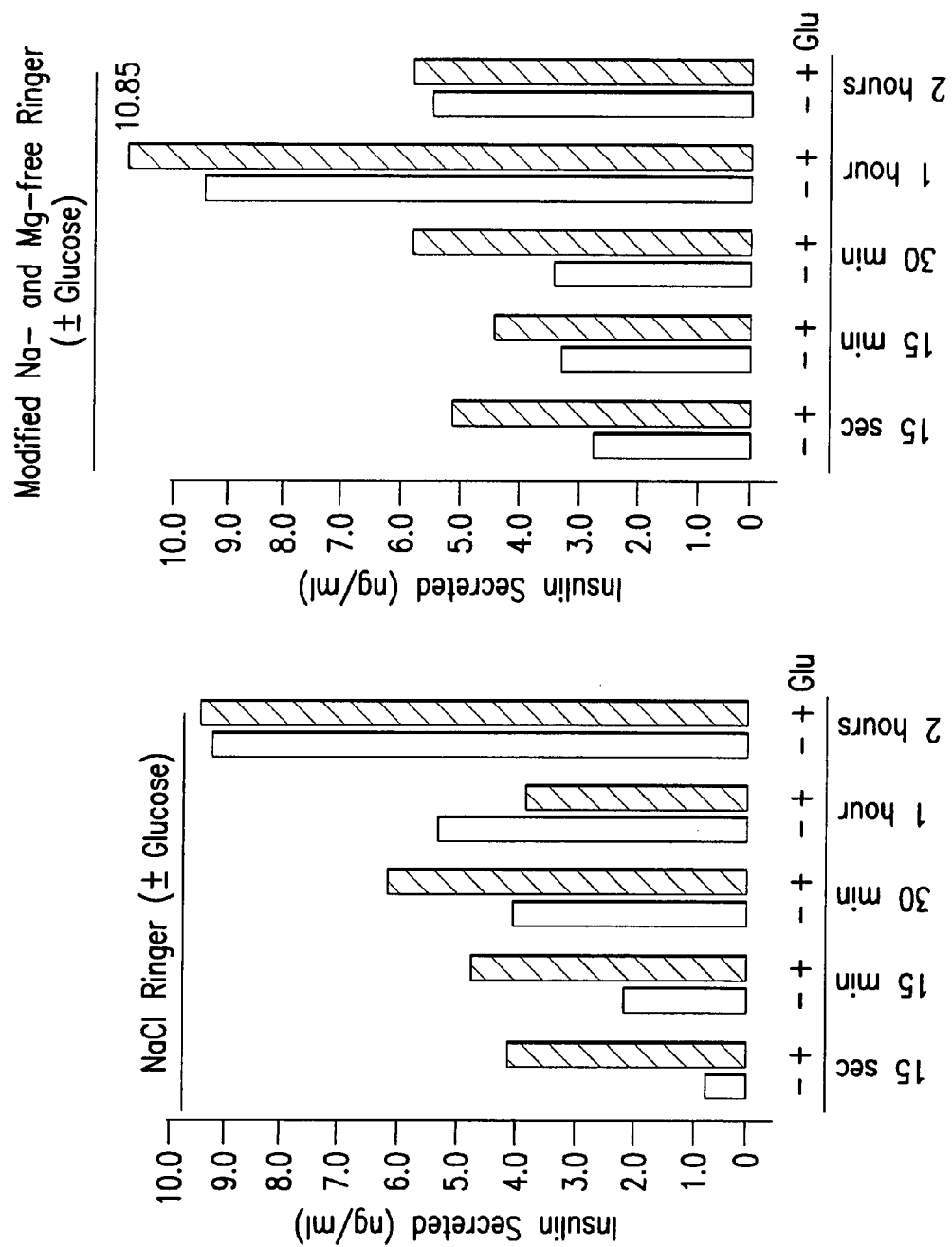
FIG. 16B is a graph showing that glucose stimulates insulin secretion at the earlier timepoints between 15 seconds post-start of incubation through 30 minutes to 1 hour in sodium-containing or sodium- and magnesium-free Ringer. The amount of insulin secreted was greater throughout the timecourse in the sodium- and magnesium-free Ringer.
Figure 17A:
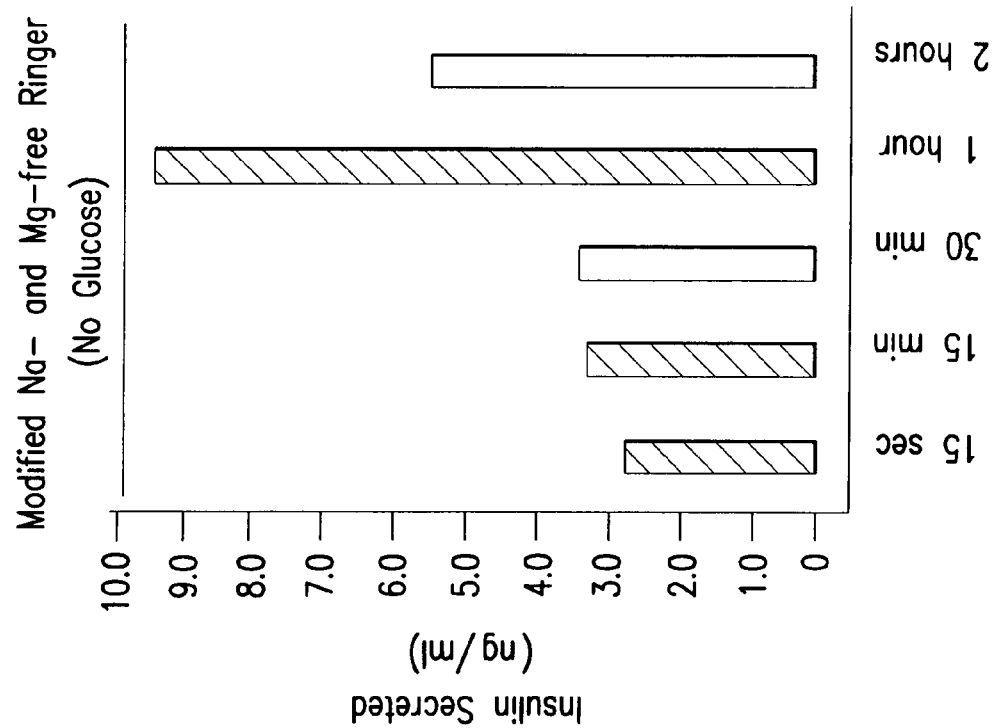
FIG. 17A shows a comparison between a standard NaCl-containing Ringer and a sodium- and magnesium-free Ringer independent of a glucose stimulus. The modified Ringer, shown above in Fura-2 calcium entry assays for epithelial cells and β cells to potentiate calcium entry, augmented insulin secretion under basal conditions in the very early phase of the time course as well as at the 1 hour timepoint (whereas the signal was less at the 2 hour timepoint).
Figure 17A:
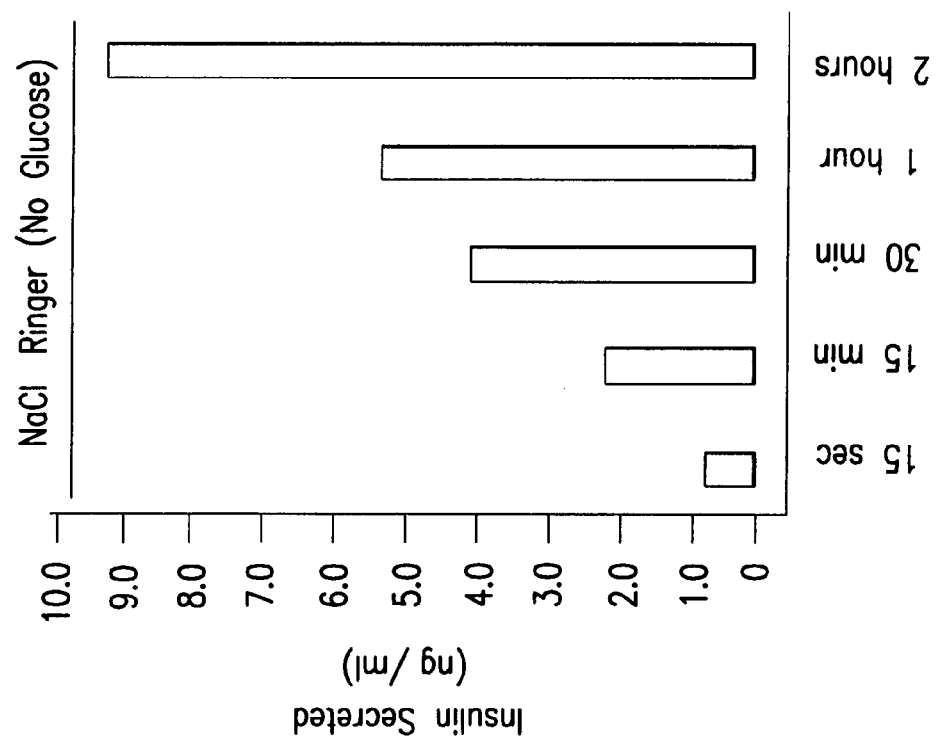
Figure 17B:
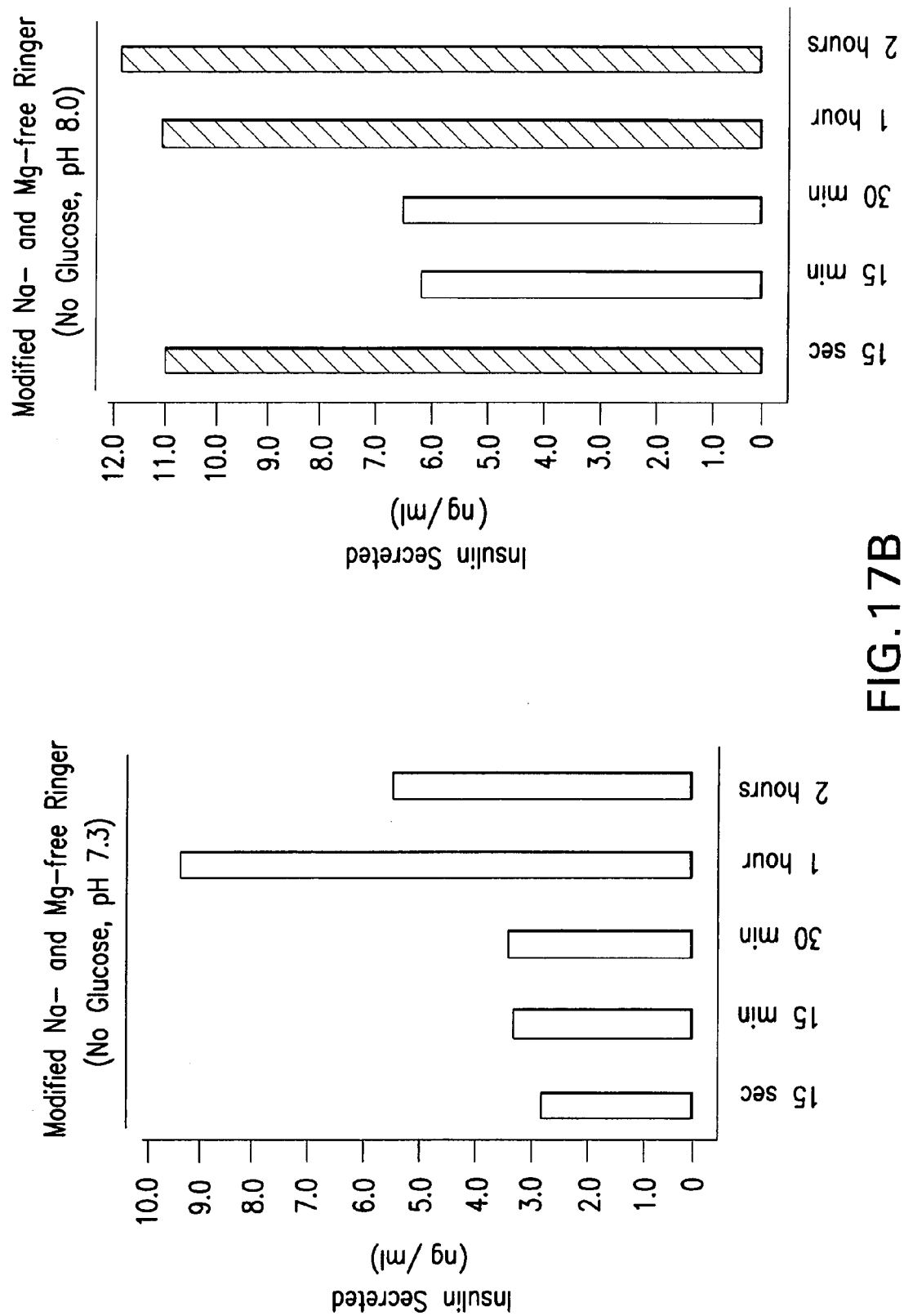
FIG. 17B shows a test of Ringers at neutral pH (7.3) and pH 8.0 on insulin secretion, based upon the increase in calcium entry at an alkaline pH. An alkaline pH solution stimulated insulin secretion at all timepoints versus neutral pH, but significantly at both the immediate peak of insulin secretion and the later peak of insulin secretion 1-2 hours post-stimulus.
Figure 18A:
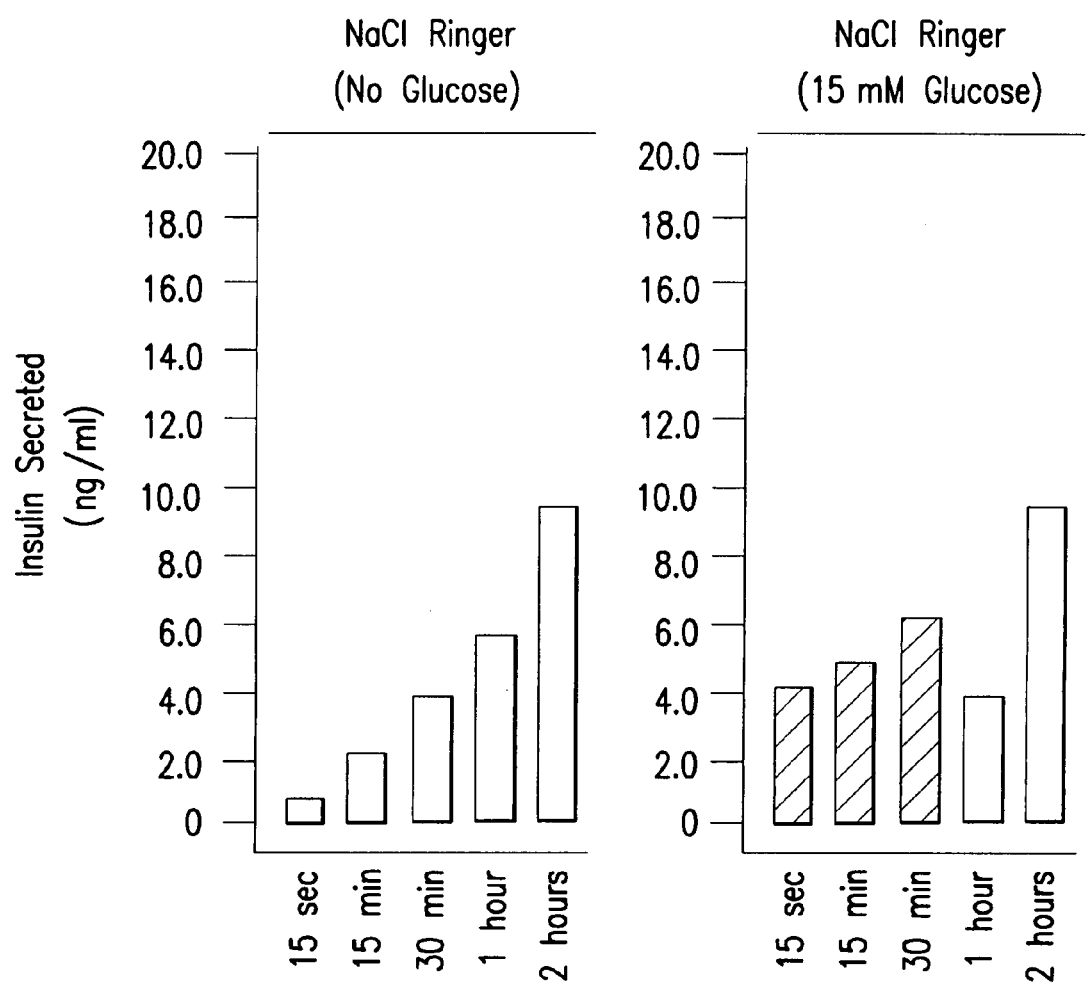
FIG. 18 shows the effects of zinc versus the glucose stimulus on insulin secretion. The filled bars show significantly greater insulin detected versus control. Glucose is an excellent stimulus for the initial immediate peak of insulin secretion. The glucose stimulus was compared with a zinc stimulus and also challenged with both glucose and zinc stimuli. Zinc was an even more potent stimulus than glucose at all timepoints with the exception of the timepoint 15 seconds after stimulation. There was an additive effect of both glucose and zinc, showing that they stimulate separate but additive calcium entry mechanisms to promote insulin secretion.
Figure 18B:
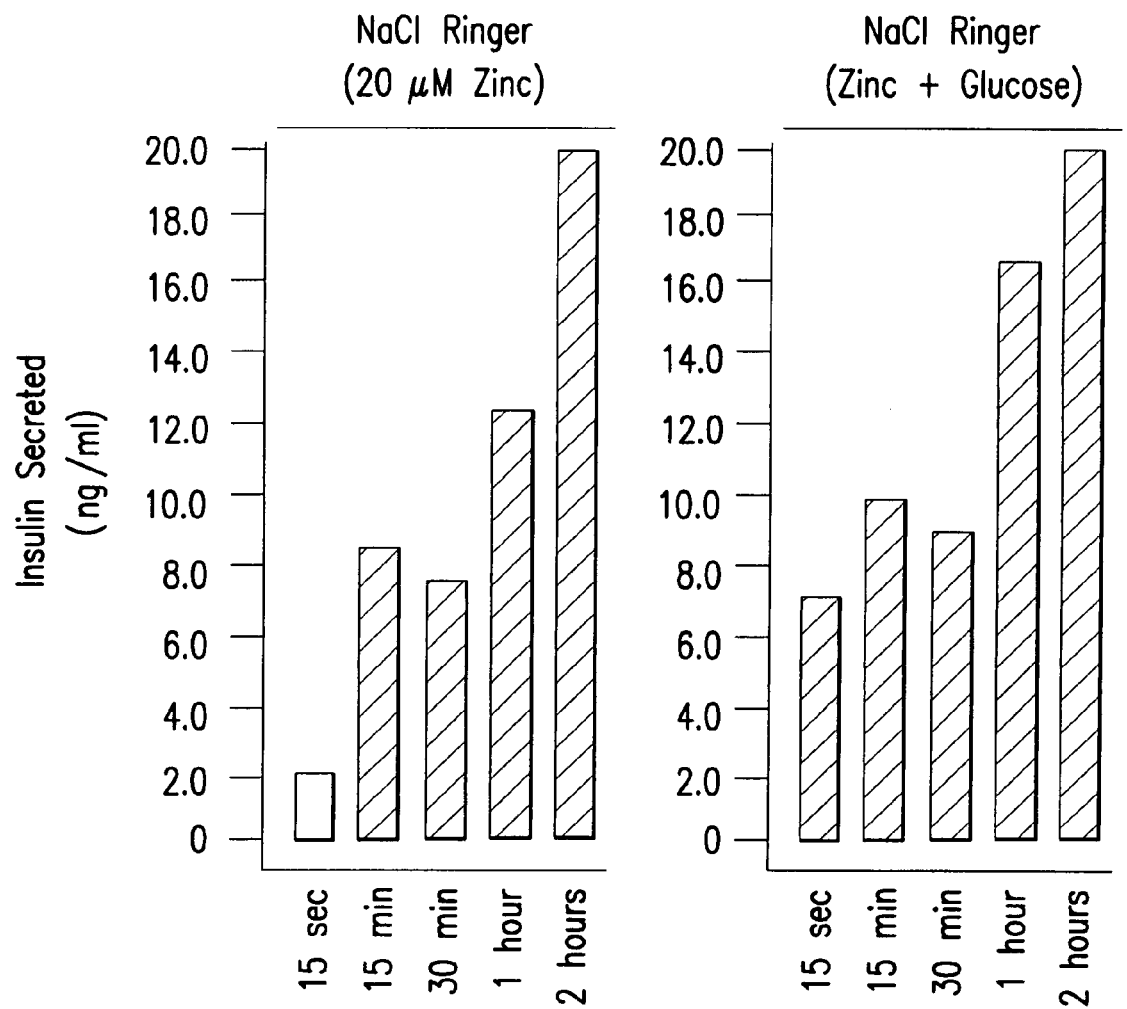
Figure 19A:
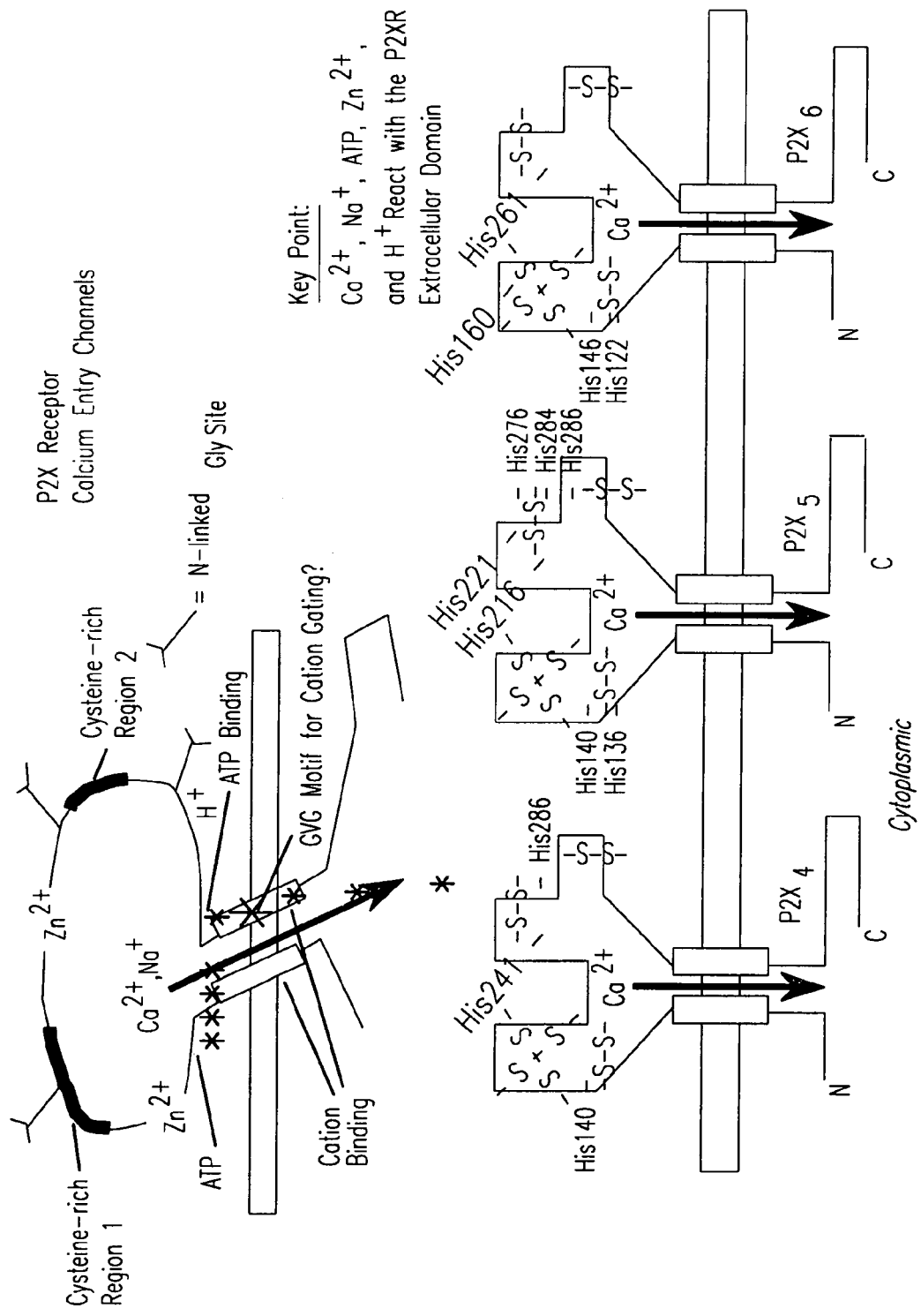
FIG. 19A shows a model of a generic P2XR structure by itself, illustrating that the receptor binds zinc, ATP, and protons in its extracellular domain and that it can also bind and conduct calcium and sodium ions across the membrane as an ion channel. The three P2X receptor calcium entry channel subtypes (P2X4, P2X5, and P2X6) are expressed in airway epithelia. Zinc and ATP in modified saline solution can stimulate the P2XR channel complex.
Figure 19B:
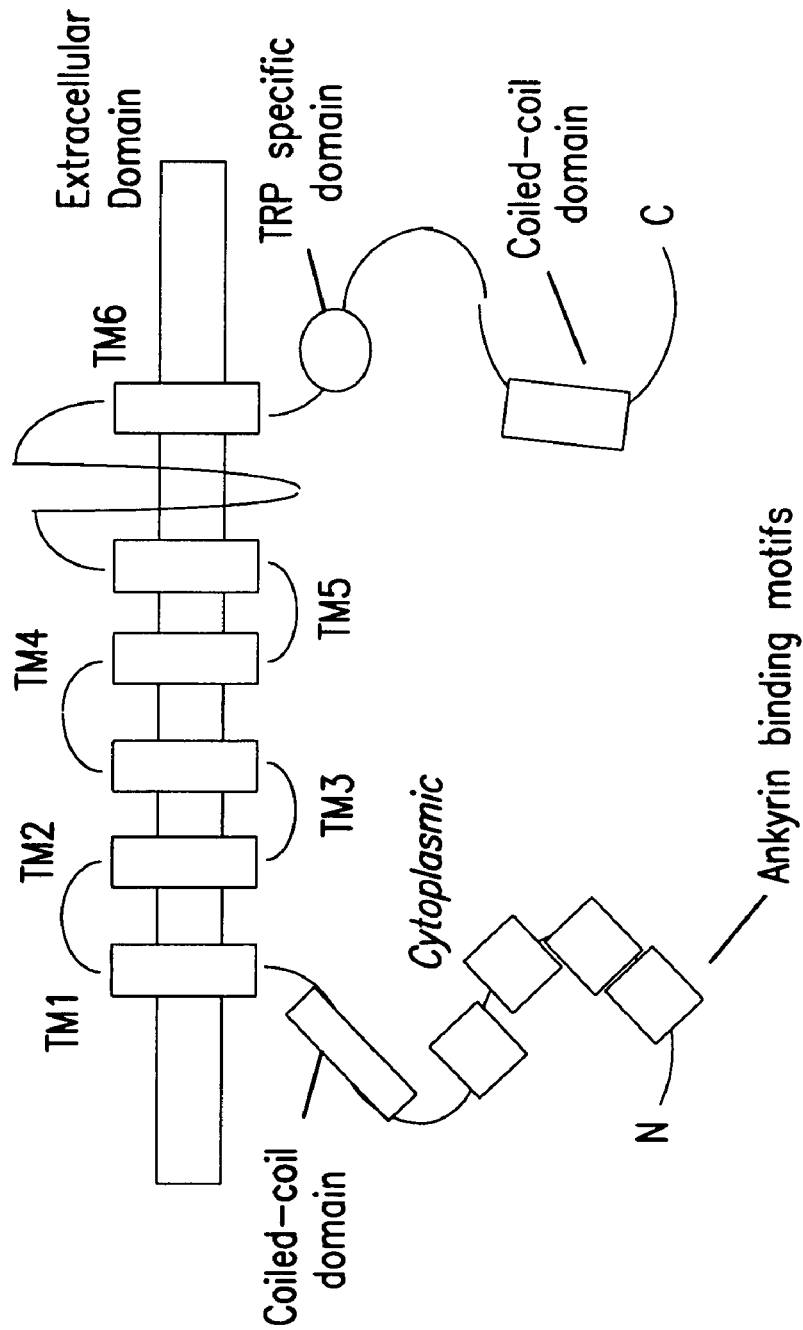
FIG. 19B shows the structure of the Transient Receptor Potential (TRP) calcium entry channel. In contrast to the P2X receptor calcium entry channels, TRP channels are store-operated calcium entry channels whose structure has most of the molecular mass of the channel protein intracellular, clustered at its amino- and carboxy-termini where there are multiple binding domains for intracellular signal transduction and structural scaffolding proteins.
Figures 1, 19C:
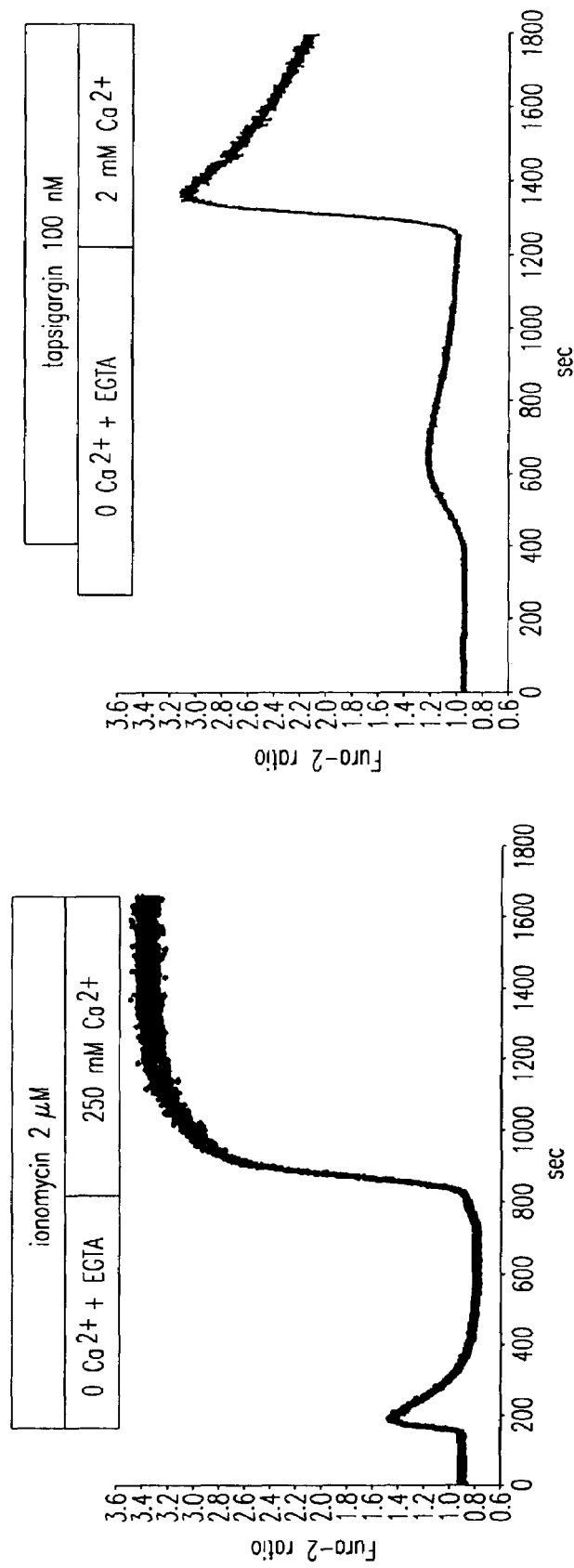
FIG. 19C shows examples of sustained calcium entry signals in mammalian cells. Shown are the ideal conditions for sustained increases in cytosolic calcium mediated by P2XR calcium entry channels and other calcium entry channels. Top left: the calcium ionophore, ionomycin (2 μM), increases Fura-2 fluorescence ratio to a value of 3.4 that is sustained. Top right: thapsigargin (100 nM) induced ER store depletion and re-addition of extracellular calcium activates store-operated calcium (SOC) channels transiently to a peak value of 3.0. Bottom left and right: effect of $Zn^{2+}$ alone or ATP plus $Zn^{2+}$ on sustained calcium entry to a value of 2.1 in Na+ free conditions and a mild alkaline pH of 7.9.
Figures 2, 19C:
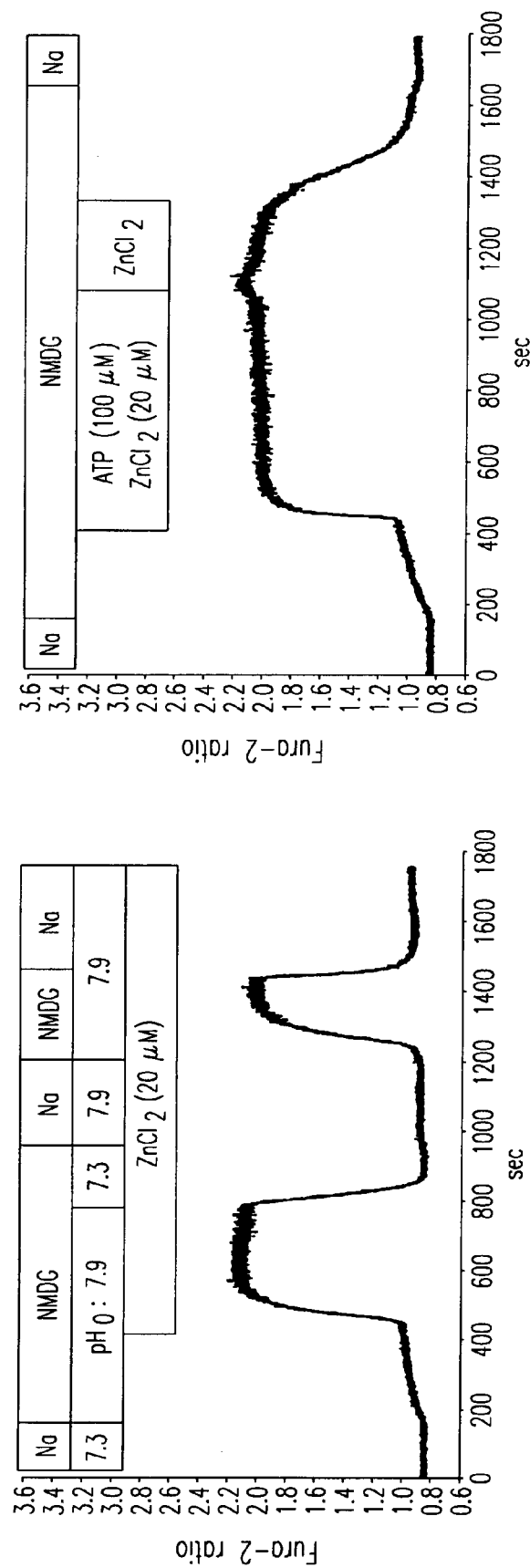
Figure 20A:
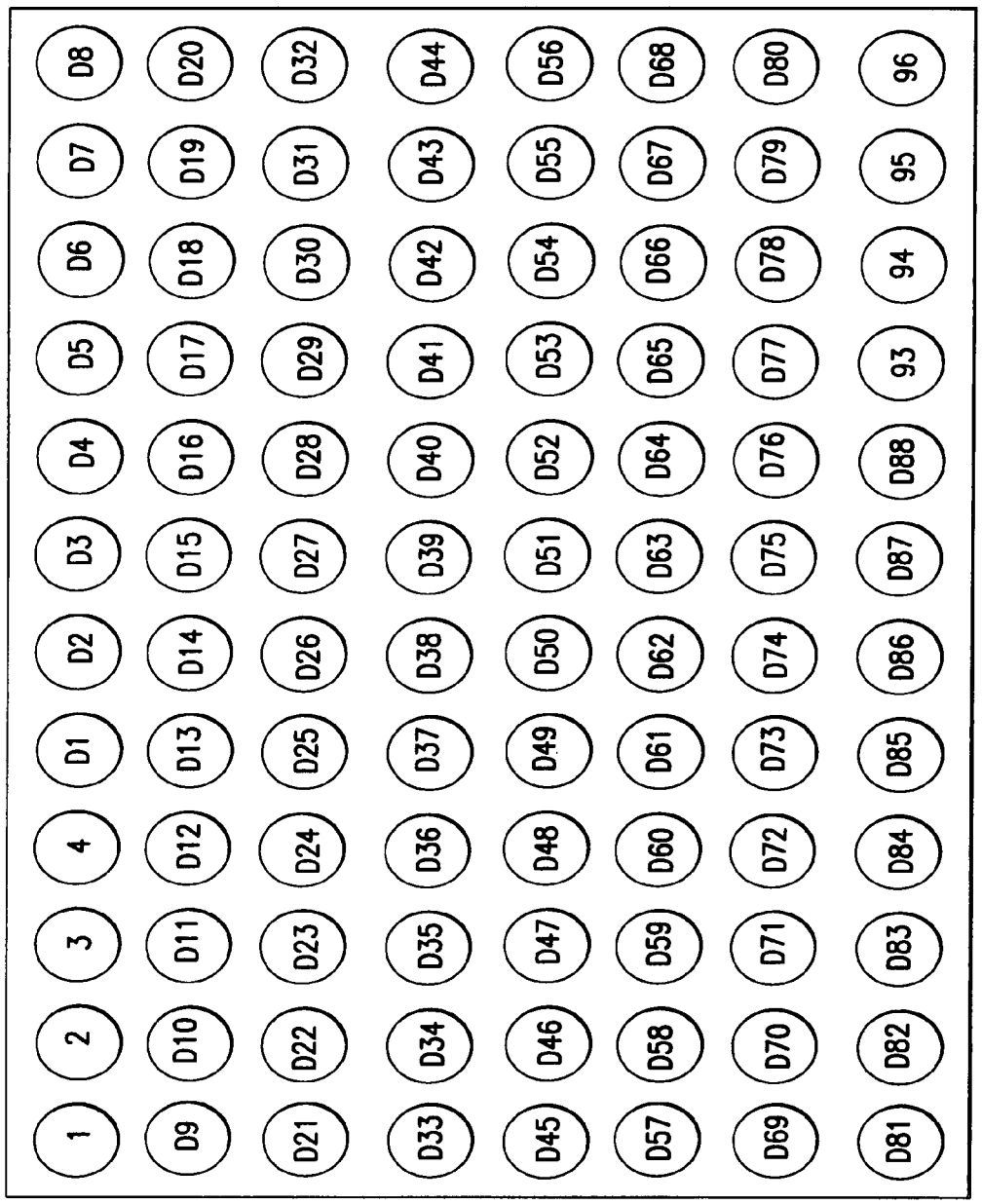
FIG. 20A shows the design of the CF primary HTS screen of ligands; one 96-well quadrant of a 384-well plate. Based on a screen of a 2,000 modified nucleotide ligand library available from SRI, lighter wells at the start and end of each 96-well quadrant are the wells where positive and negative controls are run. In wells 5 through 92, 88 separate and individual ligands are screened. This arrangement can repeated identically in the other 3 quadrants of the 384-well plate to have an n=4 on each drug after the initial screen is completed. Using this arrangement, 24 384-well plates are needed to screen the 2,000 molecule library.
Figure 20B:
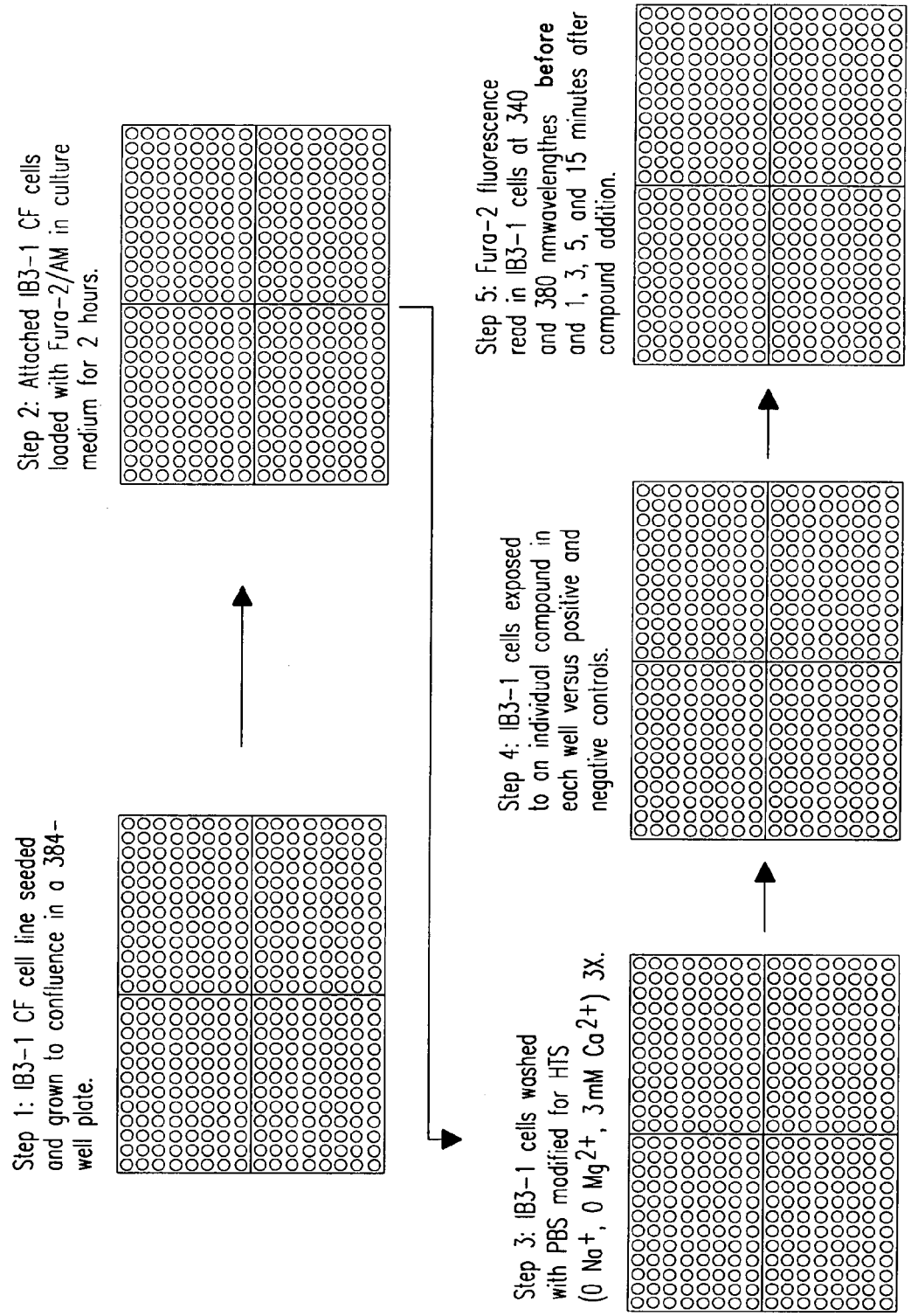
FIG. 20B shows step-wise description of the HTS screen in epithelial cells for new calcium entry channel ligands in respiratory and renal disorders. Each step for washing, loading of Fura-2 dye, challenging with new ligands (10 micromolar amount of each drug in the library), etc. is shown. Positive controls using zinc, zinc plus ATP, and the calcium ionophore, ionomycin, as well as negative controls in 0 extracellular calcium will be performed.
Figure 20C:
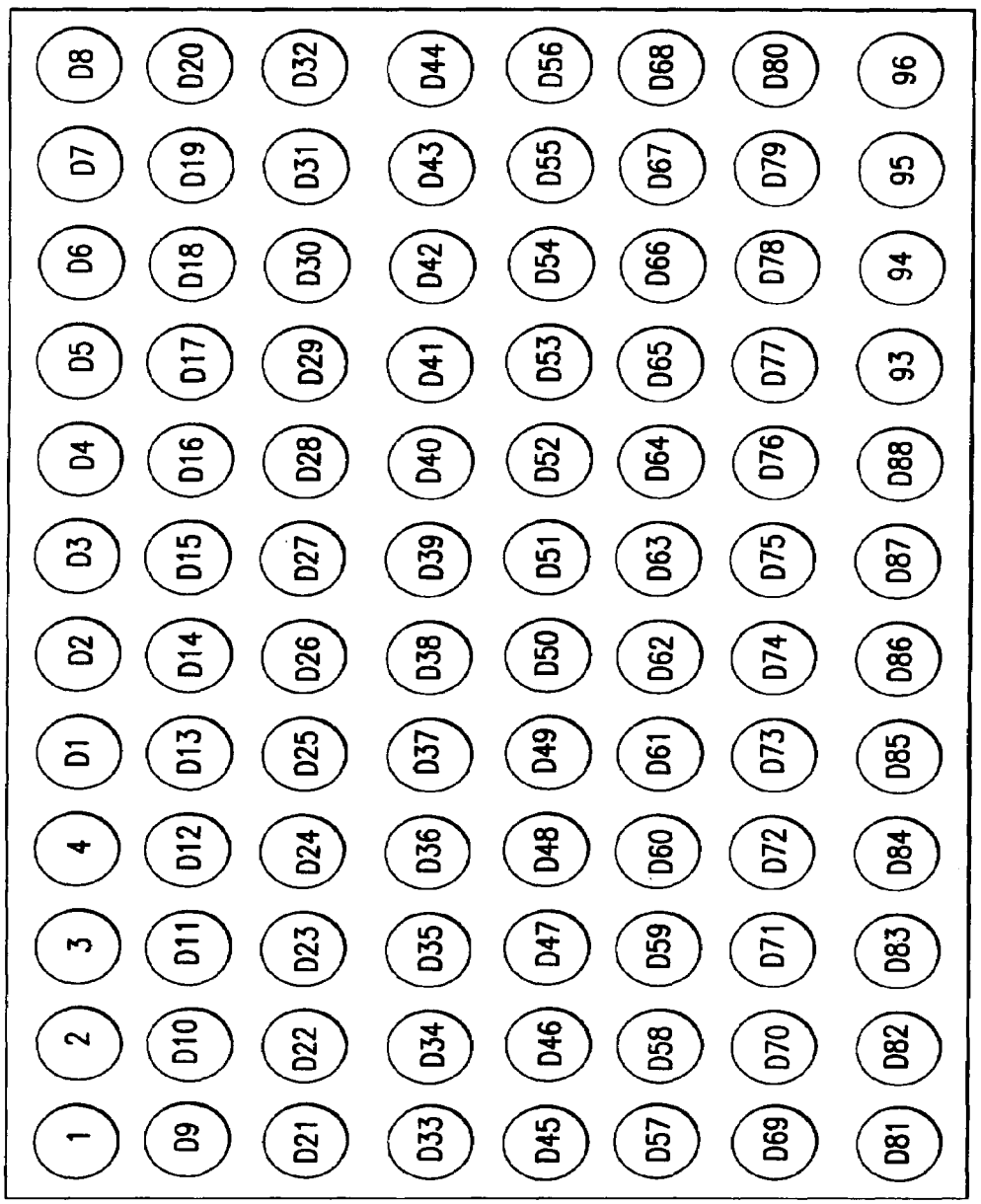
FIG. 20C shows the design of the diabetes primary HTS screen of ligands; one 96-well quadrant of a 384-well plate. Based on a screen of a 2,000 modified nucleotide ligand library, lighter wells at the start and end of each 96-well quadrant are the wells where positive and negative controls are run. In wells 5 through 92, 88 separate and individual ligands are screened. This quadrant can be assayed in the absence of 15 mM glucose. Where the HTS differs in the HTS for pancreatic β cells is that in the other 3 quadrants of the 384-well plate, 15 mM glucose is included in the saline in quadrant 2, 30 mM potassium chloride is included in quadrant 3 to depolarize the cells, and both glucose and KCl are included in quadrant 4. This is to determine whether a ligand induced calcium entry independent of glucose or voltage. Similar modifications can be made with regard to cell model used or experiments performed with regard to the different neuroendocrine or endocrine disorders listed.
Figure 20D:
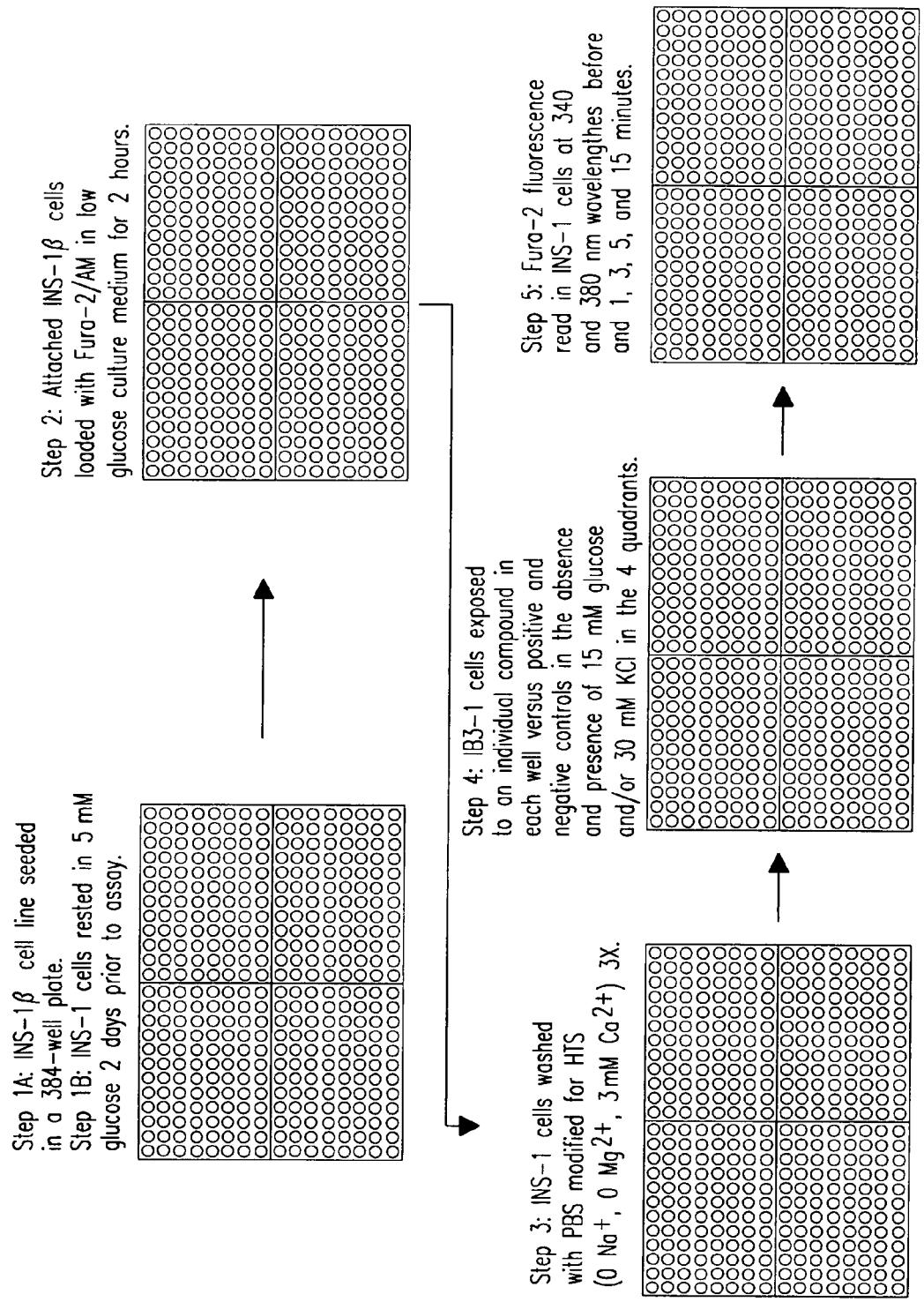
FIG. 20D shows a step-wise description of the HTS screen in pancreatic β cells for diabetes that can also be adapted to other endocrine disorders.
Figure 20E:
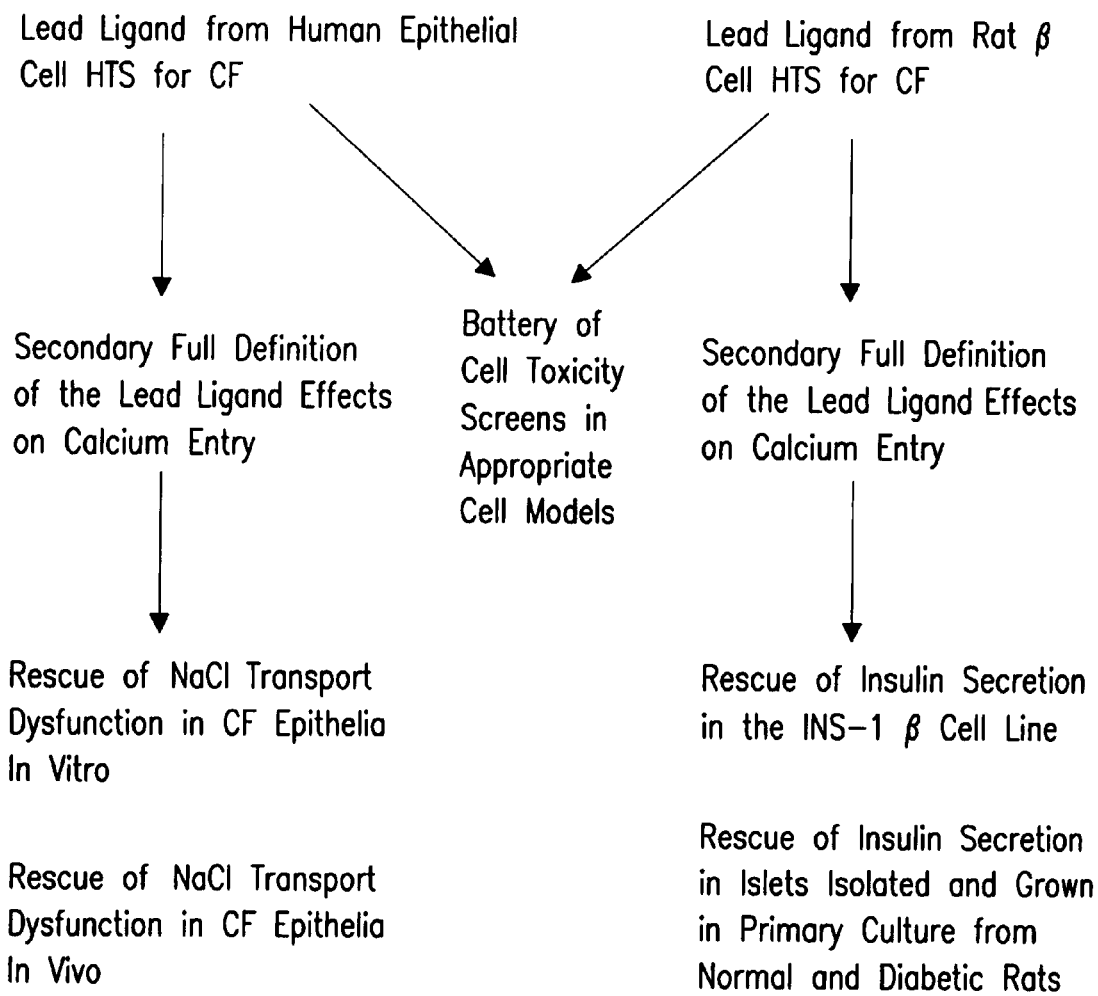
FIG. 20E shows a flow diagram of secondary screening for a lead calcium entry ligand in the context of CF and diabetes therapeutics. A full series of toxicity screens on epithelial cells, β cells, and other cell models are performed for apoptosis induction, cell viability, cell proliferation, etc. For CF and diabetes, a full definition of how a lead ligand augments calcium entry is performed. For CF, a lead ligand is tested rigorously to determine whether it rescues chloride secretion in in vitro and in vivo human airway epithelial models. For diabetes, a lead ligand is tested rigorously to determine whether it stimulates insulin secretion in the INS-1 cell line and in primary islets.

Diabetes and Other "Failure to Secrete" Endocrine Disorders can be Controlled by Zinc Because secretion of a vesicle or granule containing a physiological endocrine agonist is linked directly to an increase in cell calcium (usually derived from calcium entry from the extracellular space), these targets and ligands were applied to Type 2 diabetes (diabetes mellitus) (FIGS. 15-18) as well as a host of neural, neuroendocrine and endocrine diseases like diabetes which include, but are not limited to, growth hormone deficiency (pituitary dwarfism), adrenal insufficiency syndromes (Addison's disease), amyotrophic lateral sclerosis (ALS or Lou Gehrig's disease), and Alzheimer's disease.

Example 22

Analysis of the Effect of Zinc Formulations on NFkappaB Induction: Exposure of Airway Epithelial Cells to Zinc and Electrophoretic Mobility Shift Assay (EMSA) of NFkappaB Activity The hzip family of zinc-specific transporters were tested as candidates for providing an entry mechanism for zinc into airway epithelial cells. Although they have been studied primarily in intestinal epithelia critical for zinc absorption as a nutrient, their expression and function in airway epithelial cells had not been investigated previously. Specific RT-PCR experiments designed to characterize the mRNA expression of different hzip transporter subtypes in human airway epithelial cell lines. The human intestinal epithelial cell line, T84, was used as a positive control. Both hzipl and hZip2 PCR products of the expected size were amplified from T84 cell mRNA/cDNA samples. By contrast, only hZip1 was amplified from both non-CF and CF human airway epithelial cell lines. DNA sequencing of these amplified PCR products was performed to insure their authenticity. Taken together, this data showed that the zinc-specific transporter, hzipI, was expressed in both non-CF and CF human airway epithelial cells and can be an entry mechanism for zinc to accumulate in the cytosol to affect cell signaling.

To test whether zinc could gain access to the cell interior, an extensive series of experiments was performed to determine whether one or more inflammatory signaling molecules were affected by zinc in the cytosol. In order to show that zinc could accumulate in the cell, optimization of the use of zinc-sensitive fluorescence indicator dyes was done. One such dye, TFLZn, showed that increasing concentrations of extracellular zinc chloride led to increased fluorescence of zinc inside the cells. This data show that zinc can enter human airway epithelial cells and accumulate in the cytosol as detectable free ionic zinc.

The transcription factor, nuclear factor kappab, plays a key role in transducing numerous different cytolcine, chemokine, and toll receptor-mediated signaling cascades into stimulation of inflammatory gene expression. Overnight (18 hour) incubation and a more acute 2-hour exposure of a non-CF human airway epithelial cell line, 9HTEo-, showed that all three zinc formulations blocked the ability of the epithelial CD40 receptor or the tumor necrosis factor (TNF) alpha to stimulate NFkappaB activity versus the non-zinc treated control. Electrophoretic mobility shift assays (EMSAs) were performed to assess NFkappaB transcription factor activity. A 1:100 dilution of these zinc formulations from the 1× concentration resulted in the re-appearance of NFkappaB induction in the case of the two homeopathic remedies; however, 10 mM and 100 µM zinc sulfate each inhibited NFkappaB induction completely normally triggered by TNFalpha. These data show that zinc is either affecting NFkappaB directly, one of the factors that is upstream of NPkappaB in the cascade, or the IkappaB subunits that bind and prevent NFkappaB from translocating to the nucleus.

Example 23

Analysis of the Effect of Zinc Formulations on the Growth and Survival of Non-mucoid and Mucoid *Pseudomonas aeruginosa, E. coli*, and *Bacillis anthracis*

Zicam™ is formulated as a nasal gel that can be purchased over-the-counter s a homeopathic remedy in two forms. One form is the nasal gel applied with a cotton wab into the nostril. One swab is needed for each nostril of the nose. Another form is he nasal gel squirted into the nose by a pump bottle. Both formulations were used for zincum gluconicum-containing nasal gel for the anti-bacterial experiments. For Luria Broth (LB) medium fluid-phase growth of non-mucoid and mucoid *P. aeruginosa*. lab strains, a cotton swab laden with the Zicam nasal gel was placed into the 5 ml culture spiked with a standard inoculum of bacteria (1 ml of a pre-grown stock). For LB-agar solid-phase growth, different numbers of droplets of Zicam nasal gel were squirted on the plastic culture plate before pouring in the cooling but not yet hardened LB-agar solution that was previously autoclaved and/or microwaved to solubilized the agar. In liquid LB growth medium, increasing amounts of Zicam nasal gel in the preparation showed a dose-dependent inhibition of both non-mucoid and mucoid *P. aeruginosa* growth. The effect was most pronounced when the nasal gel was chronically in the preparation, although some inhibition was noted by just dipping the nasal swab in the culture for a finite period of time.

ColdEeze™ is formulated as a throat lozenge that is broken down in the mouth by saliva and, thus, administered orally. These lozenges were exceedingly hard, so they were dried, ground into smaller pieces with a morter and pestle, and the smaller fragments were solubilized by heating the LB medium or the liquid LB-agar solution before solidification. As with the Zicam homeopathic preparation, increasing amounts of ColdEeze also inhibited the growth of non-mucoid and mucoid *P. aeruginosa* in a dose-dependent manner. More concentrated ColdEeze-containing preparations turned the medium orange due to a higher amount of the red dye contained in each lozenge which interfered with the OD reading. This was not a problem in the LB-agar plate growth studies, where ColdEeze, like Zicam, inhibited the growth of both non-mucoid and mucoid *P. aeruginosa* bacterial lawns. Nevertheless, these data show that a second homeopathic zinc gluconate-containing remedy is also bacteriastatic for both non-mucoid and mucoid *P. aeruginosa*. The zinc gluconate (zincum gluconicum) common to these two preparations was the active ingredient that inhibited bacterial growth.

Pharmacy-grade zinc sulfate and other zinc formulations obtained from Sigma (data not shown) were used to obtain dosage amounts. The amounts of zinc added to the system were carefully controlled. Zinc was effective in a range between 100 micromolar and 10 millimolar, with the IC50 falling at approximately 1-5 mM. LB-agar plate studies showed that 4 mM zinc sulfate produced the same degree of growth inhibition that the more concentrated or higher doses of both homeopathic remedies. This result was similar with all of the different known zinc formulations solubilized in water and added to the LB media, liquid or agar.

Both non-mucoid and mucoid *P. aeruginosa* were streaked onto LB-agar plates and then added to filter discs soaked with different amounts and types of homeopathic and other zinc formulations. Small halos were observed reflecting bacterial killing for the Zicam filter disc quadrant but not for the control quadrants. Upon removing the discs, there was no growth underneath the discs soaked in Zicam. In fact, in non-mucoid *P. aeruginosa* cultures, there were only small halos as well; however, the more striking inhibition with Zicam and ColdEeze-soaked discs versus controls was the diffusion of zinc into the agar that prevented the green autofluorescence caused by the secreted siderophores in a manner similar to that shown above. However, in this case, the edges not exposed to the diffused zinc did turn green. Larger halos were observed at higher zinc concentrations either with zinc sulfate (millimolar) or the two homeopathics when top agar overlays containing bacteria growing in log phase were overlaid onto bottom agar as a substrate. Halos indicative of bacterial killing were found for both non-mucoid and mucoid *P. aeruginosa*. but also for *E. coli* and *Bacillus anthracis*. An example of a halo of bacterial killing is shown for *E coli*; however, data for all of the other bacterial pathogens listed were similar.

Zinc can competitively inhibit the ability of both non-mucoid and mucoid *P. aeruginosa* to scavenge ferric iron. This pathway prefers ferric iron over ferrous iron, suggesting that divalent metal cations interfere with this system critical for *P. aeruginosa* growth and survival in the host. As such, competition experiments between ferric sulfate and ferrous sulfate and/or zinc sulfate were conducted. These data showed mucoid *P. aeruginosa* after 4 hours of growth in liquid LB medium. Ferric iron enhanced growth significantly, while zinc sulfate inhibits it as before. Together, zinc sulfate and ferric sulfate were additive in their inhibition. Sub-maximal stimulatory doses of ferric iron as well as inhibitory doses of the divalent metals were used to perform these competition studies. Taken together, these data showed that zinc sulfate acts like ferrous sulfate to inhibit *P. aeruginosa* growth.

Example 24

$Zn^{2+}$ Triggers an ER-Derived $Ca^{2+}$ Release in IB3-1 Cells after Depleting Endoplasmic Reticulum $Ca^{2+}$ Stores with Thapsigargin Zinc-triggered ER-derived $Ca^{2+}$ release, along with zinc entry into the cell to inhibit the plasma membrane $Ca^{2+}$ ATPase pump, contributes to the robust and sustained nature of the $Ca^{2+}$ signal. A full dose-response analysis with zinc has been done, which shows that 50 µM $ZnCl_2$ gives a maximal response, while the EC50 for this zinc-induced sustained $Ca^{2+}$ plateau was approximately 20 µM.

Throughout this application, various publications are referenced. The disclosures of these publications in their entireties are hereby incorporated by reference into this application in order to more fully describe the state of the art to which this invention pertains.

REFERENCES

1. Rugolo, M. et al. ATP and A1 adenosine receptor agonists mobilize intracellular calcium and activate $K^+$ and $Cl^-$ currents in normal and cystic fibrosis airway epithelial cells. *J. Biol. Chem.* 268, 24779-24784 (1993).
2. Tarran, R. et al. Regulation of murine airway surface liquid volume by CFTR and $Ca^{2+}$-activated $Cl^-$ conductances. *J. Gen. Physiol.* 120, 407-418 (2002).
3. Riordan, J. R., Rommens, J. M., Kerem, B., Alon, N., Rozmahel, R., Grzelczak, Z., Zielenski, J., Lok, S., Plavsic, N., Chou, J. L., Drumm, M. L., Iannuzzi, M. C., Collins, F. S., and Tsui L. C. (1989) *Science* 245, 1066-1073
4. Gregory, R. J., Cheng, S. H., Rich, D. P., Marshall, J., Paul, S., Hehir, K., Ostedgaard, L., Klinger, K. W., Welsh, M. J., and Smith, A. E. (1990) *Nature* 27, 382-386
5. Berger, H. A., Anderson, M. P., Gregory, R. J., Thompson, S., Howard, P. W., Maurer, R. A., Mulligan, R., Smith, A. E., and Welsh, M. J. (1991) *J. Clin. Invest.* 88, 1422-1431
6. Schreiber, R., Greger, R., Nitschke, R., and Kunzelmann, K. (1997) *Pflügers Arch.* 434, 841-847.
7. Fuller C M, Benos D J. (2000) *News Physiol. Sci.* 15: 165-171.
8. Krebs N F, Westcott J E, Arnold T D, Kluger B M, Accurso F J, Miller L V, and Hambridge K M. (2000) *Pediatr. Res.* 48: 256-261.
9. Troung-Tran A Q, Carter J, Ruffin R, and Zalewski P D. (2001) *Immunol. Cell Biol.* 79:170-177.
10. Wang K, Zhou B, Kup Y-M, and Gitschier J. (2002) *Am. J. Human Geizet.* 7: 66-73.
11. North R A. (2002) *Physiol. Rev.* 82: 1013-1067.
12. Zsembery et al. Submitted 2003. Waiting on Result from JBC . . .
13. Davis P B, Drumm M L, and Konstan M W. (1996) *Am. J. Respir. Crit. Care Med.* 154:1229-1256.
14. Cho Y H, Lee S J, Kim S W, Lee C B, Lee W Y, and Yoon M S. (2002) *Int. J. Antimicrob. Agents* 19: 576-582.
15. Moran J, Addy M, Corry D, Newcombe R G, and Haywood J. (2001). *J. Clin. Periodontal* 28: 157-161.
16. Grantham J J. (2001) *Curr. Opin. Nephrol. Hypertens.* 10: 533-542.
17. Wilson P D. (1997) *Am. J. Physiol.* 272: F434-F442.
18. Sutters M and Germino G G. (2003) *J. Lab. Clin. Med.* 141: 91-101.
19. Guay-Woodford L M and Desmond R A. (2003) *Pediatrics* 111: 1072-1080.
20. Praetorius H A and Spring K R. (2001) *J. Membr. Biol.* 184: 71-79.
21. Rohatgi R, Greenberg A, Burrow C R, Wilson P D, and Satlin L M. (2003) *J. Am. Soc. Neph.* 14: 827-836.
22. Schafer J A. (2002) *Am. J. Physiol.* 283: F221-F225.
23. Amuzescu B, Segal A, Flonta M L, Simaels J, and Van Driessche W. (2003) *Pflugers Arch.* 446: 69-77.
24. Sheng S, Perry C J, and Kleyman T R. (2002) *J. Biol. Chem.* 277: 50098-50111.
25. Barg S. (2003). *Pharmacol. Toxicol.* 92: 3-13.
26. Ackerman M J and Clapham D E. (1997) *N. Engl. J Med.* 336: 1575-1586.
27. Leissring M A, Akbari Y, Fanger C M, Cahalan M D, Mattson M P, and LaFerla F M. (2000) *J Cell Biol.* 149: 793-798.
28. Ito E, Oka K, Etcheberrigaray R, Nelson T J, McPhie D L, Tofel-Grehl B., Gibson G E, and Alkon D L. (1994) *Proc. Natl. Acad. Sci. USA* 91: 534-538.
29. http://members.aol.com/henrhbk/endocrine.html,
30. http://www.upei.ca/~cidd/Diseases/endocrine%20diseases/endocrine%20disorders%20list.htm,
31. http://homepage.psy.utexas.edu/HomePage/Class/Psy308/Humm/lectures/05-07Neurotransmitters&Drugs)
32. Button, D., and Brownstein, M. (1993) Aequorin-expressing mammalian cell lines used to report calcium mobilization. Cell Calcium 14, 663-671.
33. Sullivan, E., Tucker, E. M., and Dale, I. L. (1999) Measurement of calcium using the fluorometric imaging plate reader (FLIPR). Calcium Signaling Protocols 114, 125-133.

What is claimed is:

1. A method of increasing cytosolic $Ca^{2+}$ levels in an airway epithelial cell comprising contacting P2X receptors on the cell with an effective amount of $Zn^{2+}$ and one or more of the following molecules: ATP; α, β-methylene-ATP; benzoyl-benzoyl-ATP; ATPγS; or AMPPNP, wherein there is a sustained elevation in cytosolic $Ca^{2+}$ levels in the cell.

2. The method of claim 1, wherein the P2X receptors are not contacted with zincum gluconium.

3. The method of claim 1, wherein the $Zn^+$ is in the form of zinc chloride.

4. The method of claim 1, further comprising
  a. reducing extracellular Na+ or contacting the cell with a $Zn^{2+}$ containing solution with low Na+, or
  b. alkalinizing extracellular fluid or contacting the cell with an alkaline solution containing $Zn^{2+}$, or
  c. reducing extracellular $Mg^{2+}$ or contacting the cell with a $Zn^{2+}$ containing solution with low $Mg^{2+}$, or
  d. increasing extracellular $Ca^{2+}$ or contacting the cell with a $Zn^{2+}$ containing solution with high $Ca^{2+}$, or
  e. any combination of steps a to d.

5. The method of claim 1, further comprising reducing the cell's extracellular Na+ or contacting the cell with a $Zn^{2+}$ containing solution with low Na+.

6. The method of claim 1 or claim 5, further comprising reducing the cell's extracellular $Mg^{2+}$ or contacting the cell with a $Zn^{2+}$ containing solution with low $Mg^{2+}$.

7. The method of claim 1, further comprising reducing the cell's extracellular Na+; alkalinizing the cell's extracellular fluid; reducing the cell's extracellular $Mg^{2+}$; and increasing the cell's extracellular $Ca^{2+}$.

8. The method of claim 5, wherein the cell's extracellular Na+ is reduced by using an effective amount of amiloride.

9. The method of claim 5, wherein the cell's extracellular Na+ is reduced by substituting Na+ with N-methyl-D-glucamine (NMDG).

10. A method of treating an airway disease in a subject, comprising contacting epithelial cells in the trachea, bronchi, bronchioles, or alveoli of a subject with an effective amount of $Zn^{2+}$ and one or more of the following molecules: ATP; α,β-methylene-ATP; benzoyl-benzoyl-ATP; ATPγS; or AMPPNP, wherein there is a sustained elevation in cytosolic $Ca^{2+}$ levels in the cells.

11. The method of claim 10 further comprising
   a. reducing extracellular Na+ or contacting the cell with a $Zn^{2+}$ containing solution with low Na+, or
   b. alkalinizing extracellular fluid or contacting the cell with an alkaline solution containing $Zn^{2+}$, or
   c. reducing extracellular $Mg^{2+}$ or contacting the cell with a $Zn^{2+}$ containing solution with low $Mg^{2+}$, or
   d. increasing extracellular $Ca^{2+}$ or contacting the cell with a $Zn^{2+}$ containing solution with high $Ca^{2+}$, or
   e. any combination of steps a to d.

12. The method of claim 10, wherein the contacting step is performed with $Zn^{2+}$; and ATP; α,β-methylene-ATP; benzoyl-benzoyl-ATP; ATPγS; or AMPPNP-containing inhalant, nebulization, aerosol, or instillant.

13. The method of claim 10, wherein the $Zn^{2+}$ is in the form of zinc chloride ($ZnCl_2$).

* * * * *